(12) United States Patent
Yang et al.

(10) Patent No.: US 10,135,005 B2
(45) Date of Patent: Nov. 20, 2018

(54) DELAYED FLUORESCENCE COMPOUND, AND ORGANIC LIGHT EMITTING DIODE AND DISPLAY DEVICE USING THE SAME

(71) Applicant: LG Display Co., Ltd., Seoul (KR)

(72) Inventors: Joong-Hwan Yang, Gwangmyeong-si (KR); Kyung-Jin Yoon, Goyang-si (KR); Hyo-Jin Noh, Paju-si (KR); Dae-Wi Yoon, Paju-si (KR); In-Ae Shin, Paju-si (KR); Jun-Yun Kim, Goyang-si (KR)

(73) Assignee: LG Display Co., Ltd., Seoul (KR)

( * ) Notice: Subject to any disclaimer, the term of this patent is extended or adjusted under 35 U.S.C. 154(b) by 0 days.

(21) Appl. No.: 15/920,358

(22) Filed: Mar. 13, 2018

(65) Prior Publication Data

US 2018/0205023 A1 Jul. 19, 2018

Related U.S. Application Data

(63) Continuation of application No. 14/938,723, filed on Nov. 11, 2015, now Pat. No. 9,954,186.

(30) Foreign Application Priority Data

Nov. 12, 2014 (KR) .................. 10-2014-0156946
Nov. 28, 2014 (KR) .................. 10-2014-0169004
(Continued)

(51) Int. Cl.
*H01L 51/46* (2006.01)
*H01L 51/00* (2006.01)
(Continued)

(52) U.S. Cl.
CPC ........ *H01L 51/0072* (2013.01); *C07D 219/02* (2013.01); *C07D 401/10* (2013.01);
(Continued)

(58) Field of Classification Search
CPC .............. H01L 51/0072; H01L 51/005; H01L 51/0067; H01L 51/0071; H01L 51/0074;
(Continued)

(56) References Cited

U.S. PATENT DOCUMENTS

2010/0171417 A1 7/2010 Kitamura et al.
2012/0319052 A1 12/2012 Brocke et al.
(Continued)

FOREIGN PATENT DOCUMENTS

CN 103483332 A 1/2014
EP 2862913 A1 4/2015
(Continued)

OTHER PUBLICATIONS

European Search Report, European Patent Application No. 15193864. 4, dated Mar. 31, 2016, eight pages.
(Continued)

*Primary Examiner* — Jayne L Mershon
(74) *Attorney, Agent, or Firm* — Fenwick & West LLP

(57) ABSTRACT

Embodiments relate to a delayed fluorescence compound of Formula 1:

(Continued)

or Formula 2:

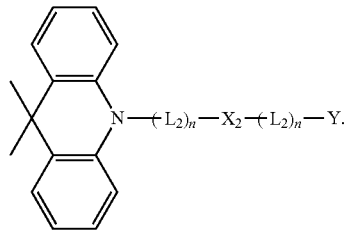

The excitons in the triplet state are engaged in emission such that the emitting efficiency of the delayed fluorescent compound is increased. Embodiments also relate to a display device with an organic light emitting diode (OLED) that includes the delayed fluorescence compound.

17 Claims, 12 Drawing Sheets

(30) Foreign Application Priority Data

| | | | |
|---|---|---|---|
| Nov. 28, 2014 | (KR) | ........................ | 10-2014-0169077 |
| Oct. 8, 2015 | (KR) | ........................ | 10-2015-0141568 |
| Oct. 8, 2015 | (KR) | ........................ | 10-2015-0141569 |
| Oct. 8, 2015 | (KR) | ........................ | 10-2015-0141570 |

(51) Int. Cl.

| | |
|---|---|
| *C07D 495/04* | (2006.01) |
| *C07D 401/14* | (2006.01) |
| *C07D 409/14* | (2006.01) |
| *C07D 471/04* | (2006.01) |
| *C07D 401/10* | (2006.01) |
| *C09K 11/02* | (2006.01) |
| *C09K 11/06* | (2006.01) |
| *C07D 219/02* | (2006.01) |
| *H01L 27/32* | (2006.01) |
| *H01L 51/52* | (2006.01) |
| *H01L 51/50* | (2006.01) |

(52) U.S. Cl.
CPC ......... *C07D 401/14* (2013.01); *C07D 409/14* (2013.01); *C07D 471/04* (2013.01); *C07D 495/04* (2013.01); *C09K 11/025* (2013.01); *C09K 11/06* (2013.01); *H01L 27/3244* (2013.01); *H01L 51/005* (2013.01); *H01L 51/0067* (2013.01); *H01L 51/0071* (2013.01); *H01L 51/0074* (2013.01); *H01L 51/0094* (2013.01); *C09K 2211/1007* (2013.01); *C09K 2211/1014* (2013.01); *C09K 2211/1029* (2013.01); *C09K 2211/1044* (2013.01); *C09K 2211/1059* (2013.01); *C09K 2211/1092* (2013.01); *H01L 51/0097* (2013.01); *H01L 51/5004* (2013.01); *H01L 51/5016* (2013.01); *H01L 51/5253* (2013.01); *H01L 2251/301* (2013.01); *H01L 2251/308* (2013.01); *H01L 2251/552* (2013.01)

(58) Field of Classification Search
CPC ............ H01L 51/0094; H01L 27/3244; C07D 401/10; C07D 401/14; C07D 409/14; C07D 471/04; C07D 495/04; C09K 11/025; C09K 11/06
See application file for complete search history.

(56) References Cited

U.S. PATENT DOCUMENTS

| | | |
|---|---|---|
| 2015/0141642 A1 | 5/2015 | Adachi et al. |
| 2016/0028025 A1 | 1/2016 | Ogiwara et al. |

FOREIGN PATENT DOCUMENTS

| | | | |
|---|---|---|---|
| JP | 2010-180204 A | | 8/2010 |
| WO | WO 2013/161437 A1 | | 10/2013 |
| WO | WO 2014/017844 A1 | | 1/2014 |
| WO | WO 2014/148493 A1 | | 9/2014 |
| WO | WO 2016-080622 | * | 5/2016 |
| WO | WO 2016/080622 A1 | | 5/2016 |

OTHER PUBLICATIONS

Japan Patent Office, Office Action, Japanese Patent Application No. 2015-222000, dated Oct. 18, 2016, five pages [with concise relevance in English].
Taiwan Intellectual Property Office, Office Action, Taiwanese Patent Application No. 104137021, dated Jul. 7, 2016, six pages.
Tsai, W-L. et al., "A Versatile Thermally Activated Delayed Fluorescence Emitter for Both Highly Efficient Doped and Non-Doped Organic Light Emitting Devices," Chemical Communications, Jul. 20, 2015, pp. 13662-13665, vol. 51, No. 71.

* cited by examiner

Carbazole carbazole core

Carbazole

Acridine core

Acridine core

89°

| Prompt | 7.28 ns |
|---|---|
| Delayed | 0.82 μs | excited state to a ground state such that light is emitted.
The external quantum efficiency of the emitting material
for the EML can be expressed by:

$$\eta_{ext} = \eta_{int} \times \Gamma \times \Phi \times \eta_{out\text{-}coupling}$$

DELAYED FLUORESCENCE COMPOUND, AND ORGANIC LIGHT EMITTING DIODE AND DISPLAY DEVICE USING THE SAME

CROSS-REFERENCE TO RELATED APPLICATIONS

This application is a continuation application of U.S. patent application Ser. No. 14/938,723, filed on Nov. 11, 2015, which claims priority to and the benefit of Republic of Korea Patent Application No. 10-2014-0156946 filed on Nov. 12, 2014, Republic of Korea Patent Application No. 10-2014-0169004 filed on Nov. 28, 2014, Republic of Korea Patent Application No. 10-2014-0169077 filed on Nov. 28, 2014, Republic of Korea Patent Application No. 10-2015-0141568 filed on Oct. 8, 2015, Republic of Korea Patent Application No. 10-2015-0141569 filed on Oct. 8, 2015, and Republic of Korea Patent Application No. 10-2015-0141570 filed on Oct. 8, 2015, all of which are hereby incorporated by reference in their entirety.

BACKGROUND OF THE INVENTION

Field of the Invention

Embodiments of the invention relate to an organic light emitting diode (OLED) and more particularly to a delayed fluorescence compound having excellent emitting efficiency and an OLED and a display device using the delayed fluorescence compound.

Discussion of the Related Art

The requirements of large-size display devices have led to developments in flat panel display devices as an image displaying device. Among the flat panel display devices, the OLED has rapidly developed.

In the OLED, when the electron from a cathode, which serves as an electron-injecting electrode, and a hole from an anode, which serves as a hole-injecting electrode, are injected into an emitting material layer, the electron and the hole are combined and become extinct such that the light is emitted from the OLED. A flexible substrate, for example, a plastic substrate, can be used as a base substrate for the OLED, and the OLED has excellent characteristics of driving voltage, power consumption, and color purity.

The OLED includes a first electrode as an anode on a substrate, a second electrode as a cathode facing the first electrode, and an organic emitting layer therebetween.

To improve the emitting efficiency, the organic emitting layer may include a hole injection layer (HIL), a hole transporting layer (HTL), an emitting material layer (EML), an electron transporting layer (HTL), and an electron injection layer (EIL) sequentially stacked on the first electrode.

The hole is transferred into the EML from the first electrode through the HIL and the HTL, and the electron is transferred into the EML from the second electrode through the EIL and the ETL.

The electron and the hole are combined in the EML to generated excitons, and the excitons are transited from an excited state to a ground state such that light is emitted.

The external quantum efficiency of the emitting material for the EML can be expressed by:

In the above equation, "$\eta_{int}$" is the internal quantum efficiency, "r" is the charge balance factor, "$\Phi$" is the radiative quantum efficiency, and "$\eta_{out\text{-}coupling}$" is the out-coupling efficiency.

The charge balance factor "r" means a balance between the hole and the electron when generating the exciton. Generally, assuming 1:1 matching of the hole and the electrode, the charge balance factor has a value of "1". The radiative quantum efficiency "$\Phi$" is a value regarding an effective emitting efficiency of the emitting material. In the host-dopant system, the radiative quantum efficiency depends on a fluorescent quantum efficiency of the dopant.

The internal quantum efficiency "$\eta_{int}$" is a ratio of the excitons generating the light to the excitons generated by the combination of holes and electrons. In the fluorescent compound, a maximum value of the internal quantum efficiency is 0.25. When the hole and the electron are combined to generate the exciton, a ratio of singlet excitons to triplet excitons is 1:3 according to the spin structure. However, in the fluorescent compound, only the singlet excitons, excluding the triplet excitons, are engaged in the emission.

The out-coupling efficiency "$\eta_{out\text{-}coupling}$" is a ratio of the light emitted from the display device to the light emitted from the EML. When the isotropic compounds are deposited in a thermal evaporation method to form a thin film, the emitting materials are randomly oriented. In this instance, the out-coupling efficiency of the display device may be assumed to be 0.2.

Accordingly, the maximum emitting efficiency of the OLED, including the fluorescent compound as the emitting material, is less than approximately 5%.

To overcome the disadvantage of the emitting efficiency of the fluorescent compound, the phosphorescent compound, in which both singlet excitons and triplet excitons are engaged in emission, has been developed for the OLED.

The red and green phosphorescent compound having a relatively high efficiency are introduced and developed. However, there is no blue phosphorescent compound meeting the requirements in emitting efficiency and reliability.

SUMMARY OF THE INVENTION

Accordingly, the embodiment of the invention is directed to a delayed fluorescence compound and an OLED and a display device using the same that substantially obviate one or more of the problems due to limitations and disadvantages of the related art.

An objective of the embodiment of the invention is to provide a delayed fluorescence compound having high emitting efficiency.

Another objective of the embodiment of the invention is to provide an OLED and a display device having an improved emission efficiency.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the embodiments of the invention, as embodied and broadly described herein, an aspect of an embodiment of the invention provides a delayed fluorescence compound of Formula 1 or Formula 2, an encapsulation film on the organic light emitting diode, and a cover window on the encapsulation film. Formulas 1 and 2 are given by:

[Formula 1]

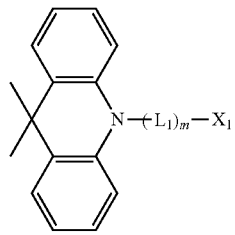

[Formula 2]

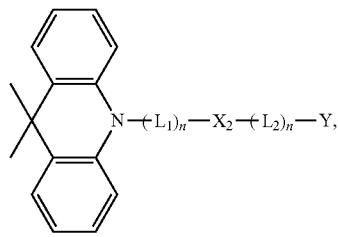

wherein each of m and n is 1 or 0, and $X_1$ is selected from Formula 3, wherein each of $L_1$ and $L_2$ is independently selected from Formula 4, and $X_2$ and Y are respectively selected from Formulas 5 and 6. Formulas 3-6 are given by:

[Formula 3]

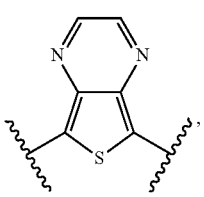

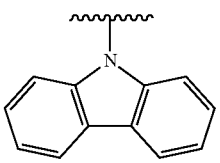

[Formula 4]

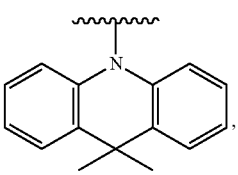

[Formula 5]

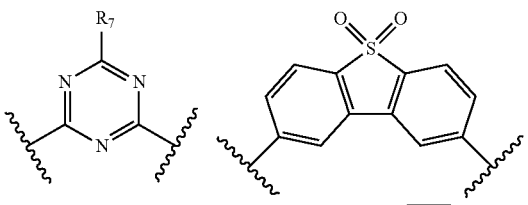

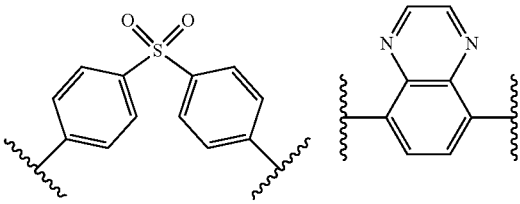

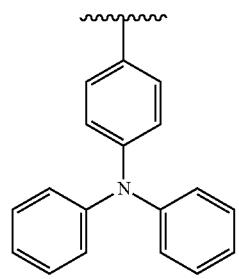

[Formula 6]

wherein each of $R_1$ to $R_4$ in the Formula 3 is independently selected from substituted or non-substituted aryl, and each of $R_5$ and $R_6$ in the Formula 4 is independently selected from hydrogen or C1 alkyl through C10 alkyl, and wherein $R_7$ in the Formula 5 is selected from hydrogen or phenyl.

In another aspect of the embodiment of the invention provided is an organic light emitting diode including a first electrode, a second electrode facing the first electrode, and an organic emitting layer between the first and second electrodes and including a delayed fluorescence compound of Formula 1 or Formula 2, an encapsulation film on the organic light emitting diode, and a cover window on the encapsulation film. Formulas 1 and 2 are given by:

[Formula 1]

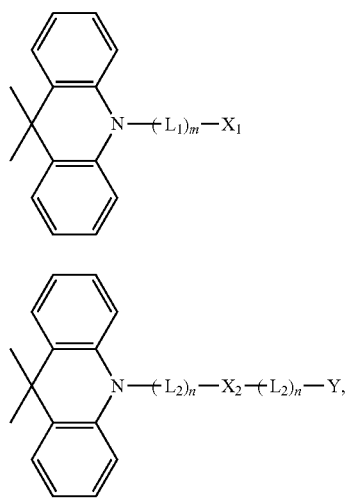

[Formula 2]

wherein each of m and n is 1 or 0, and $X_1$ is selected from Formula 3, wherein each of $L_1$ and $L_2$ is independently selected from Formula 4, and $X_2$ and Y are respectively selected from Formulas 5 and 6. Formulas 3-6 are given by:

[Formula 3]

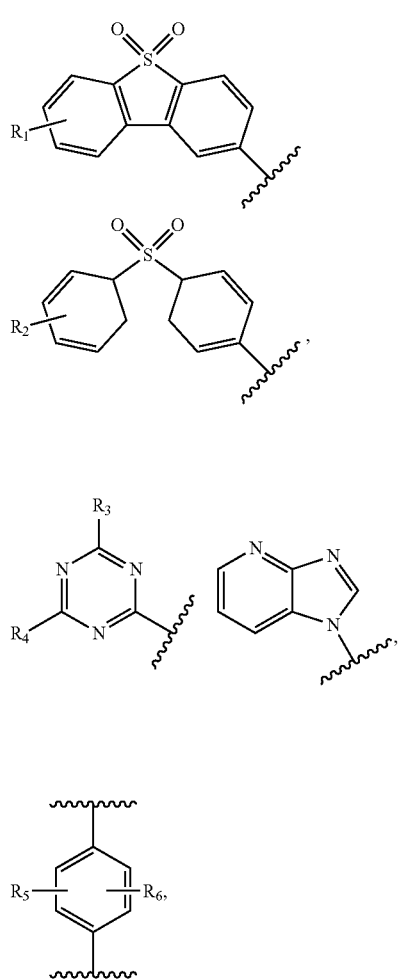

[Formula 4]

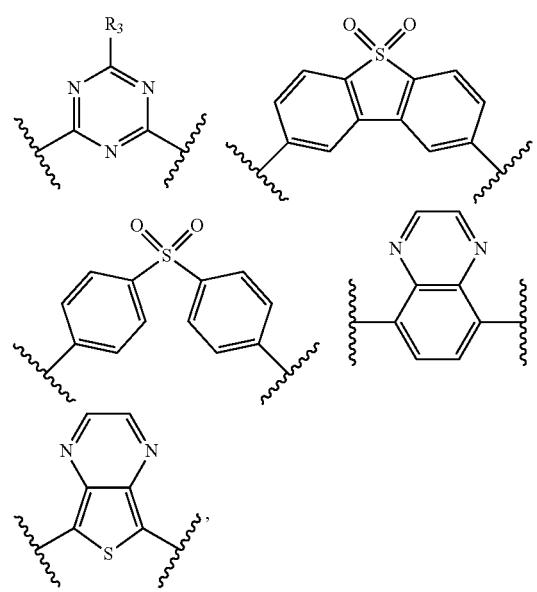

[Formula 5]

[Formula 6]

wherein each of $R_1$ to $R_4$ in the Formula 3 is independently selected from substituted or non-substituted aryl, and each of $R_5$ and $R_6$ in the Formula 4 is independently selected from hydrogen or C1 alkyl through C10 alkyl, and wherein $R_7$ in the Formula 5 is selected from hydrogen or phenyl.

In another aspect of the embodiment of the invention provided is a display device including a substrate; an organic light emitting diode on the substrate and including a first electrode, a second electrode facing the first electrode and an organic emitting layer between the first electrode and the second electrode, the organic emitting layer including a delayed fluorescence compound of Formula 1 or Formula 2, an encapsulation film on the organic light emitting diode, and a cover window on the encapsulation film. Formulas 1 and 2 are given by:

[Formula 1]

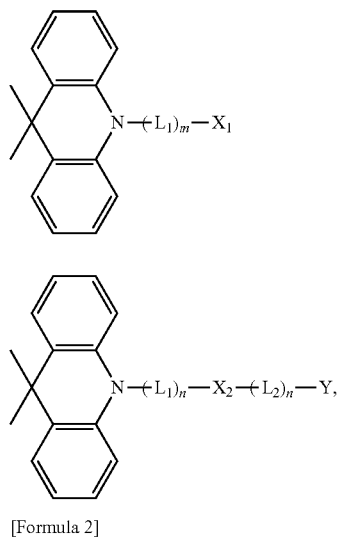

[Formula 2]

wherein each of m and n is 1 or 0, and $X_1$ is selected from Formula 3, wherein each of $L_1$ and $L_2$ is independently selected from Formula 4, and $X_2$ and Y are respectively selected from Formulas 5 and 6. Formulas 3-6 are given by:

[Formula 3]

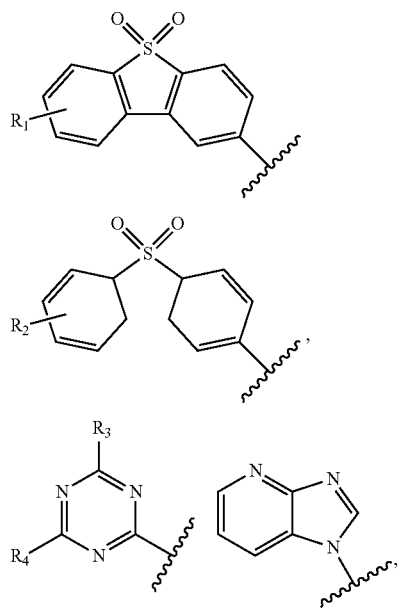

[Formula 4]

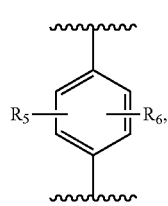

[Formula 5]

[Formula 6]

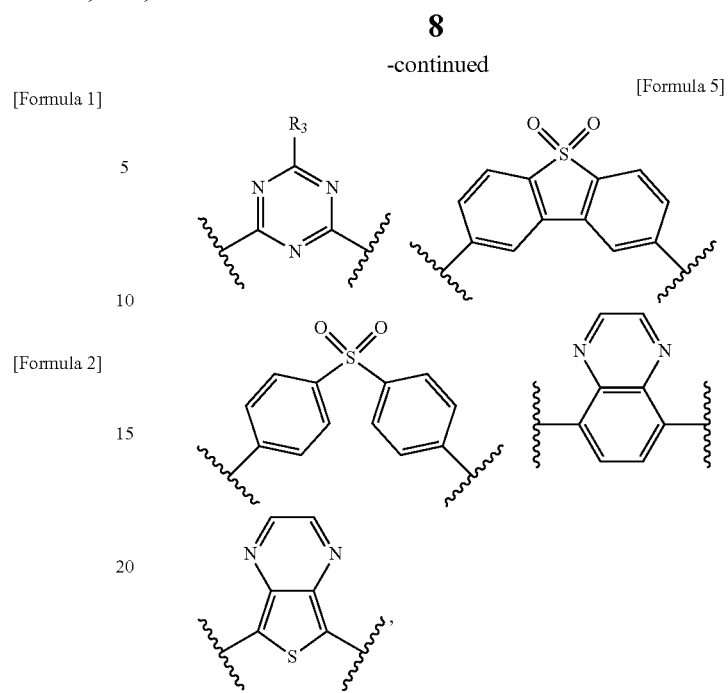

wherein each of $R_1$ to $R_4$ in the Formula 3 is independently selected from substituted or non-substituted aryl, and each of $R_5$ and $R_6$ in the Formula 4 is independently selected from hydrogen or C1 alkyl through C10 alkyl, and wherein $R_7$ in the Formula 5 is selected from hydrogen or phenyl.

It is to be understood that both the foregoing general description and the following detailed description are by example and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE EMBODIMENTS

Figure 1:
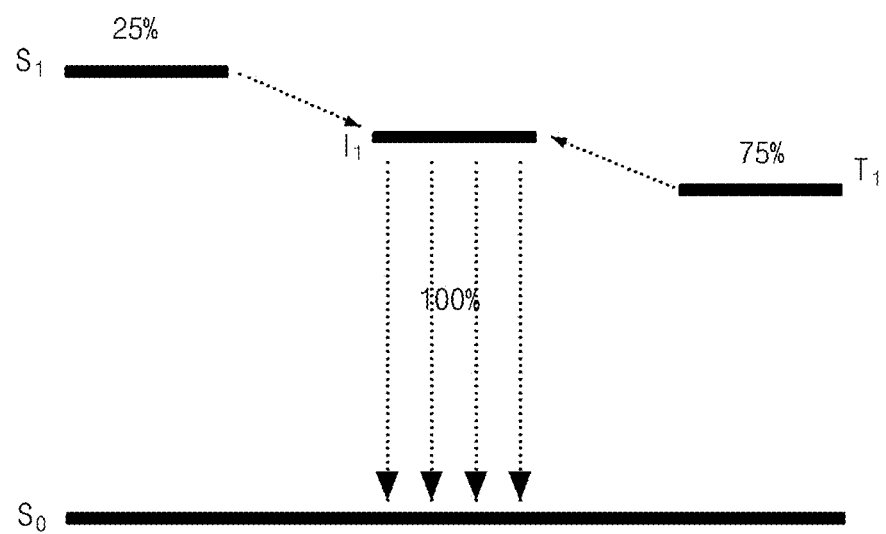
FIG. 1 is a view illustrating an emission mechanism of a delayed fluorescence compound according to the present disclosure.
Figure 2A:
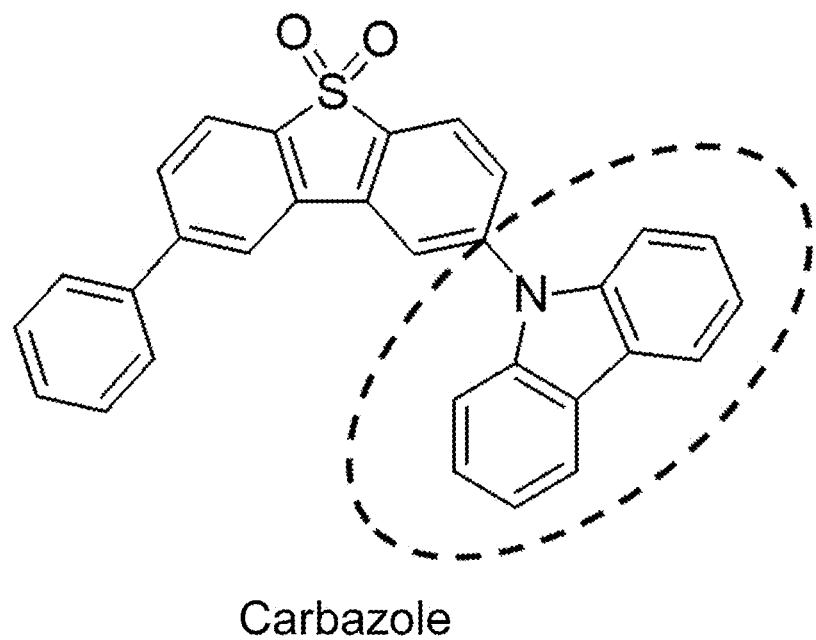
FIGS. 2A to 2F are views respectively illustrating a molecular structure of a compound having a carbazole electron donor moiety.
Figure 2B:
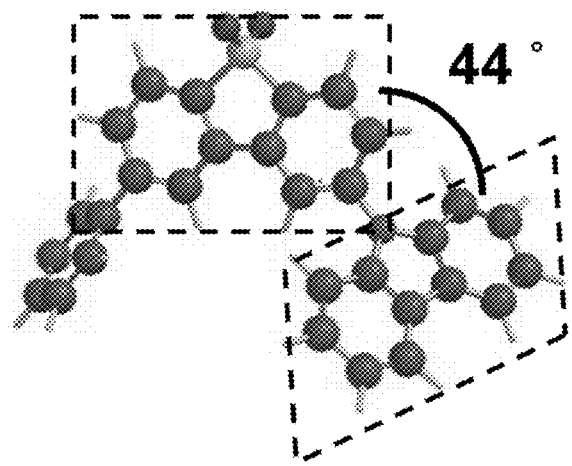
Figure 2C:
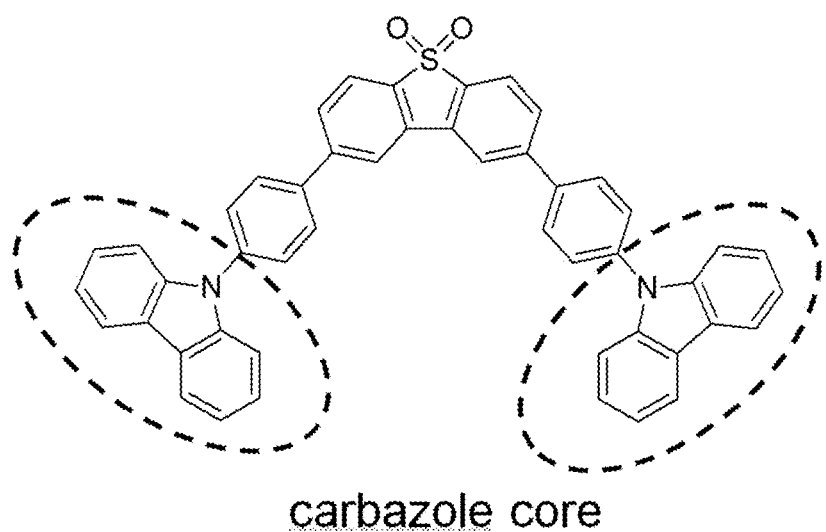
Figure 2D:
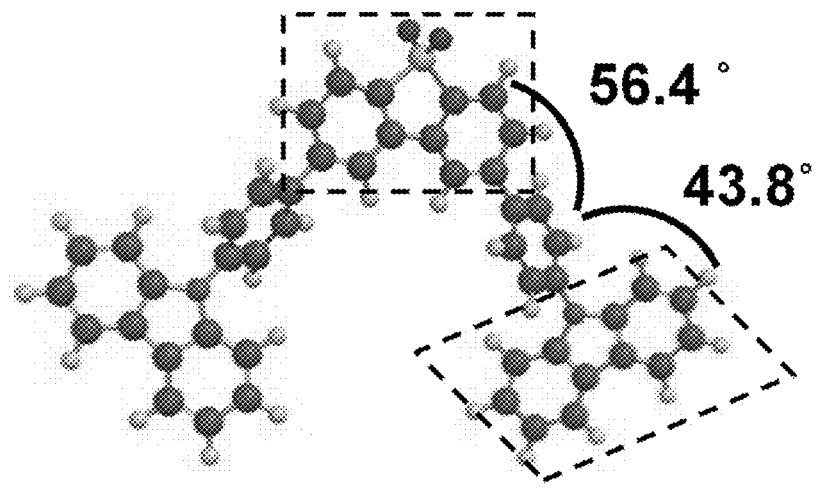
Figure 2E:
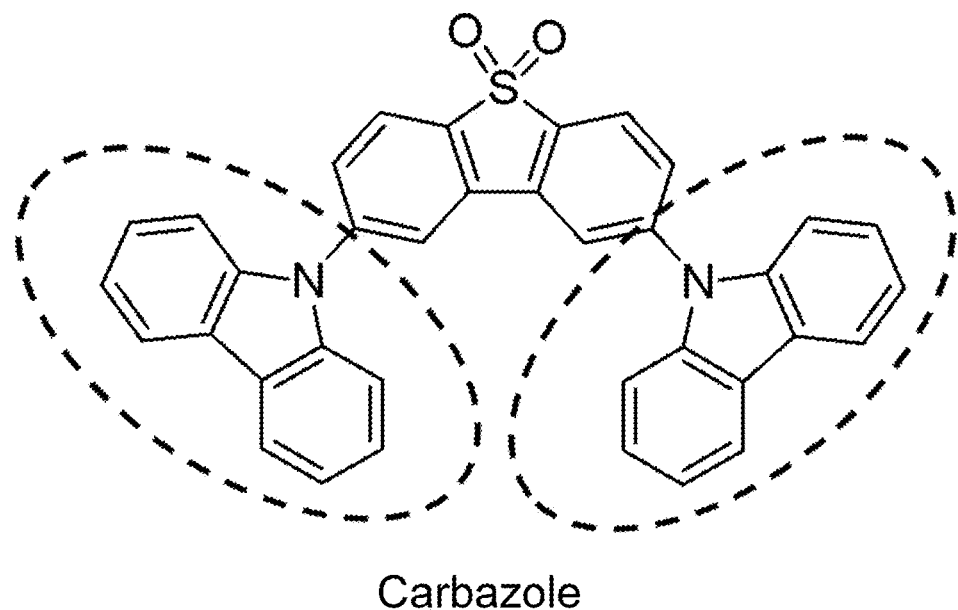
Figure 2F:
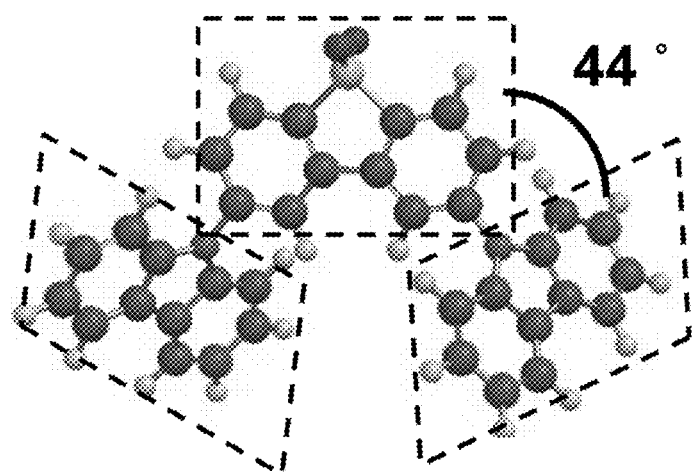
Figure 3A:
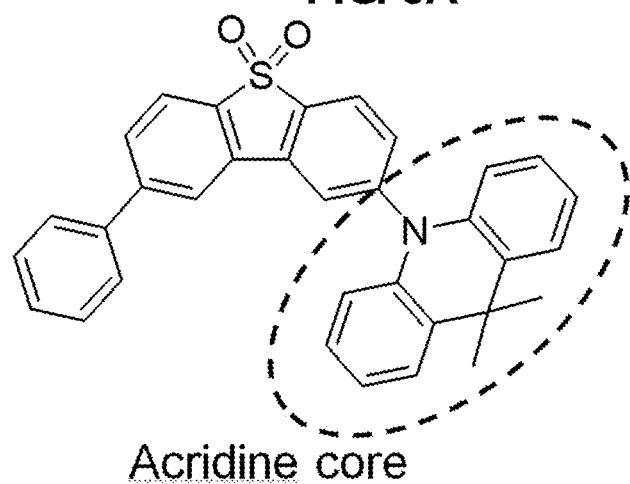
FIGS. 3A to 3F are views respectively illustrating a molecular structure of a compound having an acridine electron donor moiety.
Figure 3B:
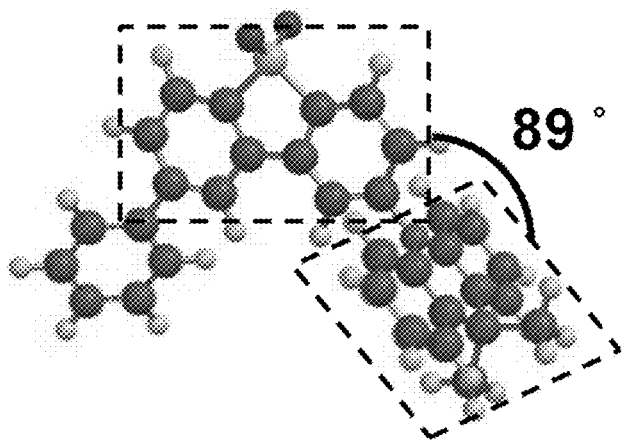
Figure 3C:
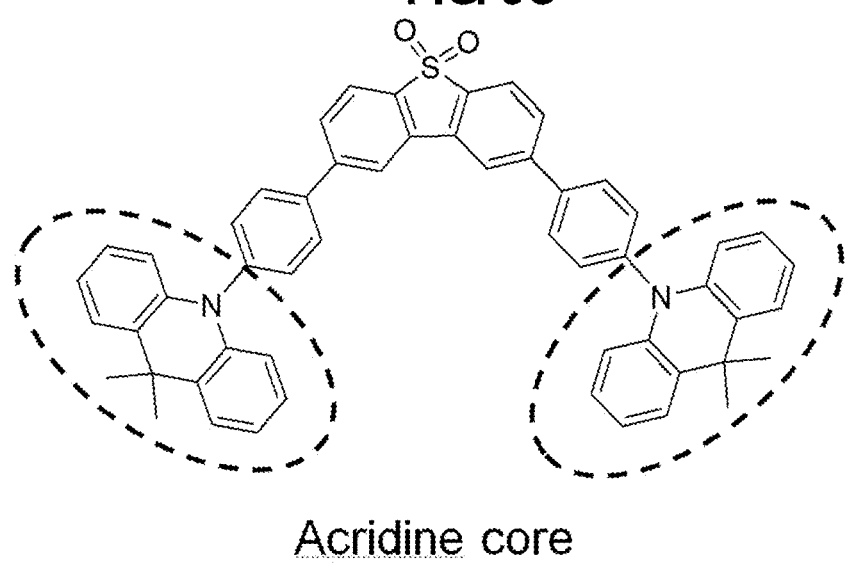
Figure 3D:
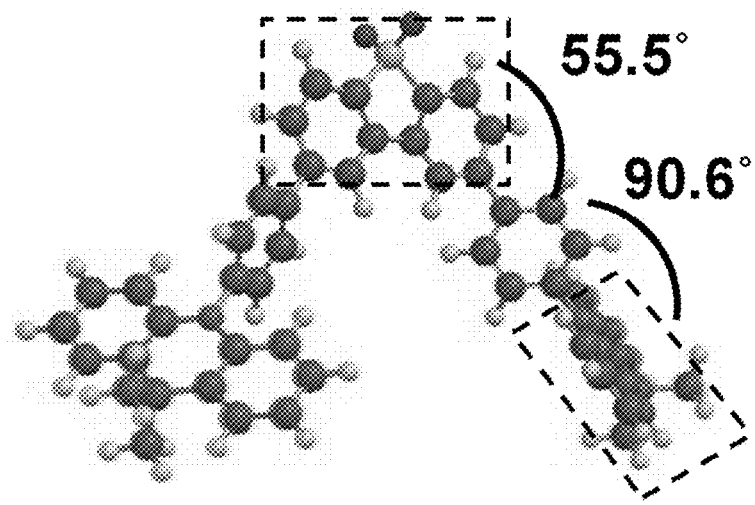
Figure 3E:
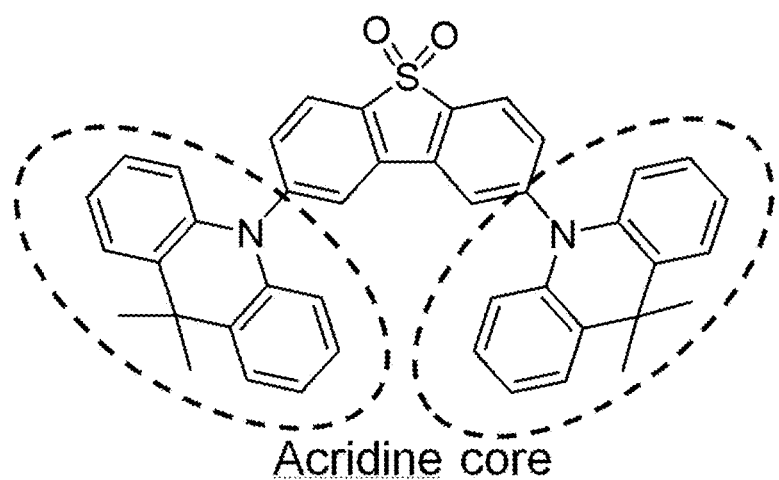
Figure 3F:
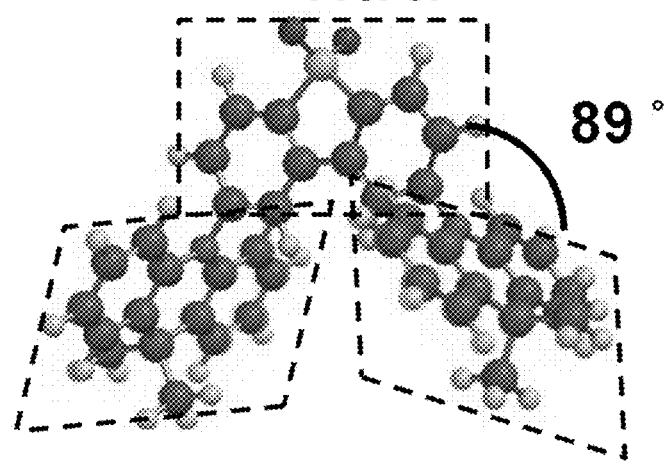
Figure 4A:
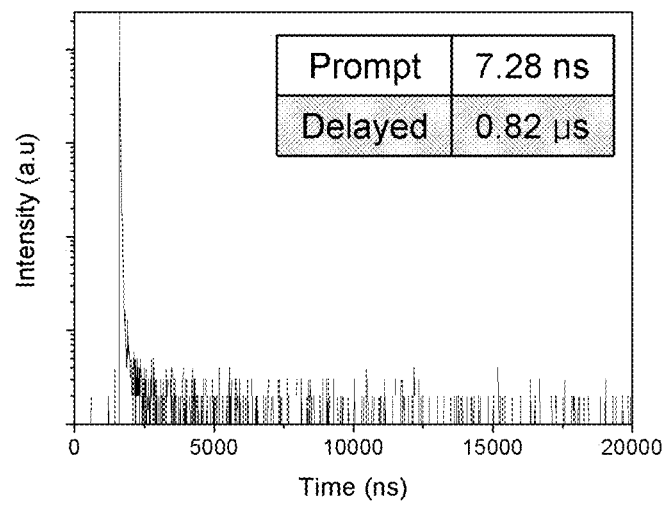
FIGS. 4A to 4J are graphs showing a delayed fluorescent property of a delayed fluorescence compound according to the present disclosure.
Figure 4B:
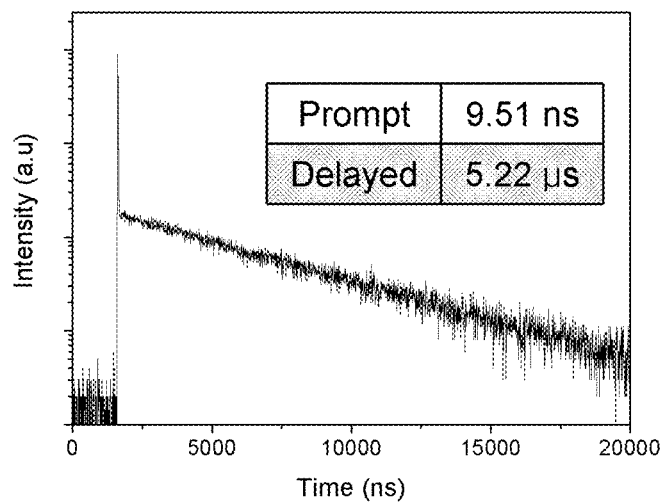
Figure 4C:
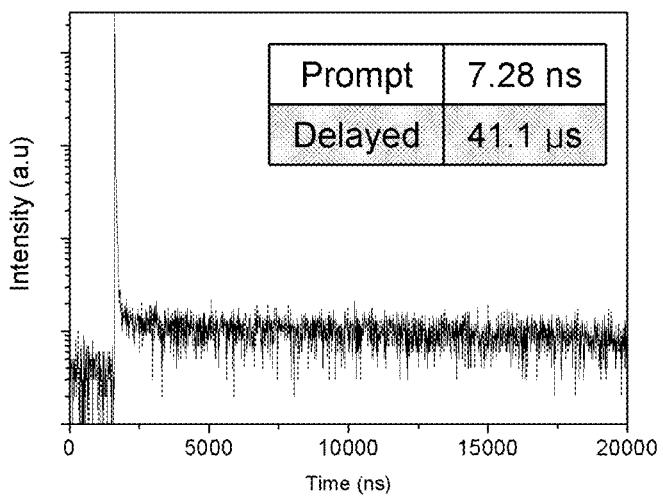
Figure 4D:
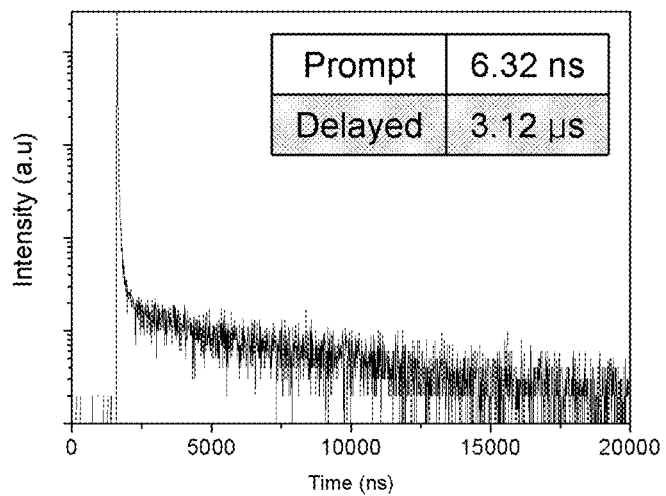
Figure 4E:
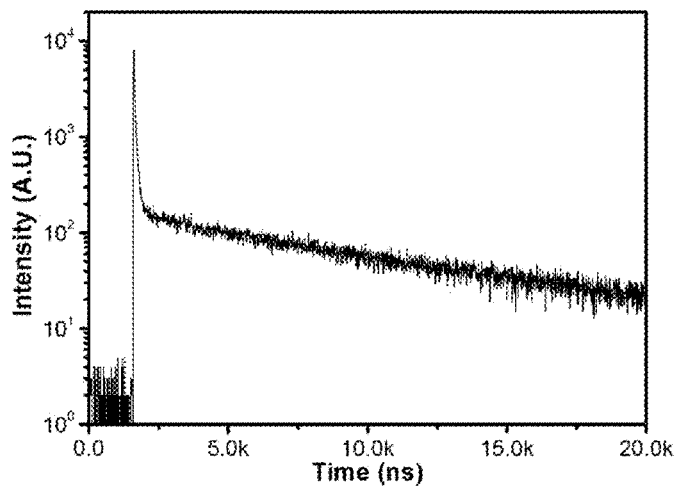
Figure 4F:
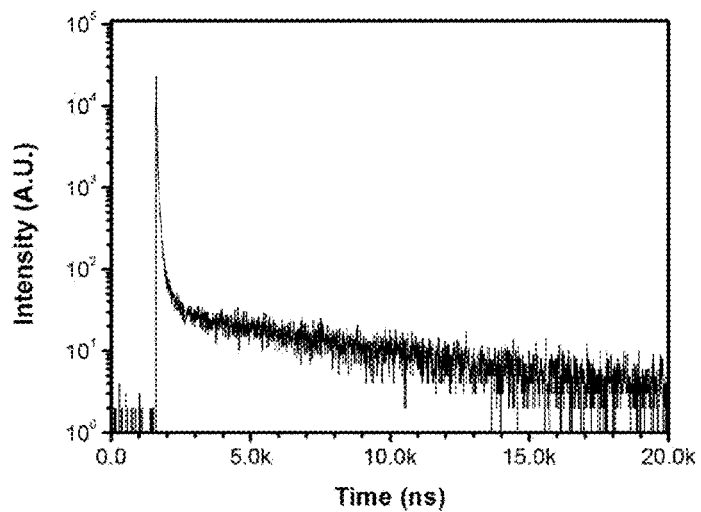
Figure 4G:
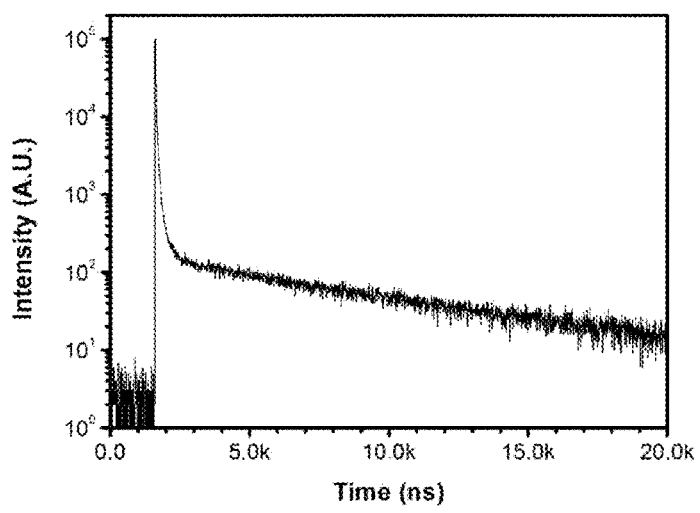
Figure 4H:
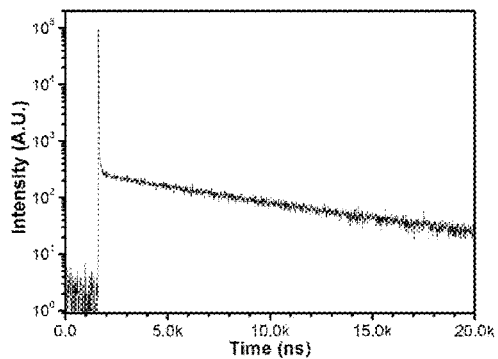
Figure 4I:
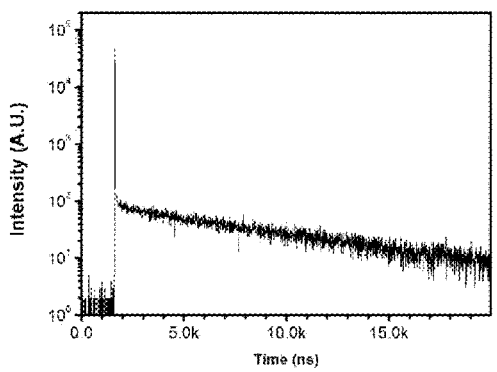
Figure 4J:
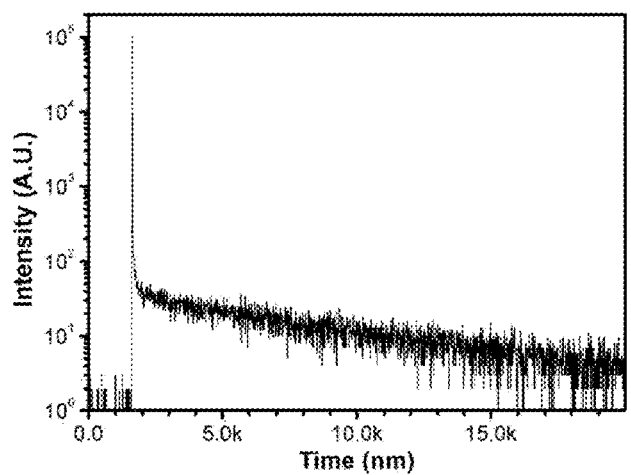

The meanings of terms described in the present specification should be understood as follows.

The singular forms should be understood as including the plural forms as well unless the context clearly indicates otherwise. The terms "first", "second", and the like are used to discriminate any one element from other elements and the scope of the present invention is not intended to be limited by these terms. The terms "comprises" "includes" and the like should be understood as not precluding the presence or addition of one or more other features, integers, steps, operations, elements, components, or combinations thereof. The term "at least one" should be understood as including all combinations that may be suggested from one or more associated items. For example, the meanings of "at least one selected from a first item, a second item, and a third item" includes not only each of the first item, the second item, and the third item, but also all combinations of these items that may be suggested from two or more ones of the first item, the second item, and the third item. In addition, when any one element is referred to as being "on" another element, it can be directly on the upper surface of the other element or a third intervening element may also be present.

Reference will now be made in detail to example embodiments, examples of which are illustrated in the accompanying drawings.

A delayed fluorescence compound of the present disclosure has Formula 1-1 or Formula 1-2 of the followings.

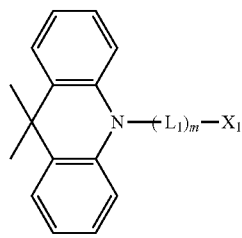

[Formula 1-1]

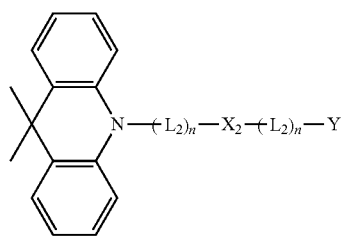

[Formula 1-2]

where each of "m" and "n" is 0 (zero) or 1.

Namely, as shown in Formula 2-1, the delayed fluorescence compound has a structure in which an electron donor moiety of acridine is combined or linked to an electron acceptor moiety $X_1$ with a linker $L_1$ therebetween. Alternatively, as shown in Formula 2-2, the delayed fluorescence compound has a structure in which an electron donor moiety of acridine is directly combined or linked to an electron acceptor moiety $X_1$ without a linker.

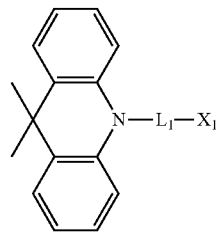

[Formula 2-1]

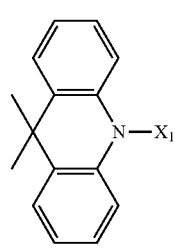

[Formula 2-2]

Alternatively, as shown in Formula 2-3, the delayed fluorescence compound has a structure in which a first electron donor moiety of acridine and a second electron donor moiety Y, which is equal to or different from the first electron donor moiety, are combined or linked to an electron acceptor moiety $X_2$ with a linker $L_2$ therebetween. Alternatively, as shown in Formula 2-4, the delayed fluorescence compound has a structure in which a first electron donor moiety of acridine and a second electron donor moiety Y, which is equal to or different from the first electron donor moiety, are directly combined or linked to an electron acceptor moiety $X_2$ without a linker.

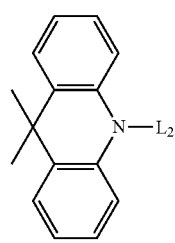

[Formula 2-3]

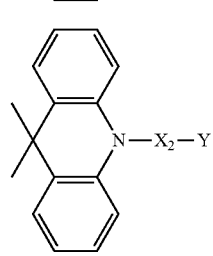

[Formula 2-4]

In the Formulas 2-1 and 2-2, the electron acceptor moiety $X_1$ is selected from substituted or non-substituted triazine, substituted or non-substituted dibenzothiophene, substituted or non-substituted 4-azabenzimidazole, or substituted or non-substituted benzimidazole. For example, the electron acceptor moiety $X_1$ may be selected from materials in Formula 3 of the following.

[Formula 3]

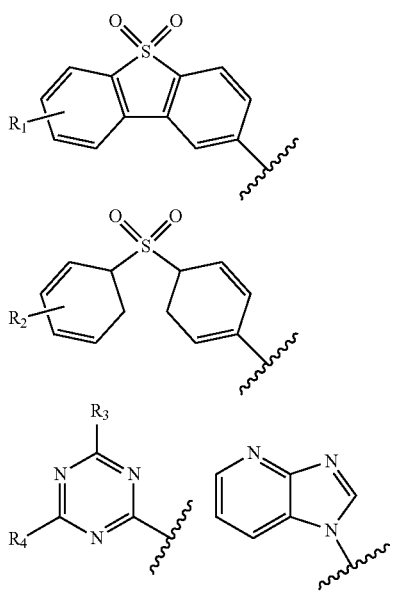

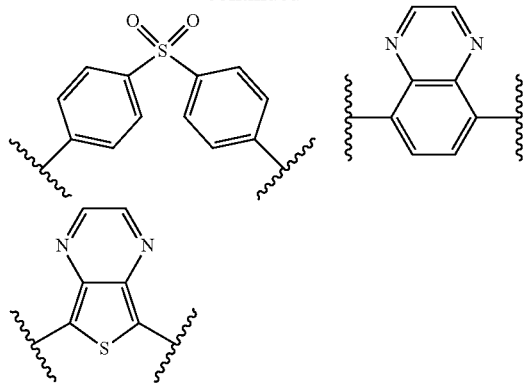

In the Formula 3, each of $R_1$ to $R_4$ is independently selected from hydrogen or substituted or non-substituted aryl. For example, each of $R_1$ to $R_4$ may be selected from hydrogen or non-substituted phenyl.

In the Formulas 1-1, 1-2, 2-1, and 2-3, each of $L_1$ and $L_2$ as the linker is substituted or non-substituted benzene. For example, each of $L_1$ and $L_2$ may be a material in Formula 4 of following.

[Formula 4]

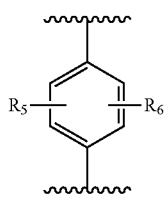

In Formula 4, each of $R_5$ and $R_6$ is independently selected from hydrogen or C1 to C10 alkyl. For example, each of $R_5$ and $R_6$ may be hydrogen or methyl.

In the Formulas 1-2, 2-3, and 2-4, the electron acceptor moiety $X_2$ is selected from substituted or non-substituted phenyltriazine, dibenzothiophenesulfone, diphenylsulfone, quinoxaline, thieno pyrazine, or their derivatives. For example, the electron acceptor moiety $X_2$ may be selected from materials in Formula 5 of the following.

[Formula 5]

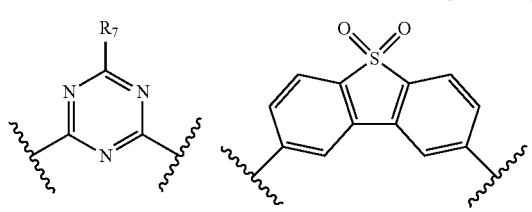

In the Formula 5, $R_7$ is selected from hydrogen or phenyl.

In the Formulas 1-2, 2-3, and 2-4, the second electron donor moiety Y is selected from materials, which is capable of injecting a hole, such as carbazole, triphenyl amine, acridine, or their derivatives. Namely, the second electron donor moiety Y is selected from substituted or non-substituted carbazole, substituted or non-substituted triphenyl amine, or substituted or non-substituted acridine. For example, the second electron donor moiety Y may be selected from materials in Formula 6 of the following.

[Formula 6]

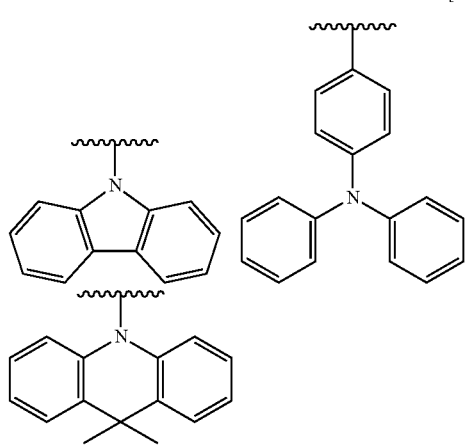

Since the delayed fluorescence compound includes the electron donor moiety and the electron acceptor moiety with or without another electron donor moiety, the charge transfer is easily generated in the molecule and the emitting efficiency is improved. In addition, the dipole from the first and second electron donor moieties to the electron acceptor moiety is generated such that the dipole moment in the molecule is increased. As a result, the emitting efficiency is further improved.

Moreover, in the delayed fluorescent compound of the present disclosure, the excitons in the triplet state are engaged in the emission such that the emitting efficiency of the delayed fluorescent compound is increased.

Further, since acridine, which has a hexagonal structure, is used as the electron donor moiety, a steric hindrance between the electron donor moiety and the electron acceptor moiety is increased, and a dihedral angle between the acridine electron donor moiety and the electron acceptor moiety is also increased. Accordingly, the generation of conjugation between the electron donor moiety and the electron acceptor moiety is limited, and the highest occupied molecular orbital (HOMO) and the lowest unoccupied molecular orbital (LUMO) is easily separated. As a result, the emitting efficiency of the delayed fluorescent compound is further increased.

In the delayed fluorescence compound of the present disclosure, the electron donor moiety and the electron acceptor moiety are combined or linked in the molecule such that an overlap between HOMO and LUMO is reduced. As a result, a field activated complex is generated, and the emitting efficiency of the delayed fluorescence compound is improved.

Since a gap or a distance between the electron donor moiety and the electron acceptor moiety is increased due to the linker, an overlap between HOMO and LUMO is reduced such that a gap ($\Delta E_{ST}$) between the triple energy and the singlet energy is reduced.

In addition, due to the steric hindrance of the linker, the red shift problem in the light emitted from the emitting layer including the delayed fluorescence compound is decreased or minimized. Namely, the emitting layer with the delayed fluorescence compound of the present disclosure provides deep blue emission.

Referring to FIG. 1, which is a view illustrating an emission mechanism of a delayed fluorescence compound according to the present disclosure, in the delayed fluorescence compound of the present disclosure, the triplet excitons as well as the singlet excitons are engaged in the emission such that the emitting efficiency is improved.

Namely, the triplet exciton is activated by a field, and the triplet exciton and the singlet exciton are transferred into an intermediated state "$I_1$" and transited into a ground state "So" to emit light. In other words, the singlet state "$S_1$" and the triplet state "$T_1$" are transited into the intermediated state "$I_1$" ($S_1$->$I_1$<-$T_1$), and the singlet exciton and the triplet exciton in the intermediated state "$I_1$" are engaged in the emission such that the emitting efficiency is improved. The compound having the above emission mechanism may be referred to as a field activated delayed fluorescence (FADF) compound.

In the related art fluorescence compound, since the HOMO and the LUMO are dispersed throughout an entirety of the molecule, the interconversion of the HOMO and the LUMO is impossible. (Selection Rule)

However, in the FADF compound, since the overlap between the HOMO and the LUMO in the molecule is relatively small, the interaction between the HOMO and the LUMO is small. Accordingly, changes of the spin state of one electron do not affect other electrons, and a new charge transfer band, which does not comply with the Selection Rule, is generated.

Moreover, since the electron donor moiety and the electron acceptor moiety are spatially spaced apart from each other in the molecule, the dipole moment is generated in a polarized state. In the polarized state dipole moment, the interaction between the HOMO and the LUMO is further reduced such that the emission mechanism does not comply with the Selection Rule. Accordingly, in the FADF compound, the transition from the triplet state "$T_1$" and the singlet state "$S_1$" into the intermediated state "$I_1$" can be generated such that the triplet exciton can be engaged in the emission.

When the OLED is driven, the intersystem transition (intersystem crossing) from 25% singlet state "$S_1$" excitons and 75% triplet state "$T_1$" excitons to the intermediated state "$I_1$" is generated, and the singlet and triplet excitons in the intermediated state "$I_1$" are transited into the ground state to emit light. As a result, the FADF compound has a theoretic quantum efficiency of 100%.

For example, the delayed fluorescence compound of the present invention may be one of compounds in Formula 7.

[Formula 7]

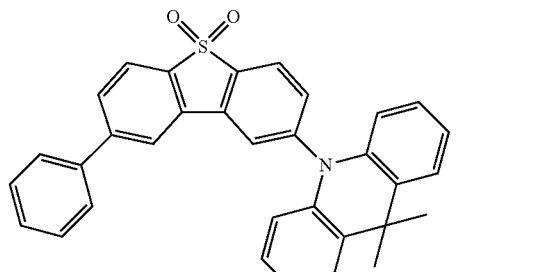

compound 1

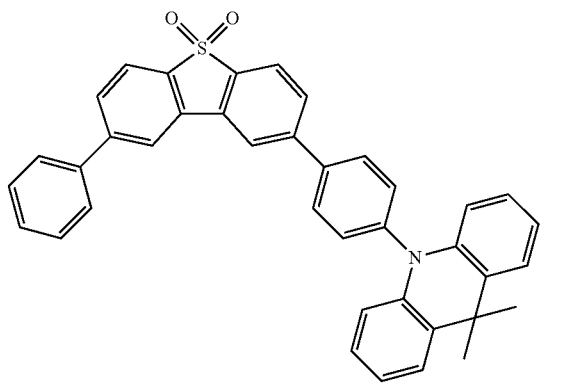

compound 2

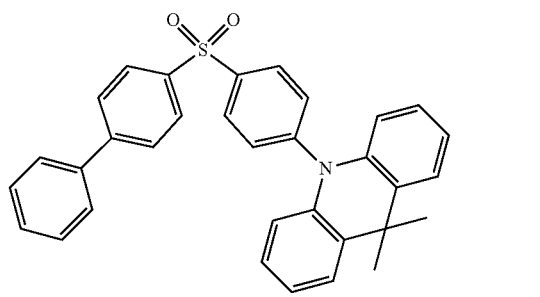

compound 3

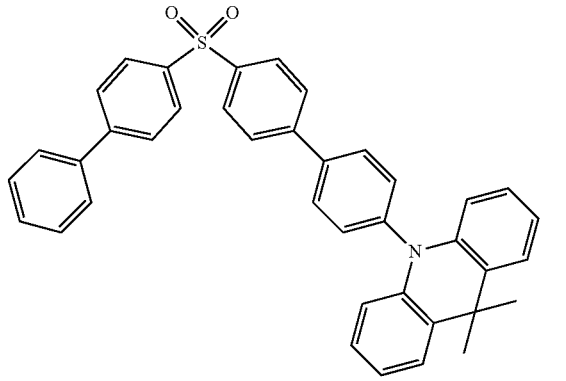

compound 4 compound 5
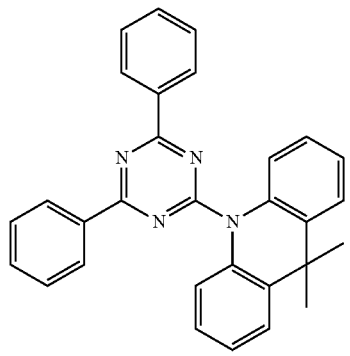
compound 6
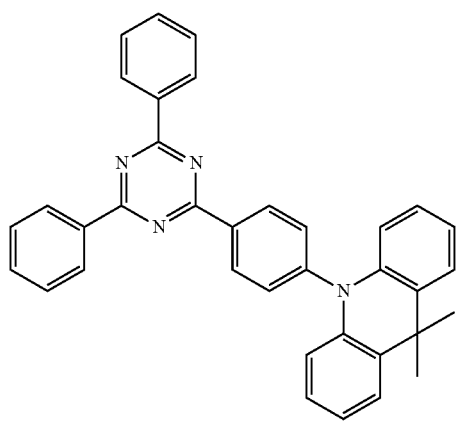
compound 7
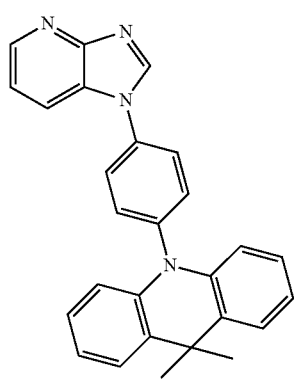
compound 8
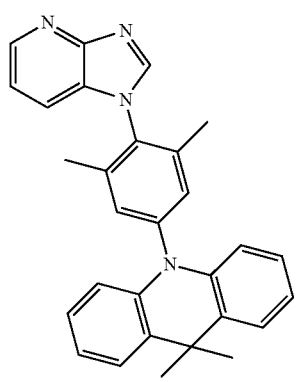
compound 9
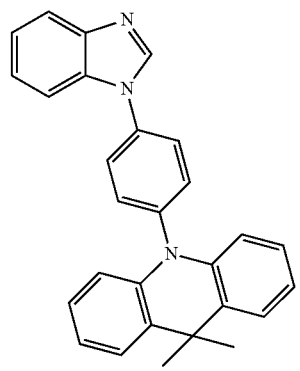
compound 10
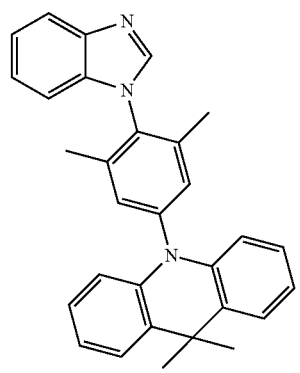
compound 11
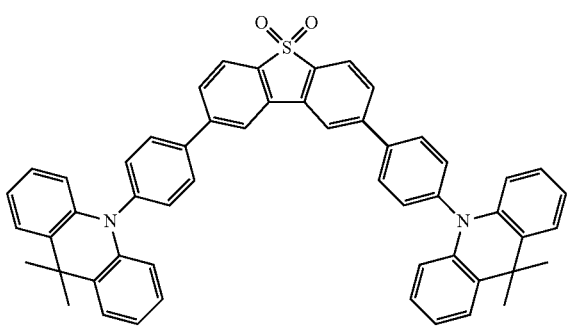
compound 12
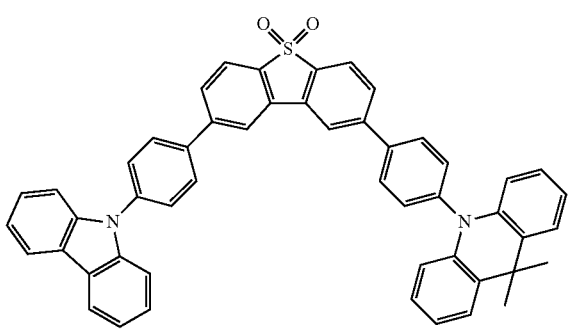

-continued
compound 13
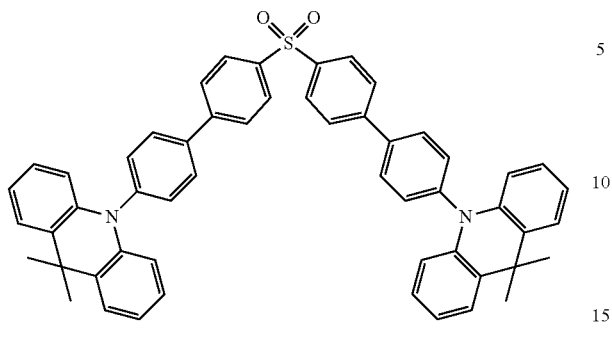
compound 14
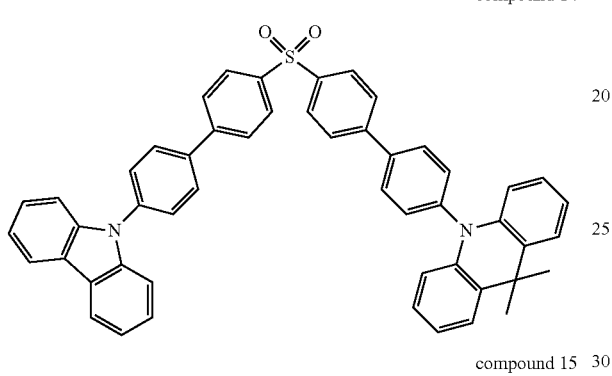
compound 15
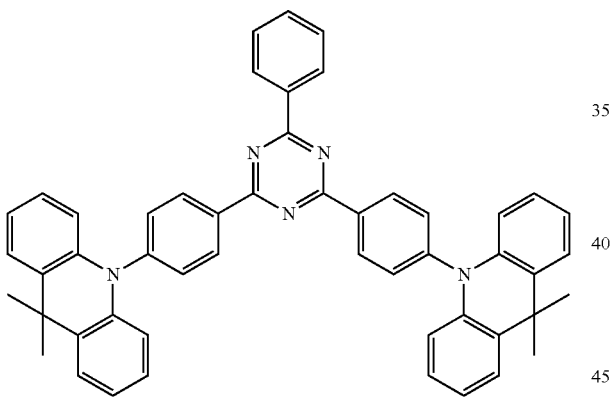
compound 16
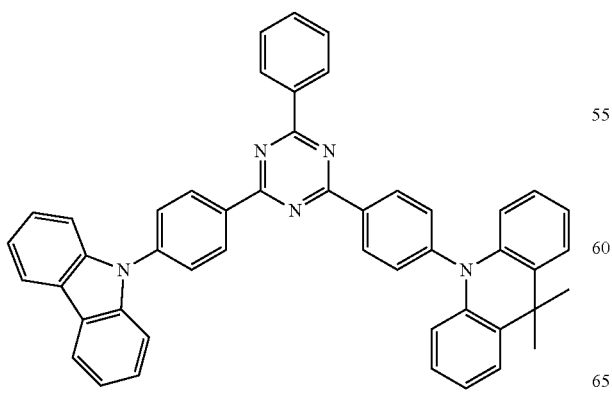
-continued
compound 17
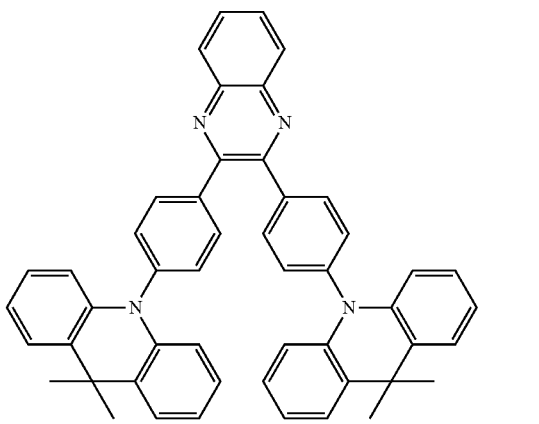
compound 18
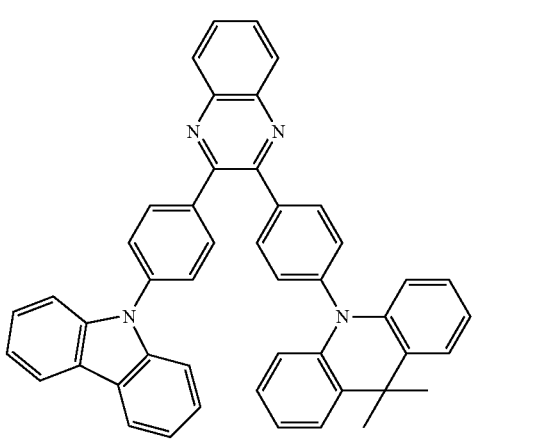
compound 19
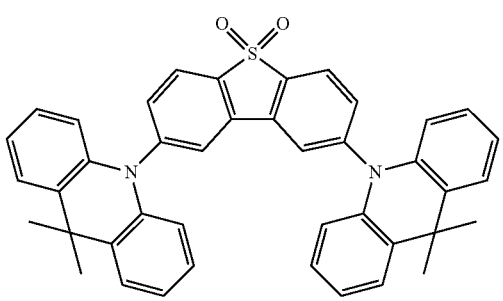
compound 20
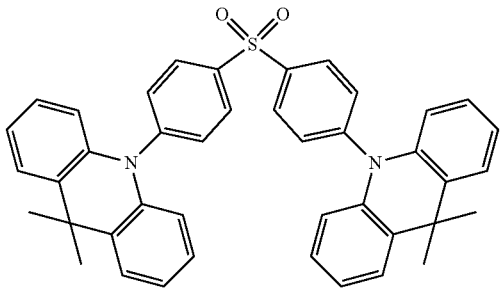

compound 21
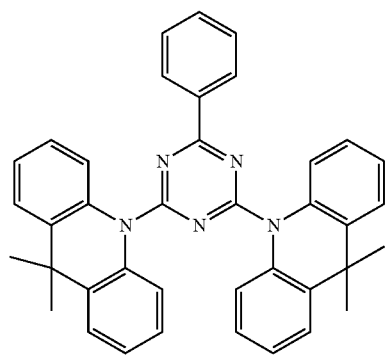
compound 22
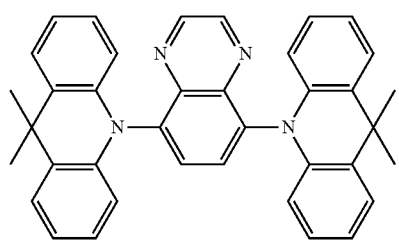
compound 23
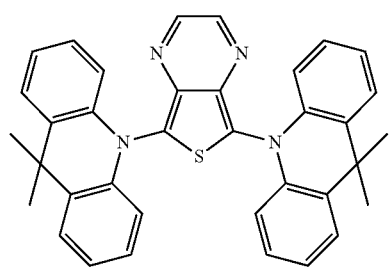
compound 24
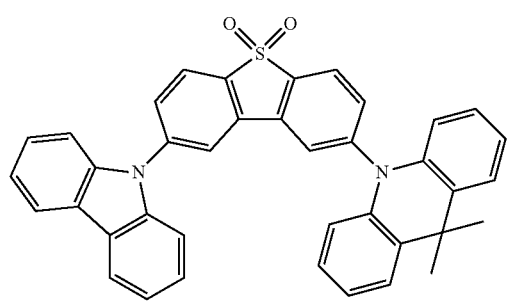
compound 25
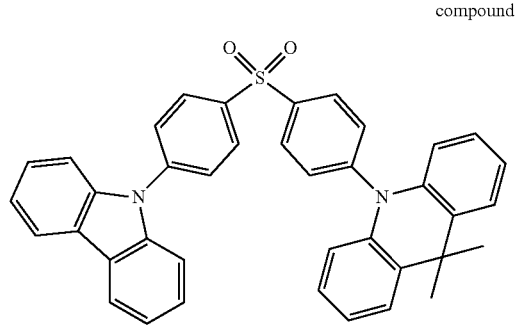
compound 26
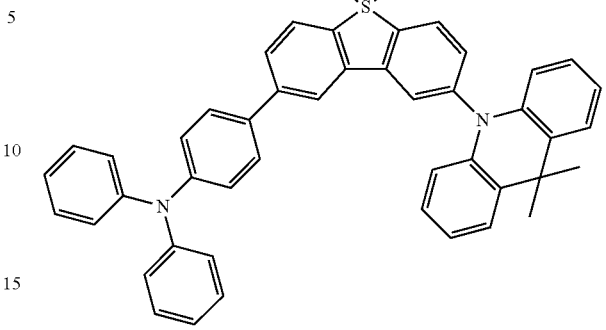
compound 27
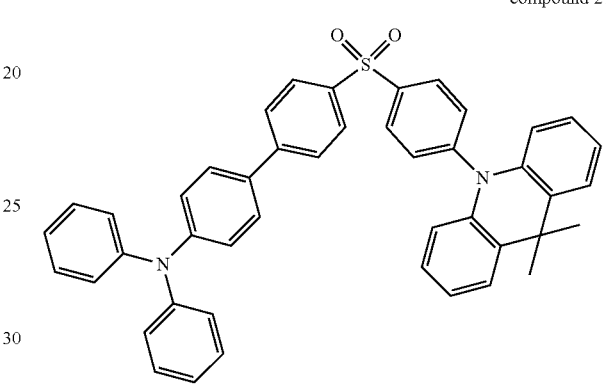
compound 28
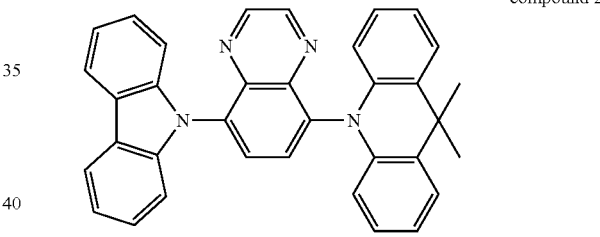
compound 29
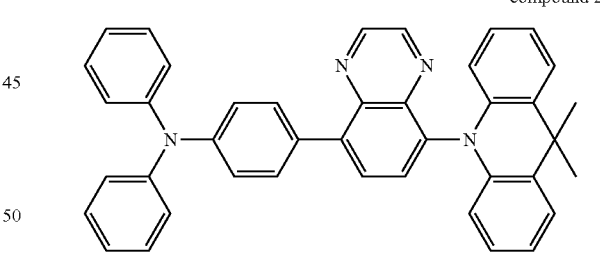
compound 30
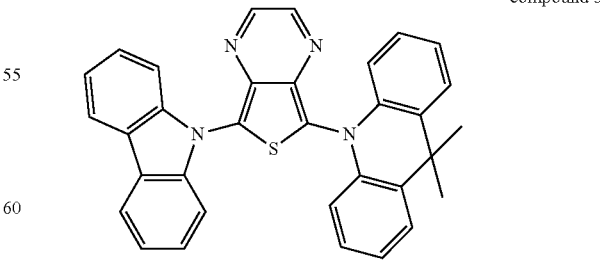
As mentioned above, the delayed fluorescence compound of the present invention includes an acridine electron donor moiety such that a steric hindrance between the electron donor moiety and the electron acceptor moiety is increased, and a dihedral angle between the acridine electron donor moiety and the electron acceptor moiety is also increased.

FIGS. 2A to 2F are views respectively illustrating a molecular structure of a compound having a carbazole electron donor moiety and dibenzothiophenesulfone as an electron acceptor moiety, and FIGS. 3A to 3F are views respectively illustrating a molecular structure of a compound having an acridine electron donor moiety and dibenzothiophenesulfone as an electron acceptor moiety.

Referring to FIGS. 2A to 2F, in the compound including carbazole as the electron donor moiety, the dihedral angle between the electron donor moiety and the electron acceptor moiety (or the linker) is about 44 degrees.

On the other hand, referring to FIGS. 3A to 3F, in the compound including acridine as the electron donor moiety, the dihedral angle between the electron donor moiety and the electron acceptor moiety (or the linker) is about 90 degrees.

Namely, when acridine is used as the electron donor moiety, the dihedral angle between the acridine electron donor moiety and the electron acceptor moiety is increased, and the generation of conjugation between the electron donor moiety and the electron acceptor moiety (or the linker) is limited. As a result, in comparison to the compound including the carbazole electron donor moiety, the HOMO and the LUMO in the compound including the acridine electron donor moiety is easily separated such that the emitting efficiency is further improved.

Synthesis

1. Synthesis of Compound 1

(1) Compound "a"

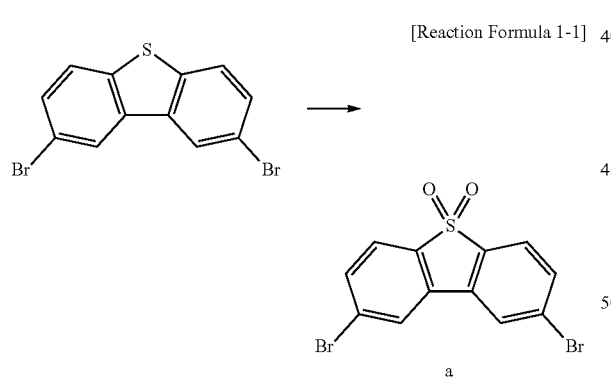

[Reaction Formula 1-1]

a

In the $N_2$ gas purging system, 2,8-dibromodibenzothiophene (14.6 mmol) and acetic acid solvent were mixed and stirred. Hydrogen peroxide (64.8 mmol) was added and stirred in the room temperature for about 30 minutes, and the mixture was refluxed and stirred for 12 hours or more. After completion of the reaction, distilled water (50 ml) was added and stirred to wash. After filtering the mixture, the solids was mixed with excess hydrogen peroxide and stirred to wash for 30 to 60 minutes. The solids was washed by distilled water and filtered and dried such that compound "a" in white solid was obtained. (yield: 90%)

(2) Compound "b"

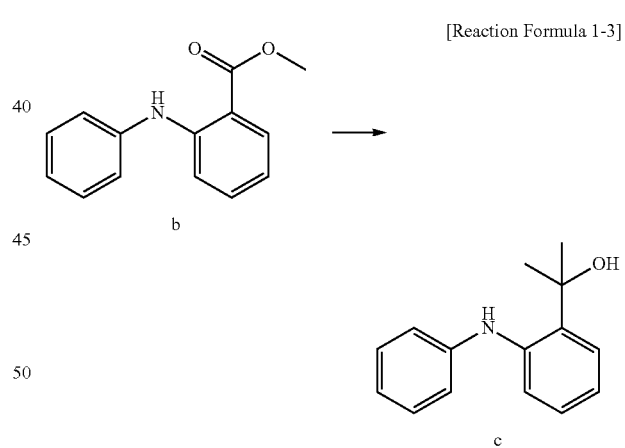

[Reaction Formula 1-2]

b

In the $N_2$ gas purging system, N-phenylanthraniliic acid (46.9 mmol) and methanol solvent were mixed and stirred. The mixture was additionally stirred for 10 minutes under a temperature of 0° C., and thionyl chloride (21.2 mmol) was slowly dropped. The mixed solution was stirred for 12 hours or more under a temperature of 90° C. After completion of the reaction, the solvent was removed, and the mixed solution was extracted by distilled water and ethylacetate. Moisture was removed from the extracted organic layer by using magnesium sulfate, and the solvent was removed. The resultant was wet-refined by column-chromatography using hexane and ethylacetate such that compound "b" of dark yellow liquid was obtained. (yield: 81%)

(3) Compound "c"

[Reaction Formula 1-3]

b c

In the $N_2$ gas purging system, compound "b" (38.1 mmol) and tetrahydrofuran solvent was stirred. Methyl magnesium bromide (4.6 equivalent) was slowly dropped in the solution, and the solution was stirred and reacted for 12 hours or more under the room temperature. After completion of the reaction, distilled water was slowly added, and the solution was extracted by ethylacetate. Moisture was removed from the extracted organic layer by using magnesium sulfate, and the solvent was removed. The resultant was wet-refined by column-chromatography using hexane and ethylacetate such that compound "c" of yellow liquid was obtained. (yield: 87%)

(4) Compound "d"

[Reaction Formula 1-4]

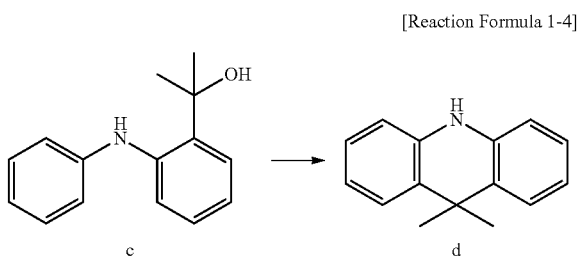 [SMILES: CC(C)(O)c1ccccc1Nc1ccccc1 ; CC1(C)c2ccccc2Nc2ccccc21]

In the N₂ gas purging system, compound "c" (33.1 mmol) was put into excess phosphoric acid solvent (160 ml), and the solution was stirred under the room temperature. The solution was additionally stirred for 16 hours or more, and distilled water (200 to 250 ml) was slowly added. The solution was stirred for 0.5 to 1 hour, and the precipitated solid was filtered. The filtered solid was extracted by using sodium hydroxide aqueous solution and dichloromethane solvent. Moisture was removed from the extracted organic layer by using magnesium sulfate, and the organic solvent was removed such that compound "d" of white solid was obtained. (yield: 69%)

(5) Compound "e"

[Reaction Formula 1-5]

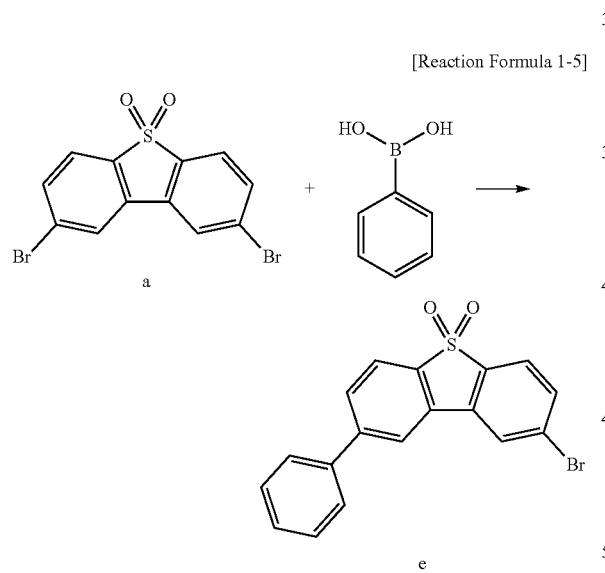

In the N₂ gas purging system, compound "a" (1.0 equivalent) was dissolved in toluene solvent, and phenylboronic acid (0.9 equivalent) was added. K₂CO₃ (4 equivalent) was dissolved in distilled water and added into the mixed solution. Tetrahydrofuran solvent was added, and palladium (0.05 equivalent) was added. The mixture was refluxed and stirred under a temperature of 80° C. After completion of the reaction, the mixture was extracted by using ethylacetate solvent and distilled water, and moisture was removed from the extracted organic layer by using magnesium sulfate. Remained organic solvent was removed, and the resultant was wet-refined by column-chromatography using ethylacetate and hexane such that compound "e" of solid was obtained. (yield: 68%)

(6) Compound 1

[Reaction Formula 1-6]

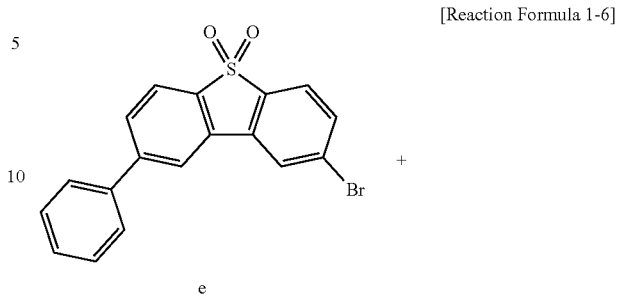

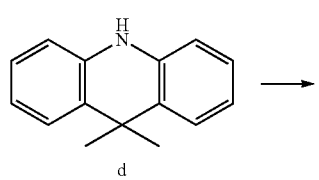

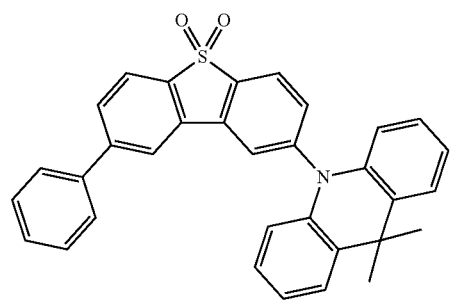

In the N₂ gas purging system, compound "e" (1.0 equivalent), compound "d" (1.1 equivalent), Pd(OAc)₂ (0.019 equivalent), P(t-Bu)₃ (50 wt %, 0.046 equivalent), and sodium tert-butoxide (1.9 equivalent) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 1 was obtained. (yield: 55%)

2. Synthesis of Compound 2

(1) Compound "f"

[Reaction Formula 2-1]

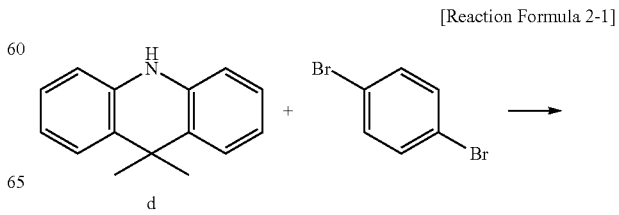

-continued

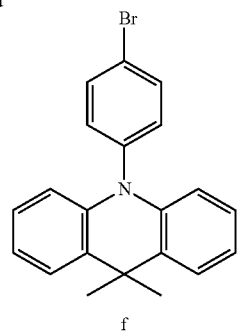

f

In the N₂ gas purging system, compound "d" (23.9 mmol), 1,4-dibromobenzene (35.8 mmol), palladium(II)acetate (2 mol %), tri-tert-butylphosphate (5 mol %), and sodium-tert-butoxide (2.03 equivalent) was added into toluene solvent and stirred. The mixed solution was refluxed and stirred for 12 hours. After completion of the reaction, the solution was extracted by using distilled water and ethylacetate. Moisture was removed from the extracted organic layer by using magnesium sulfate, and the solvent was removed. The resultant was wet-refined by column-chromatography using hexane and ethylacetate such that compound "f" of dark yellow liquid was obtained. (yield: 81%)

(2) Compound "g"

[Reaction Formula 2-2]

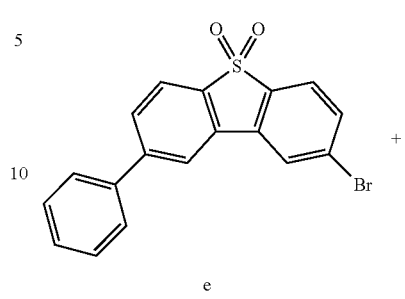

g

In the N₂ gas purging system, compound "f" (1.0 equivalent), bis(pinacolate)diboron (1.2 equivalent), [1,1-bis(diphenylphosphineo)ferrocene]palladium(II), dichloride dichloromethane, 1,1-bis(diphenylphosphino)ferrocene, and potassium acetate were added into 1,4-dioxane/toluene (1:1) solvent in the light-shielded flask and stirred. After bubbles disappeared, the solution was stirred for 17 hours under a temperature of 120° C. After completion of the reaction, the solution was cooled in room temperature, and the solvent was removed. The resultant was washed by toluene and refined such that compound "g" was obtained. (yield: 90%)

(3) Compound 2

[Reaction Formula 2-3]

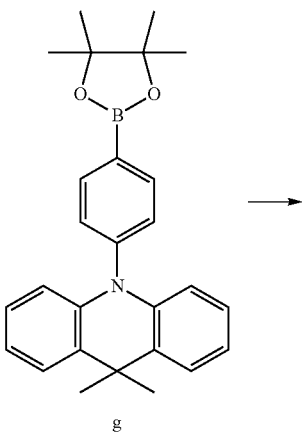

e

+

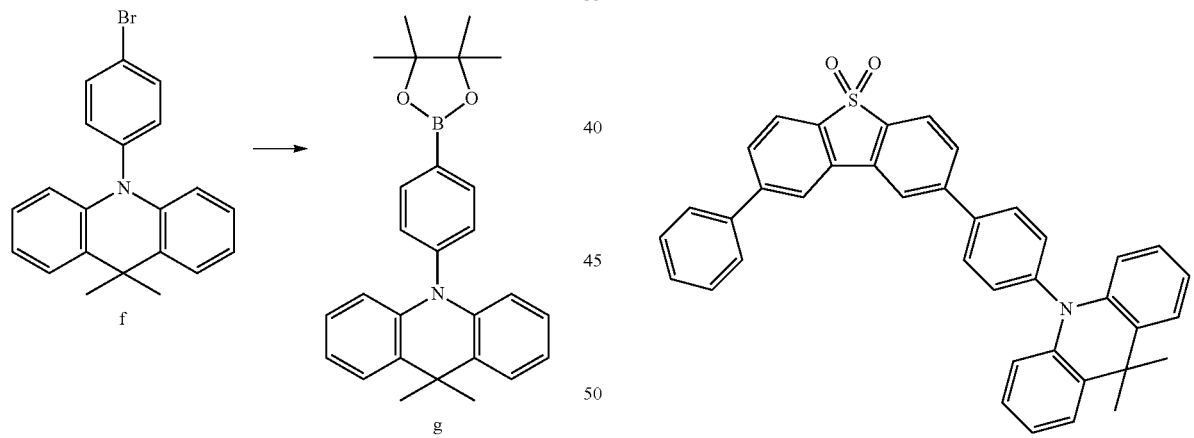

In the N₂ gas purging system, compound "e" (1.0 equivalent) was dissolved in toluene solvent, and compound "g" (1.2 equivalent) was added. K₂CO₃ (8.8 equivalent) was dissolved in distilled water and added into the solution. Tetrahydrofuran solvent was added, and palladium (0.1 equivalent) was added. The mixture was refluxed and stirred under a temperature of 80° C. After completion of the reaction, the mixture was extracted by using sodium hydroxide aqueous solution and toluene. Moisture was removed from the extracted organic layer by using magnesium sulfate, and the remaining organic solvent was removed. The resultant was wet-refined by column-chromatography using hexane and re-crystallized such that compound 2 was obtained. (yield: 56%)

3. Synthesis of Compound 3

(1) Compound "h"

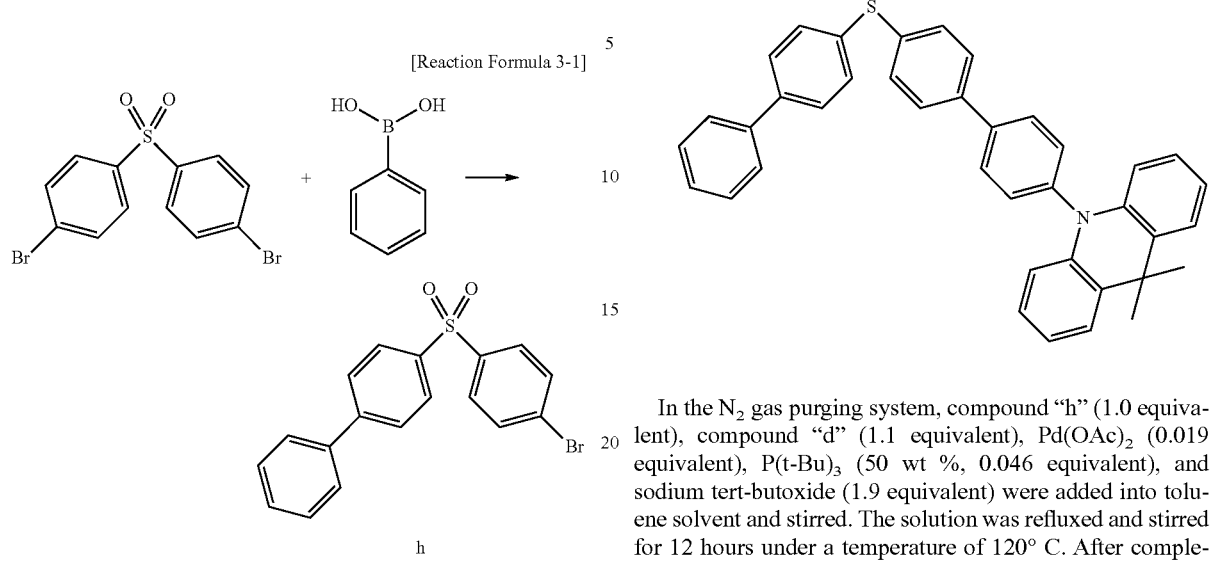

[Reaction Formula 3-1]

In the $N_2$ gas purging system, 4-phenylbromosulfone (1.0 equivalent) was dissolved in toluene solvent, and phenylboronic acid (0.9 equivalent) was added. $K_2CO_3$ (4 equivalent) was dissolved in distilled water and added into the solution. Tetrahydrofuran solvent was added, and palladium (0.05 equivalent) was added. The mixture was refluxed and stirred under a temperature of 80° C. After completion of the reaction, the mixture was extracted by using ethylacetate and distilled water. Moisture was removed from the extracted organic layer by using magnesium sulfate, and remaining organic solvent was removed. The resultant was wet-refined by column-chromatography using ethylacetate and hexane such that compound "h" of solid was obtained. (yield: 75%)

(2) Compound 3

[Reaction Formula 3-2]

In the $N_2$ gas purging system, compound "h" (1.0 equivalent), compound "d" (1.1 equivalent), $Pd(OAc)_2$ (0.019 equivalent), $P(t-Bu)_3$ (50 wt %, 0.046 equivalent), and sodium tert-butoxide (1.9 equivalent) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 3 was obtained. (yield: 65%)

4. Synthesis of Compound 4

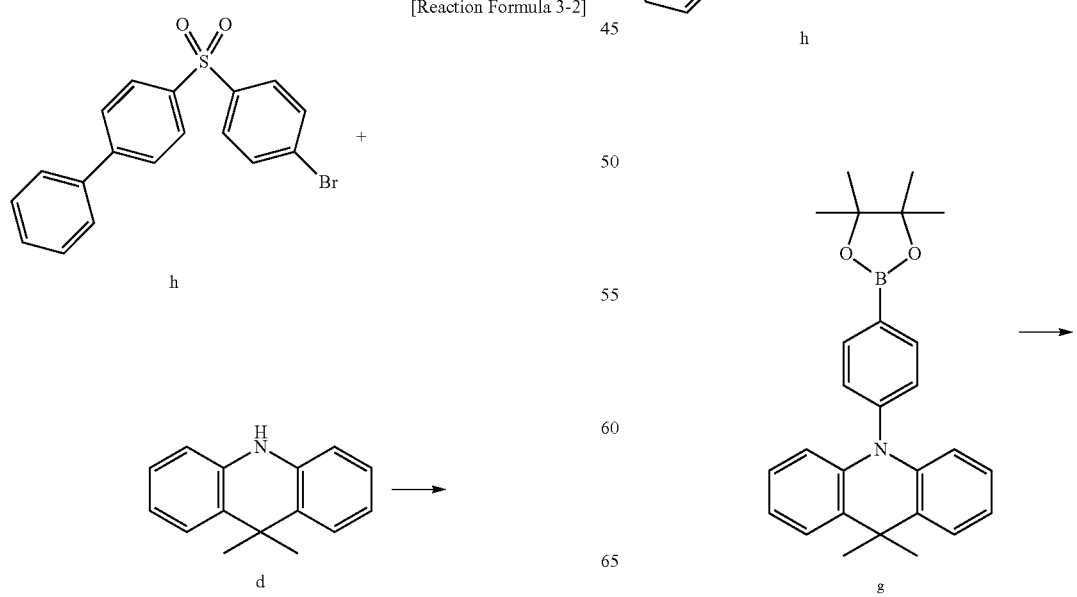

[Reaction Formula 4]

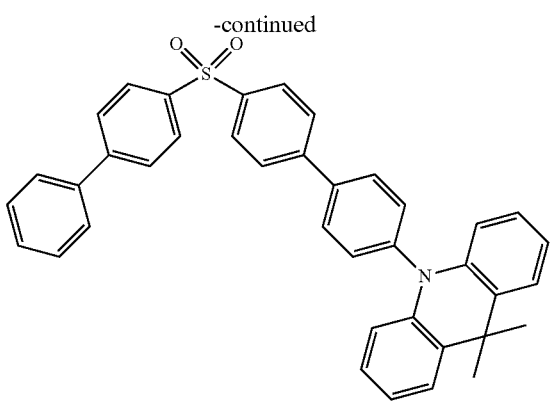

In the N₂ gas purging system, compound "h" (1.0 equivalent) was dissolved in toluene solvent, and compound "g" (1.2 equivalent) was added. K₂CO₃ (8.8 equivalent) was dissolved in distilled water and added into the solution. Tetrahydrofuran solvent was added, and palladium (0.1 equivalent) was added. The mixture was refluxed and stirred under a temperature of 80° C. After completion of the reaction, the mixture was extracted by using sodium hydroxide aqueous solution and toluene. Moisture was removed from the extracted organic layer by using magnesium sulfate, and remained organic solvent was removed. The resultant was wet-refined by column-chromatography using hexane and re-crystallized such that compound 4 was obtained. (yield: 60%)

5. Synthesis of Compound 5

[Reaction Formula 5]

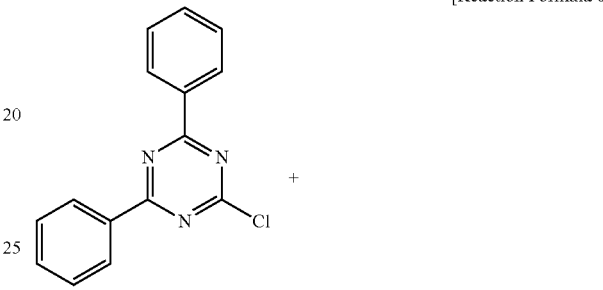

In the N₂ gas purging system, Pd(dba)₂ (5 mol %) as catalyst and P(t-Bu)₃ (4 mol %) was added into toluene solvent and stirred for about 15 minutes. 2-chloro-4,6-diphenyl-1,3,5-triazine (33.8 mmol), compound "d" (33.8 mmol), and NaOt-Bu (60.6 mmol) were additionally added, and the mixture was stirred for 5 hours under a temperature of 90° C. After completion of the reaction, the mixture was filtered by celite, and the solvent was removed. The filtered solid was refined by column-chromatography using hexane and dichloromethane and re-crystallized using hexane such that compound 5 was obtained. (yield: 59%)

6. Synthesis of Compound 6

[Reaction Formula 6]

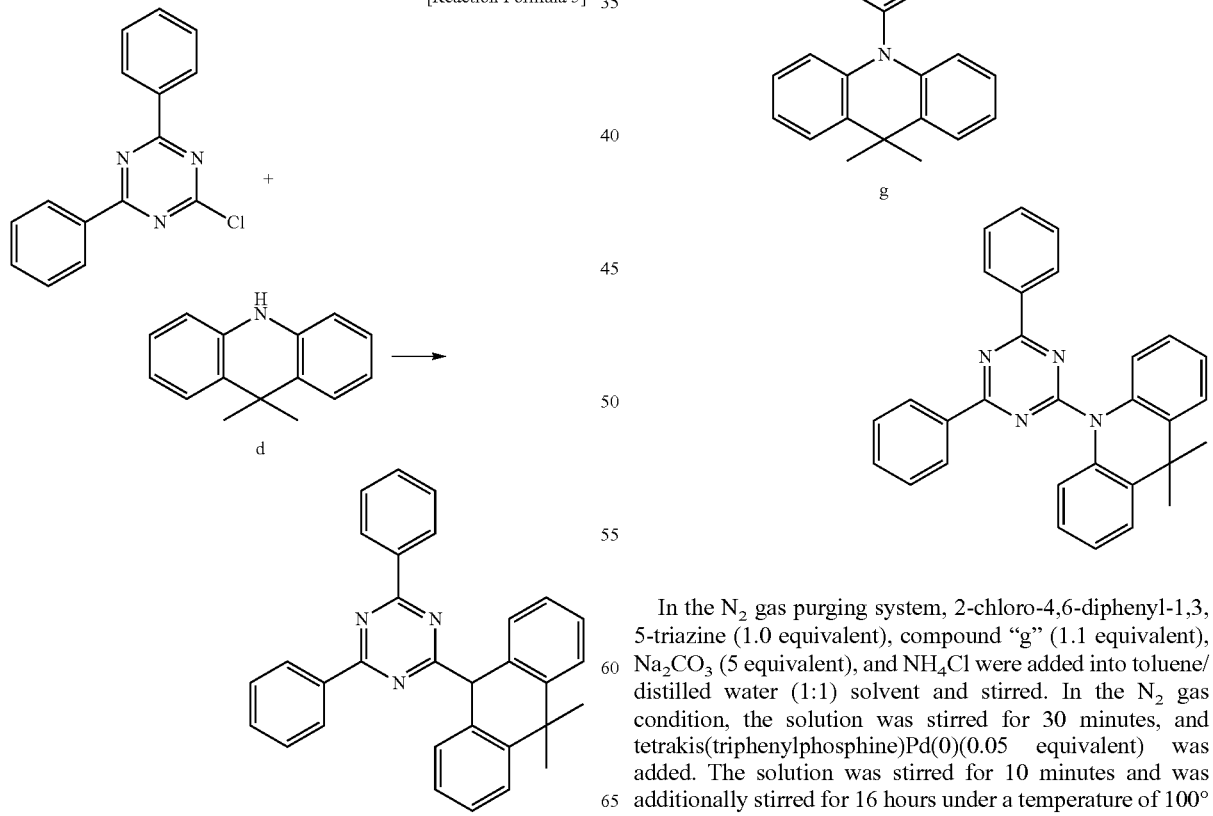

In the N₂ gas purging system, 2-chloro-4,6-diphenyl-1,3,5-triazine (1.0 equivalent), compound "g" (1.1 equivalent), Na₂CO₃ (5 equivalent), and NH₄Cl were added into toluene/distilled water (1:1) solvent and stirred. In the N₂ gas condition, the solution was stirred for 30 minutes, and tetrakis(triphenylphosphine)Pd(0)(0.05 equivalent) was added. The solution was stirred for 10 minutes and was additionally stirred for 16 hours under a temperature of 100° C. After completion of the reaction, the solution was cooled in room temperature and extracted by dichloromethane.

Moisture was removed from the extracted organic layer by using magnesium sulfate, and remaining organic solvent was removed. The resultant was wet-refined by column-chromatography using dichloromethane and hexane and re-crystallized by chloroform such that compound 6 of solid was obtained. (yield: 70%)

7. Synthesis of Compound 7

(1) Compound "i"

[Reaction Formula 7-1]

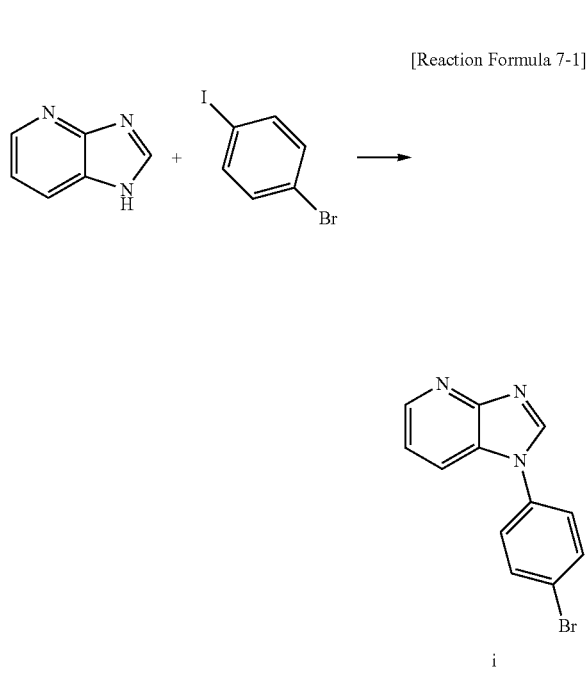

In the N₂ gas purging system, copper iodide (0.1 equivalent) and 1,10-phenanthroline (0.2 equivalent) were added into dimethylformamide (DMF) solvent, and 4-azabenzimidazole, 1-bromo-4-iodobenzene (1.2 equivalent), and cesium carbonate (2 equivalent) were additionally added. The solution was refluxed and stirred for 16 hours under a temperature of 110° C. After completion of the reaction, DMF solvent was removed, and the resultant was extracted by dichloromethane. Moisture was removed from the extracted organic layer by using magnesium sulfate, and the solvent was removed. The resultant was wet-refined by column-chromatography using hexane and ethylacetate and re-crystallization using dichloromethane such that compound "i" was obtained. (yield: 78%)

(2) Compound 7

[Reaction Formula 7-2]

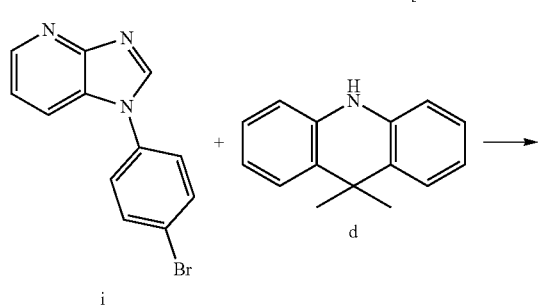

-continued

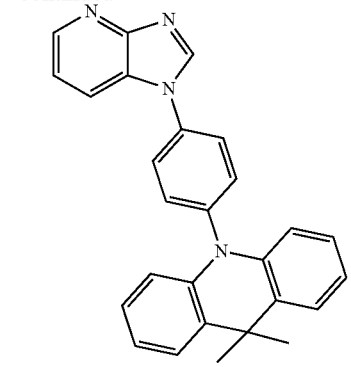

In the N₂ gas purging system, compound "i" (1.0 equivalent), compound "d" (1.1 equivalent), Pd(OAc)₂ (0.019 equivalent), P(t-Bu)₃ (50 wt %, 0.046 equivalent) and sodium tert-butoxide (1.9 equivalent) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 7 was obtained. (yield: 60%)

8. Synthesis of Compound 8

(1) Compound "j"

[Reaction Formula 8-1]

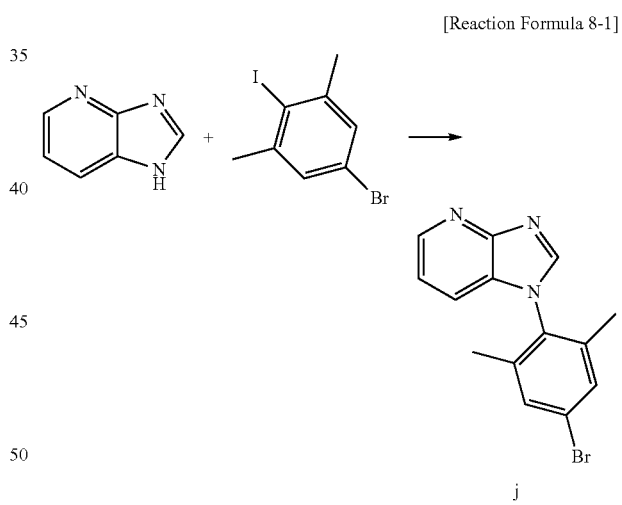

In the N₂ gas purging system, copper iodide (0.1 equivalent) and 1,10-phenanthroline (0.2 equivalent) were added into dimethylformamide (DMF) solvent, and 4-azabenzimidazole, 1-bromo-3,5-dimethyl-4-iodobenzene (1.3 equivalent), and cesium carbonate (2 equivalent) were additionally added. The solution was refluxed and stirred for 16 hours under a temperature of 110° C. After completion of the reaction, DMF solvent was removed, and the resultant was extracted by dichloromethane. Moisture was removed from the extracted organic layer by using magnesium sulfate, and the solvent was removed. The resultant was wet-refined by column-chromatography using hexane and ethylacetate and re-crystallization using dichloromethane such that compound "j" was obtained. (yield: 60%)

(2) Compound 8

[Reaction Formula 8-2]

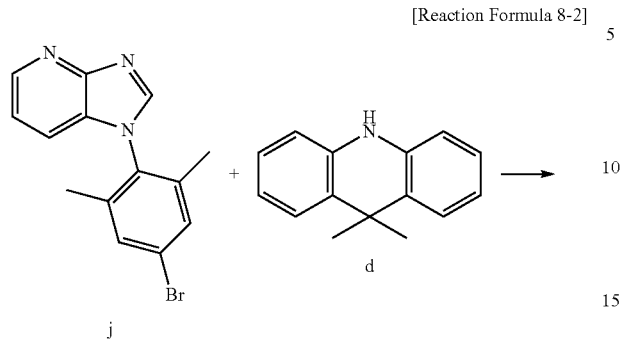

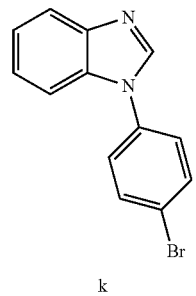

In the N₂ gas purging system, compound 1" (1.0 equivalent), compound "d" (1.1 equivalent), Pd(OAc)₂ (0.019 equivalent), P(t-Bu)₃ (50 wt %, 0.046 equivalent), and sodium tert-butoxide (1.9 equivalent) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 8 was obtained. (yield: 50%)

9. Synthesis of Compound 9

(1) Compound "k"

[Reaction Formula 9-1]

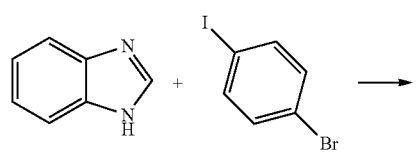

In the N₂ gas purging system, copper iodide (0.1 equivalent) and 1,10-phenanthroline (0.2 equivalent) were added into dimethylformamide (DMF) solvent, and benzimidazole, 1-bromo-4-iodobenzene (1.2 equivalent) and cesium carbonate (2 equivalent) were additionally added. The solution was refluxed and stirred for 16 hours under a temperature of 110° C. After completion of the reaction, DMF solvent was removed, and the resultant was extracted by dichloromethane. Moisture was removed from the extracted organic layer by using magnesium sulfate, and the solvent was removed. The resultant was wet-refined by column-chromatography using hexane and ethylacetate and re-crystallization using dichloromethane such that compound "k" was obtained. (yield: 80%)

(2) Compound 9

[Reaction Formula 9-2]

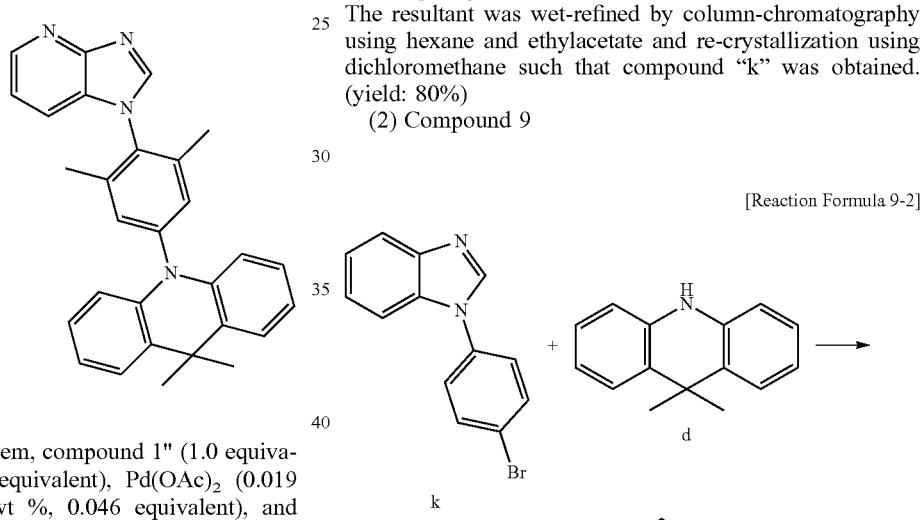

In the N₂ gas purging system, compound "k" (1.0 equivalent), compound "d" (1.1 equivalent), Pd(OAc)₂ (0.019 equivalent), P(t-Bu)₃ (50 wt %, 0.046 equivalent), and sodium tert-butoxide (1.9 equivalent) were added into toluene solvent and stirred. The solution was refluxed and stirred for 12 hours under a temperature of 120° C. After completion of the reaction, the solution was cooled into the room temperature and extracted by water and ethylacetate. Moisture was removed from the extracted organic layer by using magnesium sulfate, and the solvent was removed. The resultant was wet-refined by column-chromatography using hexane and ethylacetate such that compound 9 was obtained. (yield: 62%)

10. Synthesis of Compound 10

(1) Compound "1"

[Reaction Formula 10-1]

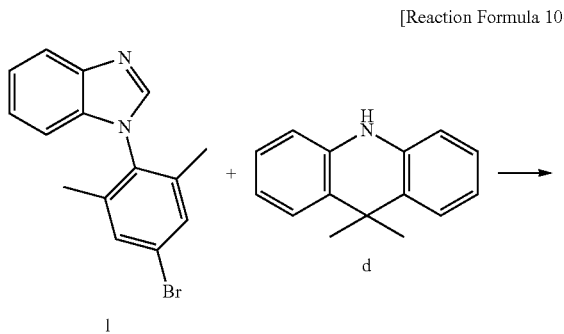

In the N$_2$ gas purging system, copper iodide (0.1 equivalent) and 1,10-phenanthroline (0.2 equivalent) were added into dimethylformamide (DMF) solvent, and benzimidazole, 1-bromo-3,5-dimethyl-4-iodobenzene (1.3 equivalent) and cesium carbonate (2 equivalent) were additionally added. The solution was refluxed and stirred for 16 hours under a temperature of 110° C. After completion of the reaction, DMF solvent was removed, and the resultant was extracted by dichloromethane. Moisture was removed from the extracted organic layer by using magnesium sulfate, and the solvent was removed. The resultant was wet-refined by column-chromatography using hexane and ethylacetate and re-crystallization using dichloromethane such that compound "1" was obtained. (yield: 58%)

(2) Compound 10

[Reaction Formula 10-2]

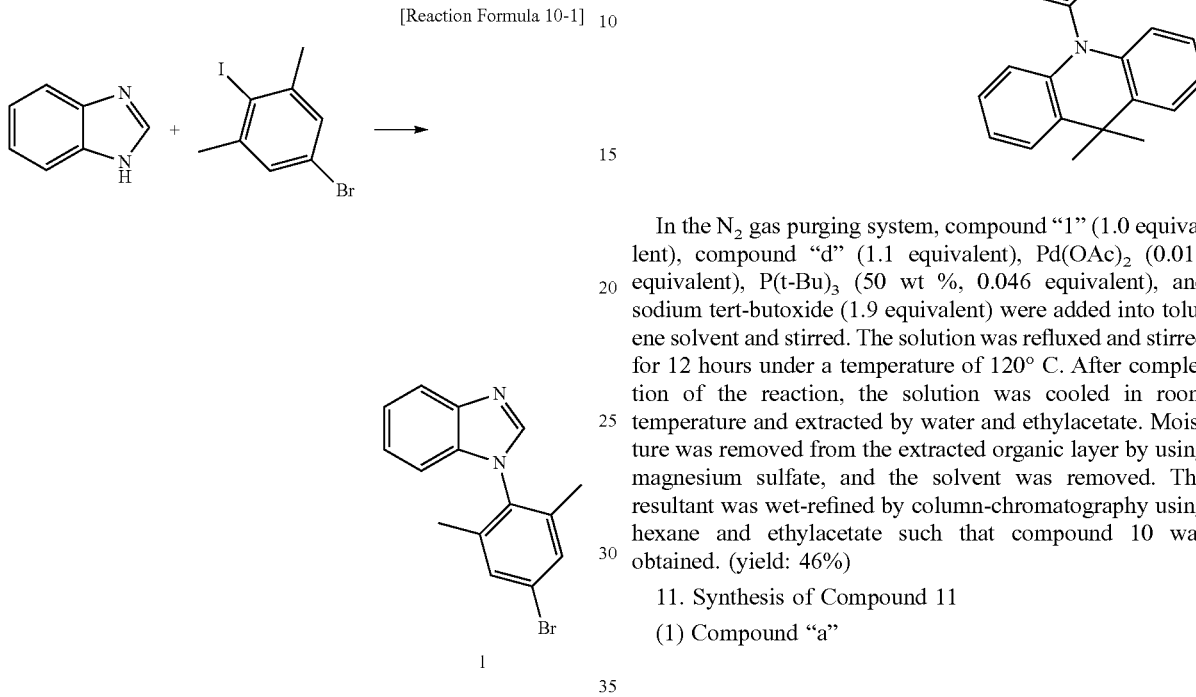

In the N$_2$ gas purging system, compound "1" (1.0 equivalent), compound "d" (1.1 equivalent), Pd(OAc)$_2$ (0.019 equivalent), P(t-Bu)$_3$ (50 wt %, 0.046 equivalent), and sodium tert-butoxide (1.9 equivalent) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 10 was obtained. (yield: 46%)

11. Synthesis of Compound 11

(1) Compound "a"

[Reaction Formula 11-1]

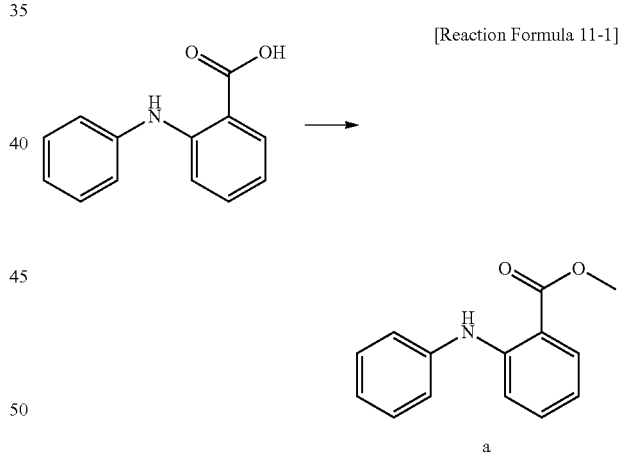

In the N$_2$ gas purging system, N-phenylanthraniliic acid (46.9 mmol) was added into methanol solvent and stirred. The mixture was additionally stirred for 10 minutes under a temperature of 0° C., and thionyl chloride (21.2 mmol) was slowly dropped. The mixed solution was stirred for 12 hours or more under a temperature of 90° C. After completion of the reaction, the solvent was removed, and the mixed solution was extracted by distilled water and ethylacetate. Moisture was removed from the extracted organic layer by using magnesium sulfate, and the solvent was removed. The resultant was wet-refined by column-chromatography using hexane and ethylacetate such that compound "a" of dark yellow liquid was obtained. (yield: 81%)

(2) Compound "b"

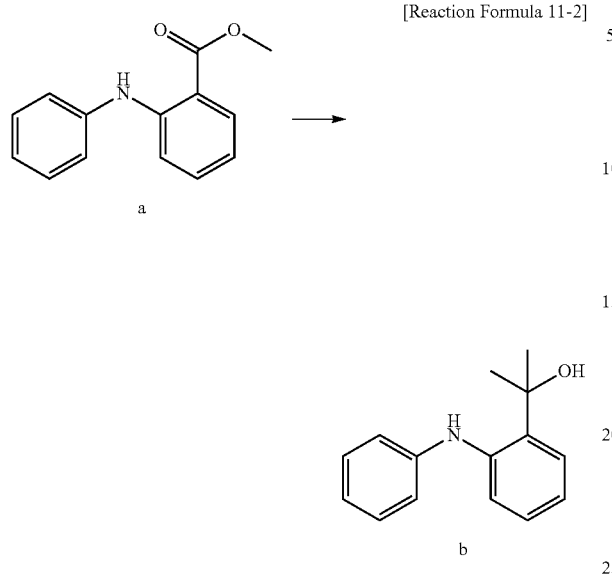

[Reaction Formula 11-2]

In the N₂ gas purging system, compound "a" (38.1 mmol) and tetrahydrofuran solvent was stirred. Methyl magnesium bromide (4.6 equivalent) was slowly dropped in the solution, and the solution was stirred and reacted for 12 hours or more under room temperature. After completion of the reaction, distilled water was slowly added, and the solution was extracted by ethylacetate. Moisture was removed from the extracted organic layer by using magnesium sulfate, and the solvent was removed. The resultant was wet-refined by column-chromatography using hexane and ethylacetate such that compound "b" of yellow liquid was obtained. (yield: 87%)

(3) Compound "c"

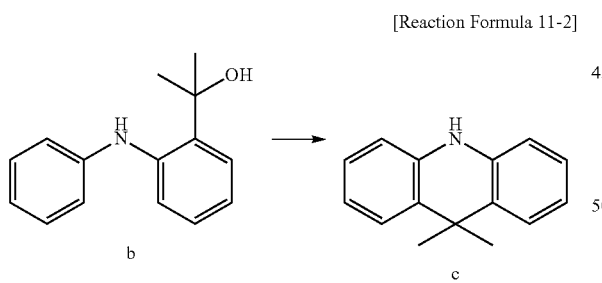

[Reaction Formula 11-2]

In the N₂ gas purging system, compound "b" (33.1 mmol) was put into excess phosphoric acid solvent (160 ml), and the solution was stirred under room temperature. The solution was additionally stirred for 16 hour or more, and distilled water (200 to 250 ml) was slowly added. The solution was stirred for 0.5 to 1 hour, and the precipitated solid was filtered. The filtered solid was extracted by using sodium hydroxide aqueous solution and dichloromethane solvent. Moisture was removed from the extracted organic layer by using magnesium sulfate, and the organic solvent was removed such that compound "c" of white solid was obtained. (yield: 69%)

(4) Compound "d"

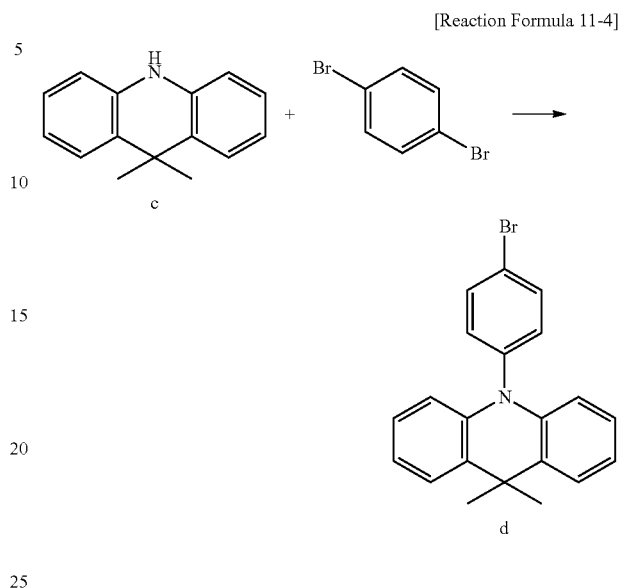

[Reaction Formula 11-4]

In the N₂ gas purging system, compound "c" (23.9 mmol), 1,4-dibromobenzene (35.8 mmol), palladium(II)acetate (2 mol %), tri-tert-butylphosphate (5 mol %) and sodium-tert-butoxide (2.03 equivalent) was added into toluene solvent and stirred. The mixed solution was refluxed and stirred for 12 hours. After completion of the reaction, the solution was extracted by using distilled water and ethylacetate. Moisture was removed from the extracted organic layer by using magnesium sulfate, and the solvent was removed. The resultant was wet-refined by column-chromatography using hexane and ethylacetate such that compound "d" was obtained. (yield: 81%)

(5) Compound "e"

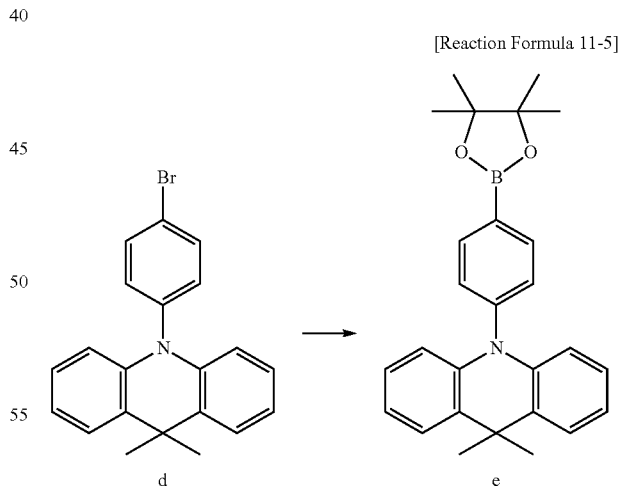

[Reaction Formula 11-5]

In the N₂ gas purging system, compound "d", bis(pinacolate)diboron (1.2 equivalent), [1,1-bis(diphenylphosphineo)ferrocene]palladium(II), dichloride dichloromethane, 1,1-bis(diphenylphosphino)ferrocene, and potassium acetate were added into 1,4-dioxane/toluene (1:1) solvent in the light-shielded flask and stirred. After bubbles were disappeared, the solution was stirred for 17 hours under a temperature of 120° C. After completion of the reaction, the solution was cooled into the room temperature, and the solvent was removed. The resultant was washed by toluene and refined such that compound "e" was obtained. (yield: 90%)

(6) Compound "f"

[Reaction Formula 11-6]

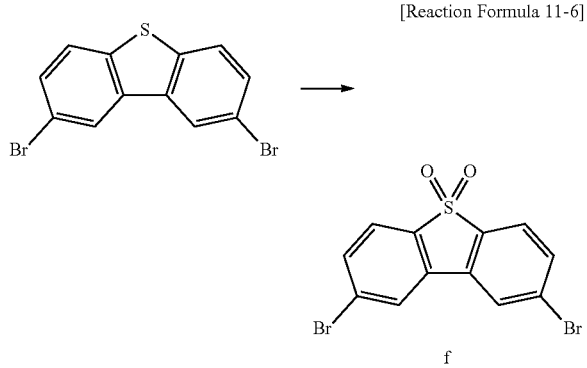 [SMILES: Brc1ccc2sc3ccc(Br)cc3c2c1 ; O=S1(=O)c2ccc(Br)cc2-c2cc(Br)ccc21]

f

In the N₂ gas purging system, 2,8-dibromodibenzothiophene (14.6 mmol) and acetic acid solvent were mixed and stirred. Hydrogen peroxide (64.8 mmol) was added and stirred in room temperature for about 30 minutes, and the mixture were refluxed and stirred for 12 hours or more. After completion of the reaction, distilled water (50 ml) was added and stirred to wash. After filtering the mixture, the solids was mixed with excess hydrogen peroxide and stirred to wash for 30 to 60 minutes. The solids was washed by distilled water and filtered and dried such that compound "f" in white solid was obtained. (yield: 90%)

(7) Compound 11

[Reaction Formula 11-7]

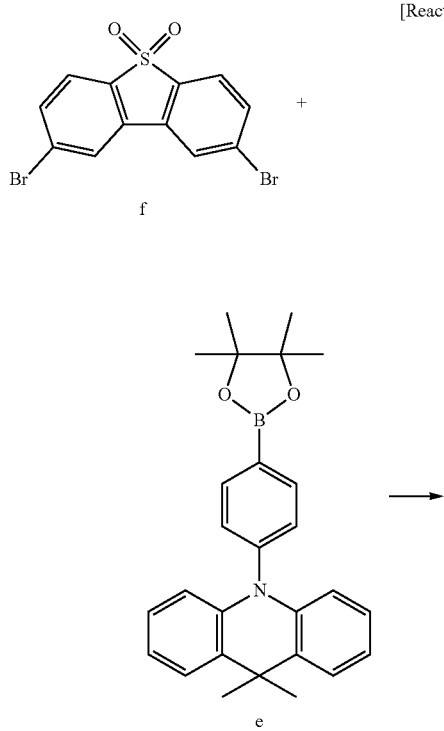

-continued

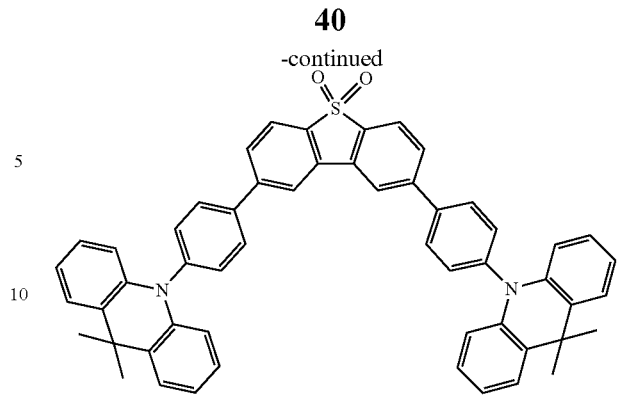

In the N₂ gas purging system, compound "f" (1.0 equivalent) was dissolved in toluene solvent, and compound "e" (2.4 equivalent) was added. $K_2CO_3$ (8.8 equivalent) was dissolved in distilled water and added into the solution. Tetrahydrofuran solvent was added, and palladium (0.1 equivalent) was added. The mixture was refluxed and stirred under a temperature of 80° C. After completion of the reaction, the mixture was extracted by using sodium hydroxide aqueous solution and toluene. Moisture was removed from the extracted organic layer by using magnesium sulfate, and remained organic solvent was removed. The resultant was wet-refined by column-chromatography using hexane and re-crystallized such that compound 11 was obtained. (yield: 85%)

12. Synthesis of Compound 12

(1) Compound "g"

[Reaction Formula 12-1]

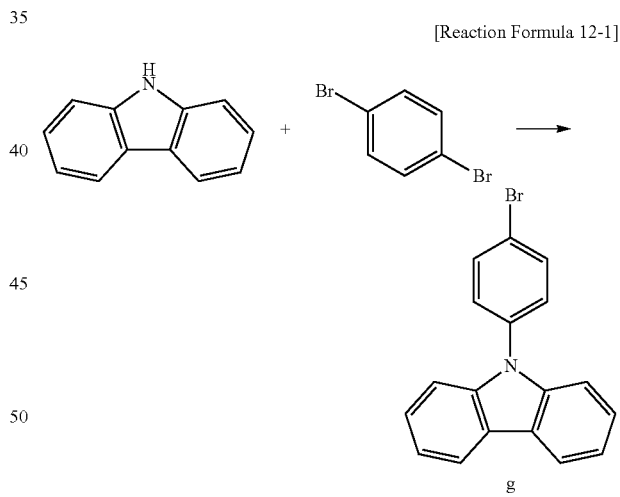

g

In the N₂ gas purging system, carbazole (29.9 mmol), 1,4-dibromobenzene (44.9 mmol), palladium(II)acetate (2 mol %), tri-tert-butylphosphate (5 mol %) and sodium-tert-butoxide (2.03 equivalent) was added into toluene solvent and stirred. The mixed solution was refluxed and stirred for 12 hours. After completion of the reaction, the solution was extracted by using distilled water and ethylacetate. Moisture was removed from the extracted organic layer by using magnesium sulfate, and the solvent was removed. The resultant was wet-refined by column-chromatography using hexane and ethylacetate such that compound "g" was obtained. (yield: 80%)

(2) Compound "h"

[Reaction Formula 12-2]

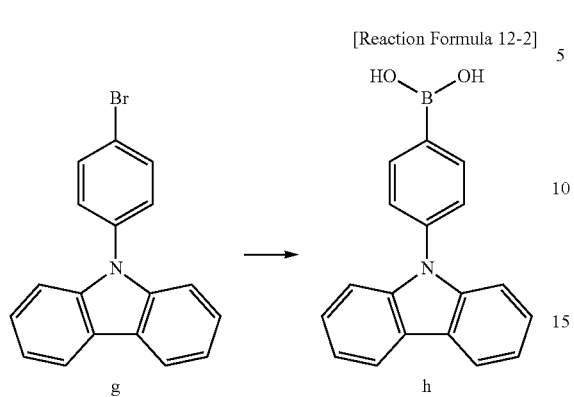

In the N₂ gas purging system, compound "g" was dissolved in tetrahydrofuran and stirred. n-butyl-lithium (26.9 mmol) was slowly added into the solution under a temperature of −78° C., and the mixed solution was stirred for 1 hour. With maintaining the low temperature condition, triethylborate (21.6 mmol) was added, and the mixed solution was stirred under room temperature. The mixed solution was stirred for 12 hours under room temperature, and the reaction was completed. Distilled water was slowly added, and a mixed solution of distilled water/hydrochloric acid (8:2) was added to be pH 2. The solution was extracted using distilled water and ethylacetate. Moisture was removed from the extracted organic layer by using magnesium sulfate, and the solvent was removed. The resultant was wet-refined by column-chromatography using hexane and ethylacetate such that compound "h" was obtained. (yield: 87%)

(3) Compound "i"

[Reaction Formula 12-3]

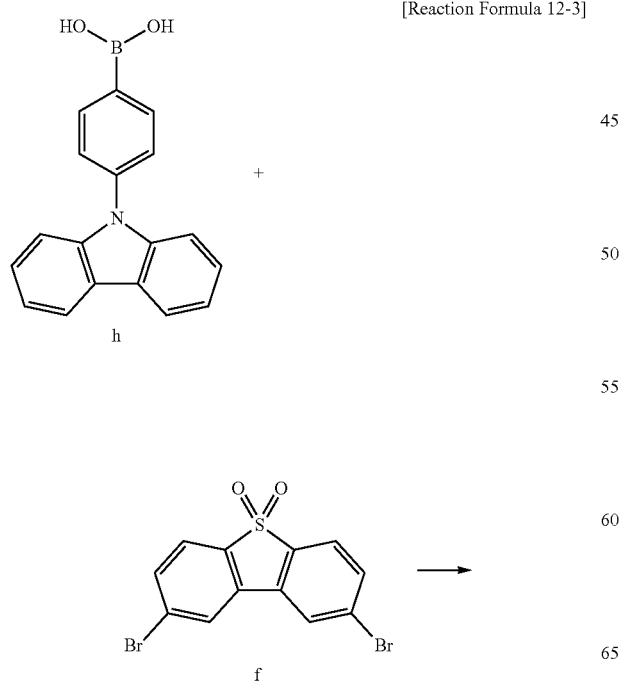

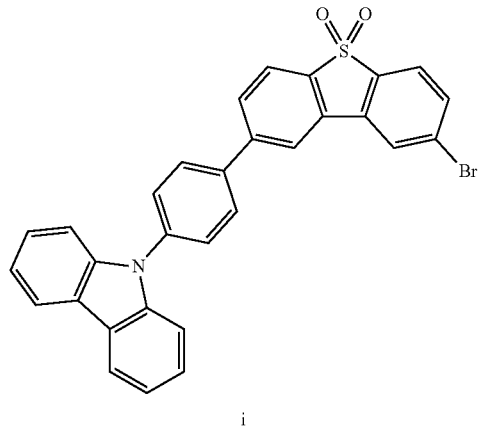

In the N₂ gas purging system, compound "f" (1.0 equivalent) was dissolved in toluene solvent, and compound "h" (0.9 equivalent) was added. K₂CO₃ (4 equivalent) was dissolved in distilled water and added into the solution. Tetrahydrofuran solvent was added, and palladium (0.05 equivalent) was added. The mixture was refluxed and stirred under a temperature of 80° C. After completion of the reaction, the mixture was extracted by using ethylacetate and distilled water. Moisture was removed from the extracted organic layer by using magnesium sulfate, and remaining organic solvent was removed. The resultant was wet-refined by column-chromatography using ethylacetate and hexane such that compound "i" of solid was obtained. (yield: 65%)

(4) Compound 12

[Reaction Formula 12-4]

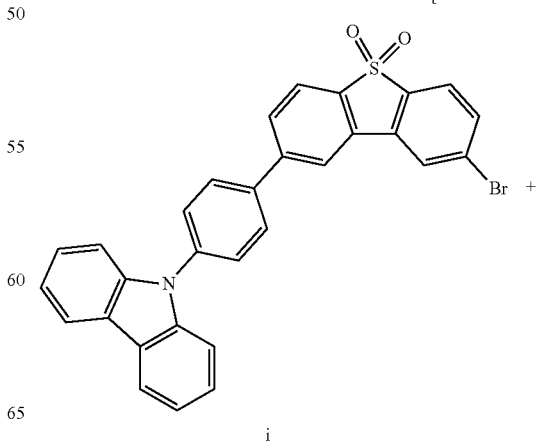

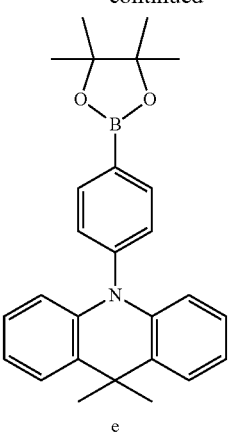

e

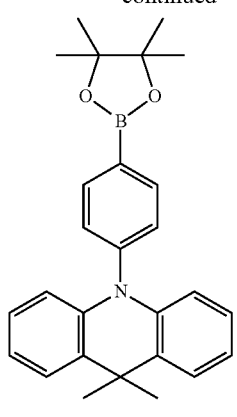

e

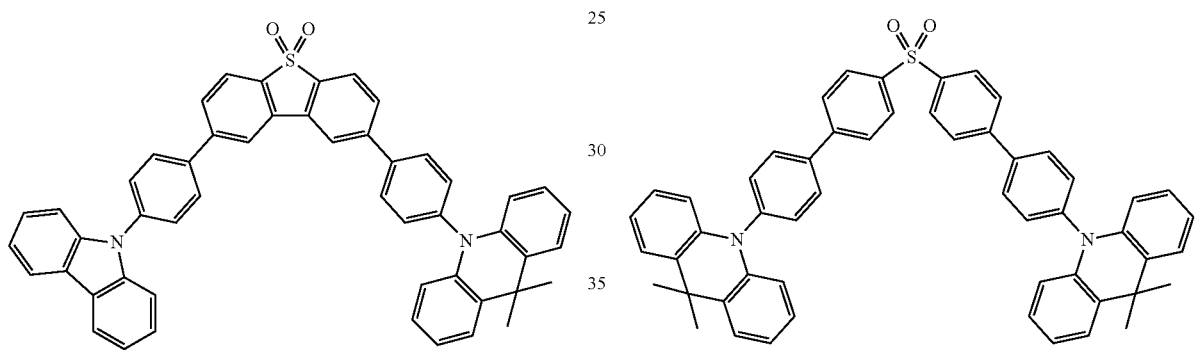

In the N₂ gas purging system, compound "i" (1.0 equivalent) was dissolved in toluene solvent, and compound "e" (1.2 equivalent) was added. K₂CO₃ (8.8 equivalent) was dissolved in distilled water and added into the solution. Tetrahydrofuran solvent was added, and palladium (0.1 equivalent) was added. The mixture was refluxed and stirred under a temperature of 80° C. After completion of the reaction, the mixture was extracted by using sodium hydroxide aqueous solution and toluene. Moisture was removed from the extracted organic layer by using magnesium sulfate, and remained organic solvent was removed. The resultant was wet-refined by column-chromatography using hexane and re-crystallized such that compound 12 was obtained. (yield: 75%)

13. Synthesis of Compound 13

[Reaction Formula 13]

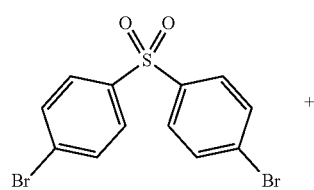

+

In the N₂ gas purging system, 4-bromophenylsulfone (1.0 equivalent) was dissolved in toluene solvent, and compound "e" (2.4 equivalent) was added. K₂CO₃ (8.8 equivalent) was dissolved in distilled water and added into the solution. Tetrahydrofuran solvent was added, and palladium (0.1 equivalent) was added. The mixture was refluxed and stirred under a temperature of 80° C. After completion of the reaction, the mixture was extracted by using sodium hydroxide aqueous solution and toluene. Moisture was removed from the extracted organic layer by using magnesium sulfate, and remained organic solvent was removed. The resultant was wet-refined by column-chromatography using hexane and re-crystallized such that compound 13 was obtained. (yield: 78%)

14. Synthesis of Compound 14

(1) Compound "j"

[Reaction Formula 14-1]

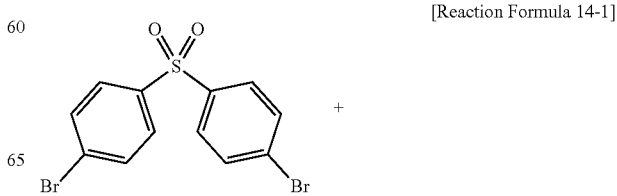

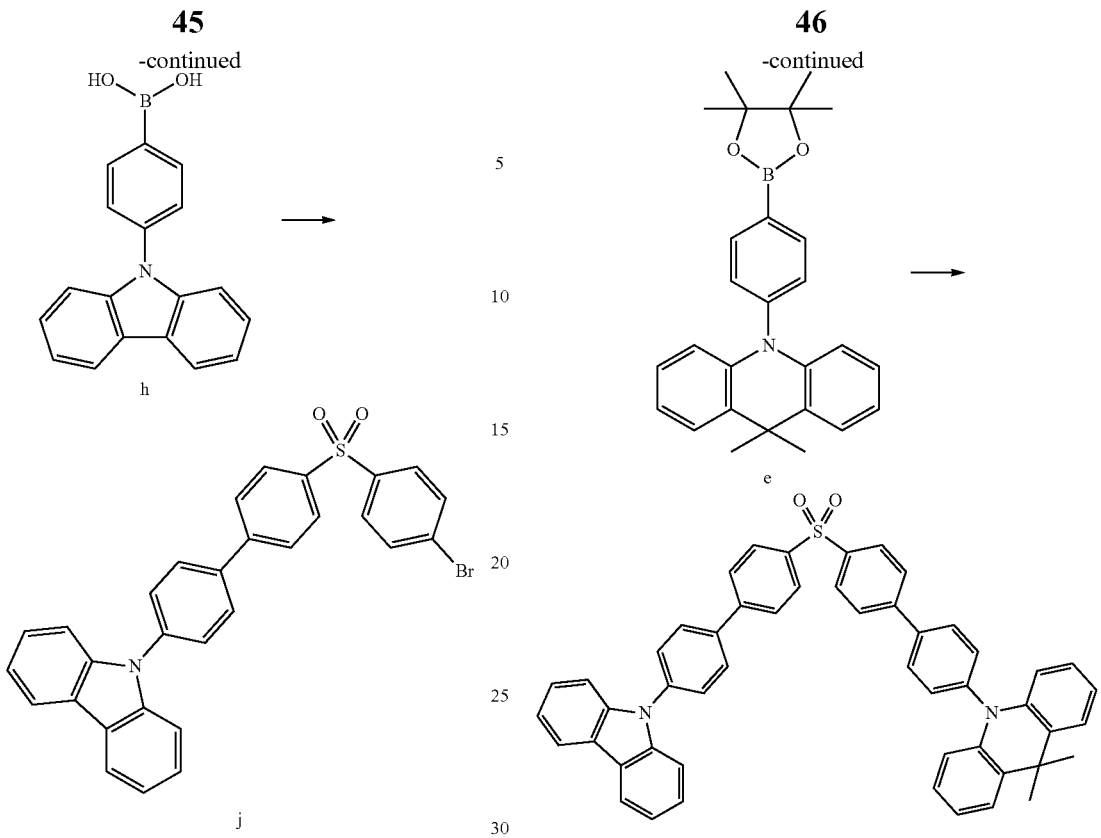

In the N₂ gas purging system, 4-bromophenylsulfone (1.0 equivalent) was dissolved in toluene solvent, and compound "h" (0.9 equivalent) was added. K₂CO₃ (4 equivalent) was dissolved in distilled water and added into the solution. Tetrahydrofuran solvent was added, and palladium (0.05 equivalent) was added. The mixture was refluxed and stirred under a temperature of 80° C. After completion of the reaction, the mixture was extracted by using ethylacetate and distilled water. Moisture was removed from the extracted organic layer by using magnesium sulfate, and remained organic solvent was removed. The resultant was wet-refined by column-chromatography using ethylacetate and hexane such that compound "j" of solid was obtained. (yield: 60%)

(2) Compound 14

In the N₂ gas purging system, compound "j" (1.0 equivalent) was dissolved in toluene solvent, and compound "e" (1.2 equivalent) was added. K₂CO₃ (8.8 equivalent) was dissolved in distilled water and added into the solution. Tetrahydrofuran solvent was added, and palladium (0.1 equivalent) was added. The mixture was refluxed and stirred under a temperature of 80° C. After completion of the reaction, the mixture was extracted by using sodium hydroxide aqueous solution and toluene. Moisture was removed from the extracted organic layer by using magnesium sulfate, and remaining organic solvent was removed. The resultant was wet-refined by column-chromatography using hexane and re-crystallized such that compound 14 was obtained. (yield: 55%)

15. Synthesis of Compound 15

(1) Compound "k"

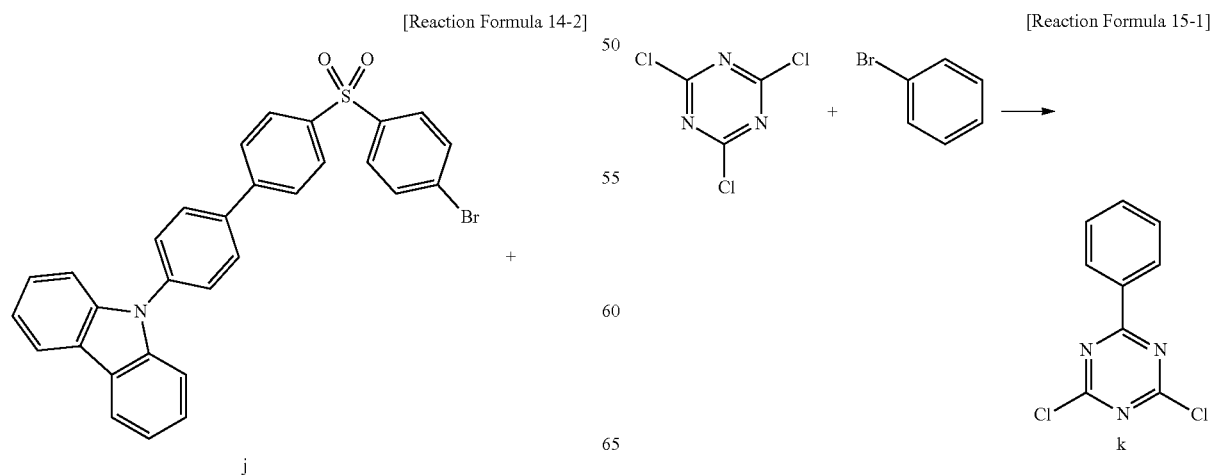

In the light-shielded flask of the N₂ gas purging system, bromobenzene (0.9 equivalent) was dissolved in tetrahydrofuran under a temperature of −78° C., and n-butyl-lithium was slowly dropped. 2,4,6-trichloro-1,3,5-triazine dissolved in tetrahydrofuran was dropped into the solution using cannula in the N₂ condition and was stirred for 8 hours. After completion of the reaction, the resultant was refined such that compound "k" was obtained. (yield: 45%)

(2) Compound 15

[Reaction Formula 15-2]

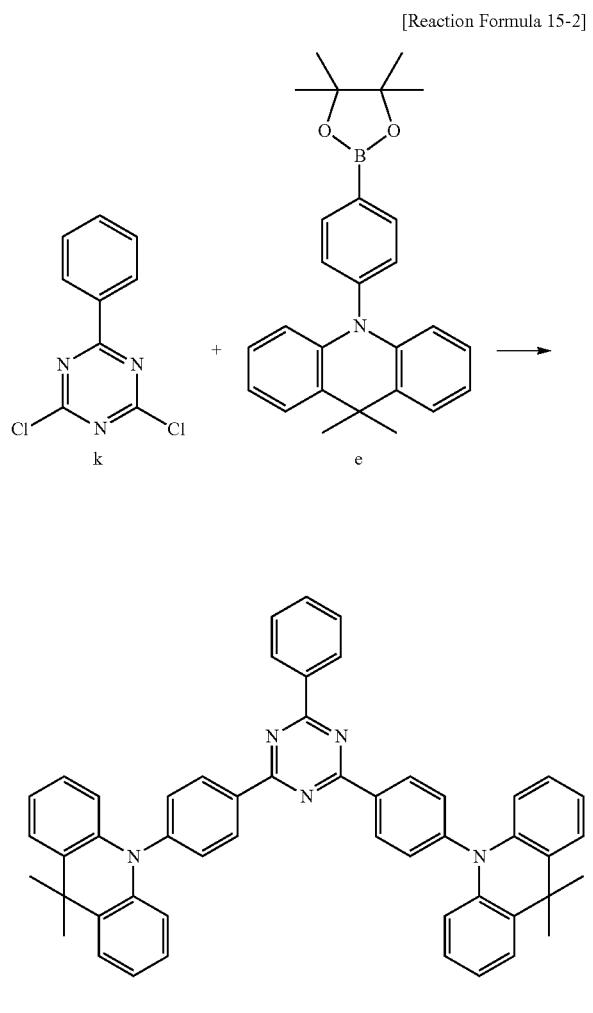

In the N₂ gas purging system, compound "k" (1.0 equivalent), compound "e" (2.1 equivalent), Na₂CO₃ (5 equivalent) and NH₄Cl (0.2 equivalent) were added into solvent of toluene/distilled water (1:1) and stirred. The solution was stirred for 30 minutes in the N₂ condition, tetrakis(triphenylphosphine)palladium(0) (0.05 equivalent) was additionally added and stirred for 10 minutes. The mixture was stirred for 16 hours under a temperature of 100° C. After completion of the reaction, the solution was cooled in room temperature and extracted by dichloromethane and distilled water. Moisture was removed from the extracted organic layer by using magnesium sulfate, and the solvent was removed. The resultant was wet-refined by column-chromatography using dichloromethane and hexane and re-crystallized by using chloroform and acetonitrile such that compound 15 was obtained. (yield: 75%)

16. Synthesis of Compound 16

(1) Compound "1"

[Reaction Formula 16-1]

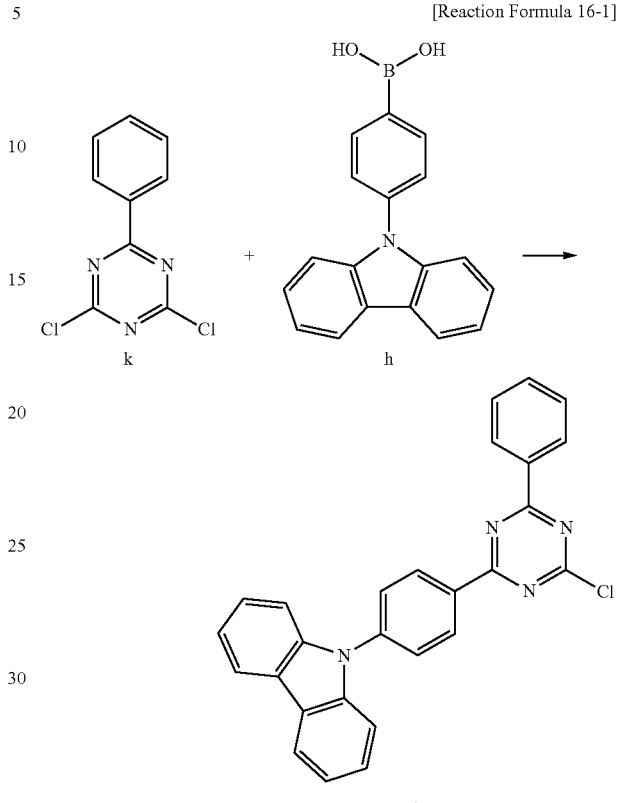

In the N₂ gas purging system, compound "k" (1.0 equivalent), compound "h" (0.9 equivalent) and Na₂CO₃ (0.6 equivalent) were put into solvent of toluene/dioxane/distilled water (1:1:0.7) and stirred. Pd(PPh₃)₄ (tetrakis(triphenylphosphine)palladium(0), 0.3 equivalent) was additionally added and stirred for 16 hours. After completion of the reaction, the solution was cooled in room temperature. The organic layer was washed and filtered by distilled water in silica-gel. The solvent and distilled water were removed, and the resultant was re-crystallized by chloroform and dried such that compound "1" was obtained. (yield: 80%)

(2) Compound 16

[Reaction Formula 16-2]

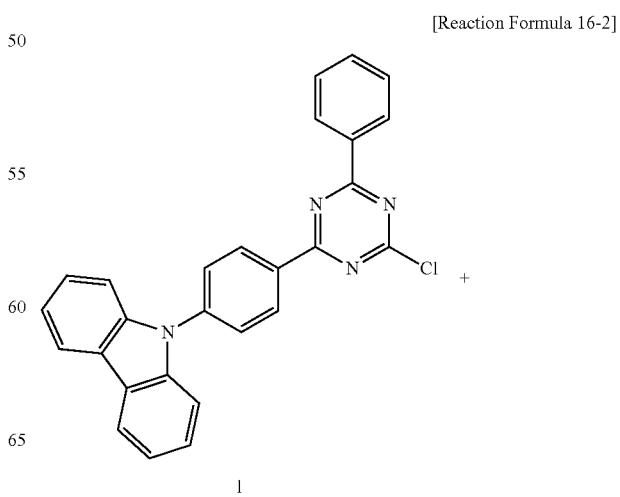

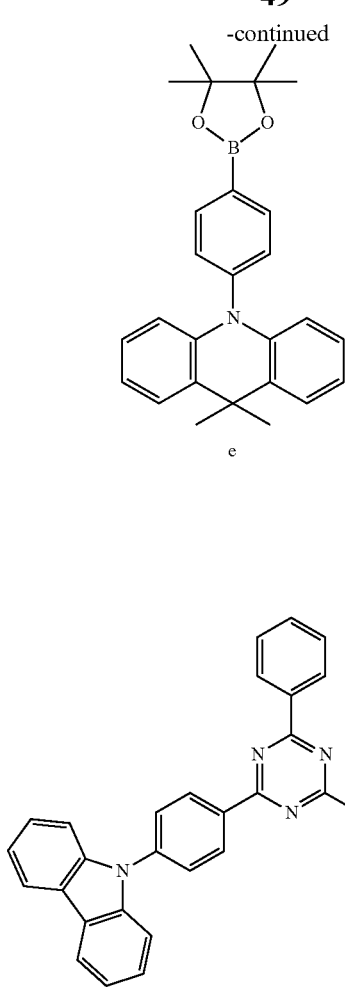

e

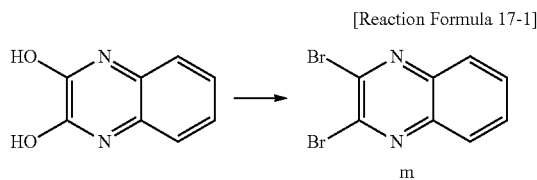 [SMILES: Oc1nc2ccccc2nc1O ; Brc1nc2ccccc2nc1Br]

In the N₂ gas purging system, compound "1" (1.0 equivalent), compound "e" (1.05 equivalent), Na₂CO₃ (5 equivalent) and NH₄Cl (0.2 equivalent) were added into solvent of toluene/distilled water (1:1) and stirred. The solution was stirred for 30 minutes in the N₂ condition, tetrakis(triphenylphosphine)palladium(0) (0.05 equivalent) was additionally added and stirred for 10 minutes. The mixture was stirred for 16 hours under a temperature of 100° C. After completion of the reaction, the solution was cooled into the room temperature and extracted by dichloromethane and distilled water. Moisture was removed from the extracted organic layer by using magnesium sulfate, and the solvent was removed. The resultant was wet-refined by column-chromatography using dichloromethane and hexane and re-crystallized by using chloroform and acetonitrile such that compound 16 was obtained. (yield: 60%)

17. Synthesis of Compound 17

(1) Compound "m"

[Reaction Formula 17-1]

In the N₂ gas purging system, 2,3-hydroquinoxaline (3 g) was put into PBr₅ solvent and stirred for 4 hours under a temperature of 160° C. After completion of the reaction, the solution was cooled into 0° C. and stirred for 30 minutes. The mixture was extracted by dichloromethane and distilled water and washed by 1N sodium hydroxide. Moisture was removed by using magnesium sulfate, and the resultant was enriched such that compound "m" was obtained. (yield: 96%)

(2) Compound 17

[Reaction Formula 17-2]

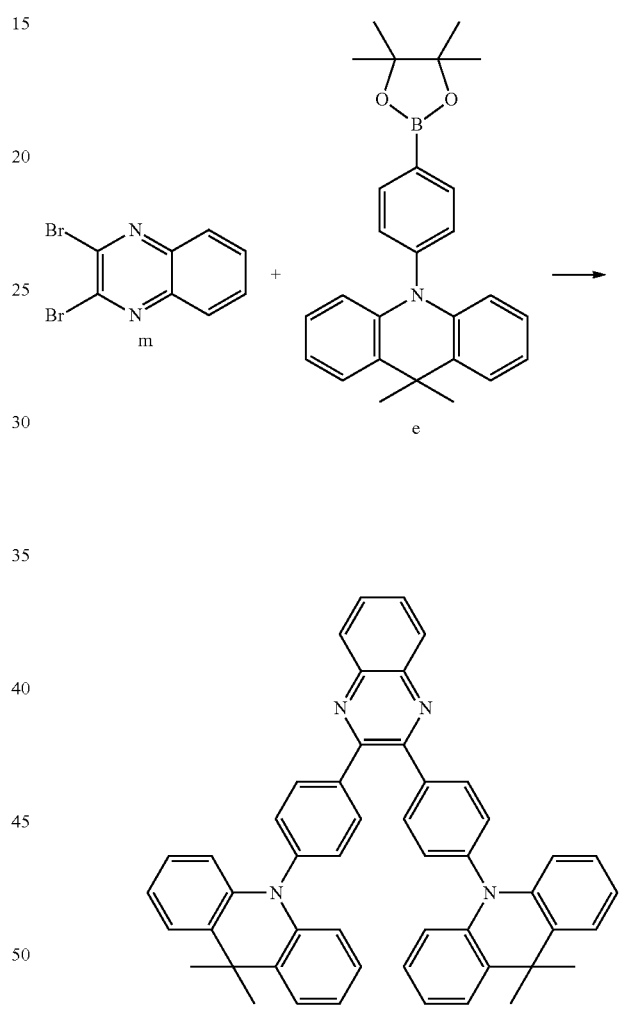

Compound "m" (1.0 equivalent), compound "e" (3 equivalent), Pd₂(dba)₃ (0.1 equivalent), tri-cyclohexylphosphine (0.1 equivalent) and 1.35M K₃PO₄ aqueous solution were put into dioxane solvent and stirred. In the N₂ gas purging system, the mixture was refluxed and stirred for 48 hours. After completion of the reaction, the solution was cooled into the room temperature and extracted by dichloromethane and distilled water. Moisture was removed from the extracted organic layer by using magnesium sulfate, and the solvent was removed. The resultant was wet-refined by column-chromatography using dichloromethane and hexane and re-crystallization such that compound 17 was obtained. (yield: 36%)

18. Synthesis of Compound 18
(1) Compound "n"

(2) Compound 18

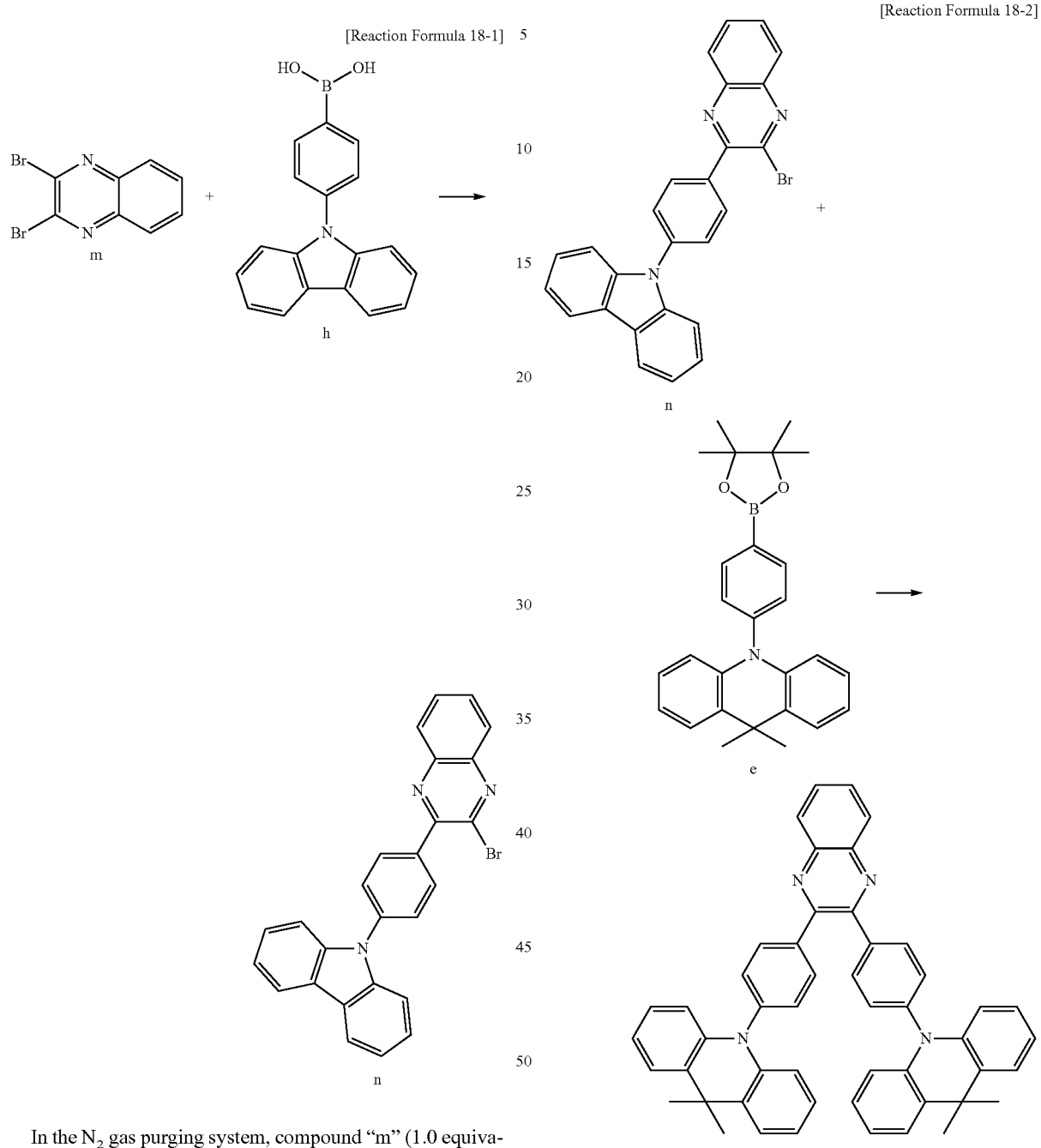

[Reaction Formula 18-1]

[Reaction Formula 18-2]

In the $N_2$ gas purging system, compound "m" (1.0 equivalent) was dissolved in toluene solvent, and compound "h" (0.9 equivalent) was added into the solution. $K_2CO_3$ (4 equivalent) was dissolved in distilled water and added into the mixed solution. Tetrahydrofuran solvent was added, and palladium (0.05 equivalent) was added. The mixture was refluxed and stirred under a temperature of 80° C. After completion of the reaction, the mixture was extracted by using ethylacetate solvent and distilled water, and moisture was removed from the extracted organic layer by using magnesium sulfate. Remaining organic solvent was removed, and the resultant was wet-refined by column-chromatography using ethylacetate and hexane such that compound "n" of solid was obtained. (yield: 55%)

In the $N_2$ gas purging system, compound "n" (1.0 equivalent) was dissolved in toluene solvent, and compound "e" (1.2 equivalent) was added into the solution. $K_2CO_3$ (8.8 equivalent) was dissolved in distilled water and added into the mixed solution. Tetrahydrofuran solvent was added, and palladium (0.1 equivalent) was added. The mixture was refluxed and stirred under a temperature of 80° C. After completion of the reaction, the mixture was extracted by using sodium hydroxide aqueous solution and toluene. Moisture was removed from the extracted organic layer by using magnesium sulfate, and remained organic solvent was removed. The resultant was wet-refined by column-chromatography using hexane and re-crystallized such that compound 18 was obtained. (yield: 45%)

19. Synthesis of Compound 19

(1) Compound "a"

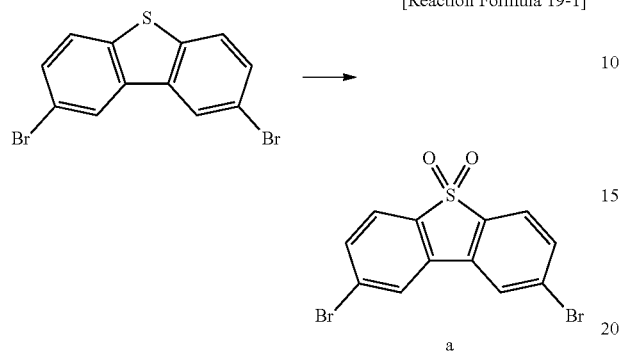

[Reaction Formula 19-1]

a

In the N$_2$ gas purging system, 2,8-dibromodibenzothiophene (14.6 mmol) and acetic acid solvent were mixed and stirred. Hydrogen peroxide (64.8 mmol) was added and stirred in the room temperature for about 30 minutes, and the mixture were refluxed and stirred for 12 hours or more. After completion of the reaction, distilled water (50 ml) was added and stirred to wash. After filtering the mixture, the solids was mixed with excess hydrogen peroxide and stirred to wash for 30 to 60 minutes. The solids was washed by distilled water and filtered and dried such that compound "a" in white solid was obtained. (yield: 90%)

(2) Compound "b"

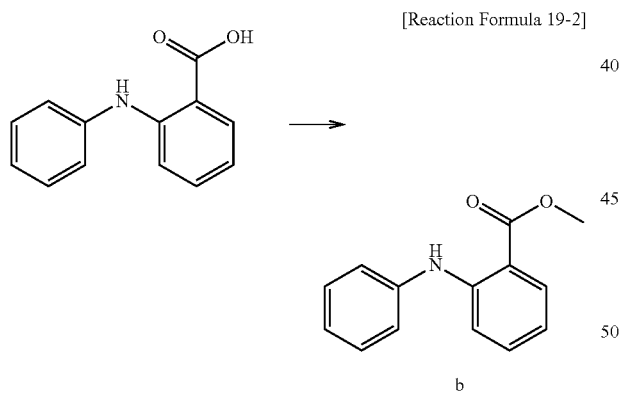

[Reaction Formula 19-2]

b

In the N$_2$ gas purging system, N-phenylanthraniliic acid (46.9 mmol) and methanol solvent were mixed and stirred. The mixture was additionally stirred for 10 minutes under a temperature of 0° C., and thionyl chloride (21.2 mmol) was slowly dropped. The mixed solution was stirred for 12 hours or more under a temperature of 90° C. After completion of the reaction, the solvent was removed, and the mixed solution was extracted by distilled water and ethylacetate. Moisture was removed from the extracted organic layer by using magnesium sulfate, and the solvent was removed. The resultant was wet-refined by column-chromatography using hexane and ethylacetate such that compound "b" of dark yellow liquid was obtained. (yield: 81%)

(3) Compound "c"

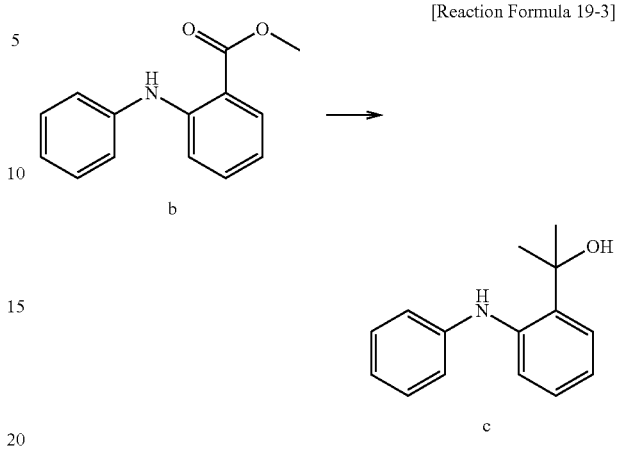

[Reaction Formula 19-3]

b c

In the N$_2$ gas purging system, compound "b" (38.1 mmol) and tetrahydrofuran solvent was stirred. Methyl magnesium bromide (4.6 equivalent) was slowly dropped in the solution, and the solution was stirred and reacted for 12 hours or more under room temperature. After completion of the reaction, distilled water was slowly added, and the solution was extracted by ethylacetate. Moisture was removed from the extracted organic layer by using magnesium sulfate, and the solvent was removed. The resultant was wet-refined by column-chromatography using hexane and ethylacetate such that compound "c" of yellow liquid was obtained. (yield: 87%)

(4) Compound "d"

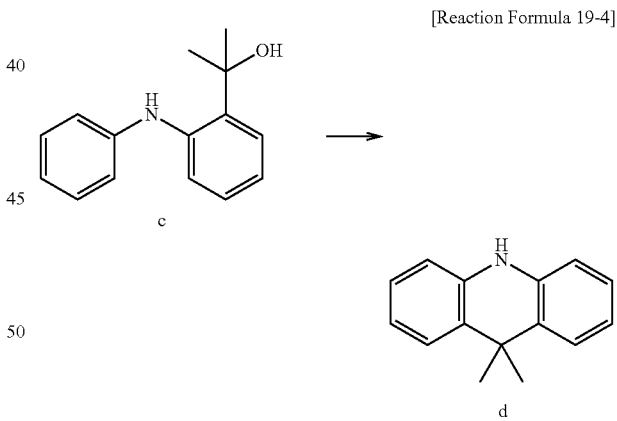

[Reaction Formula 19-4]

c d

In the N$_2$ gas purging system, compound "c" (33.1 mmol) was put into excess phosphoric acid solvent (160 ml), and the solution was stirred under room temperature. The solution was additionally stirred for 16 hours or more, and distilled water (200 to 250 ml) was slowly added. The solution was stirred for 0.5 to 1 hour, and the precipitated solid was filtered. The filtered solid was extracted by using sodium hydroxide aqueous solution and dichloromethane solvent. Moisture was removed from the extracted organic layer by using magnesium sulfate, and the organic solvent was removed such that compound "d" of white solid was obtained. (yield: 69%)

(5) Compound 19

[Reaction Formula 19-5]

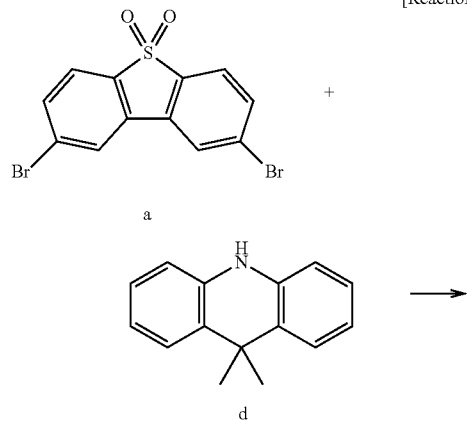

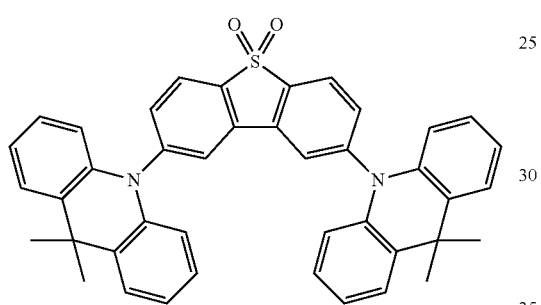

In the N$_2$ gas purging system, compound "d" (0.3 mol), compound "a" (0.15 mol), Pd(OAc)$_2$ (6.11 mmol), P(t-Bu)$_3$ (50 wt %, 15.28 mmol), and sodium tert-butoxide (0.61 mol) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 19 was obtained. (yield: 81%)

20. Synthesis of Compound 20

[Reaction Formula 20]

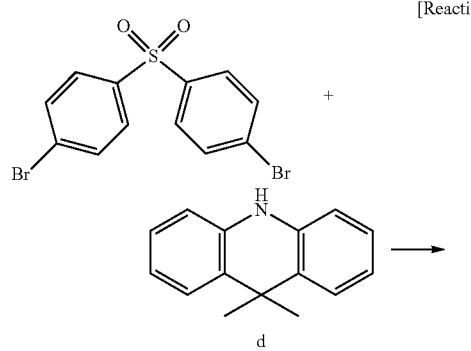

-continued

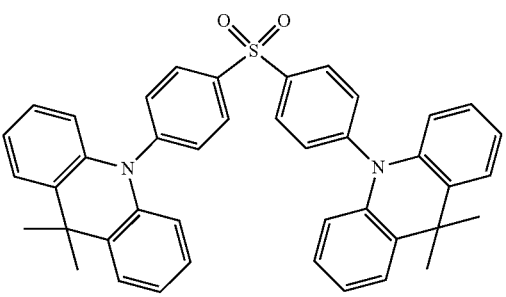

In the N$_2$ gas purging system, compound "d" (0.3 mol), 4-bromophenylsulfone (0.15 mol), Pd(OAc)$_2$ (6.11 mmol), P(t-Bu)$_3$ (50 wt %, 15.28 mmol), and sodium tert-butoxide (0.61 mol) were added into toluene solvent and stirred. The solution was refluxed and stirred for 12 hours under a temperature of 120° C. After completion of the reaction, the solution was cooled into the room temperature and extracted by water and ethylacetate. Moisture was removed from the extracted organic layer by using magnesium sulfate, and the solvent was removed. The resultant was wet-refined by column-chromatography using hexane and ethylacetate such that compound 20 was obtained. (yield: 80%)

21. Synthesis of Compound 21

(1) Compound "e"

[Reaction Formula 21-1]

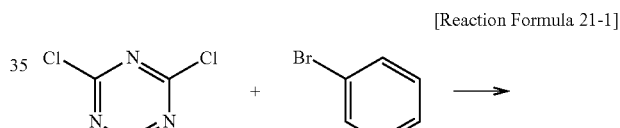

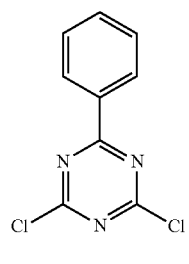

In the light-shielded flask of the N$_2$ gas purging system, bromobenzene (0.9 equivalent) was dissolved in tetrahydrofuran under a temperature of −78° C., and n-butyl-lithium was slowly dropped. 2,4,6-trichloro-1,3,5-triazine dissolved in tetrahydrofuran was dropped into the solution using cannula in the N$_2$ condition and was stirred for 8 hours. After completion of the reaction, the resultant was refined such that compound "e" was obtained. (yield: 45%)

(2) Compound 21

[Reaction Formula 21-2]

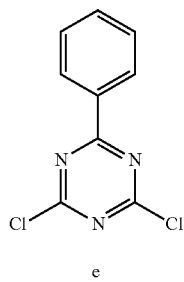

e

+

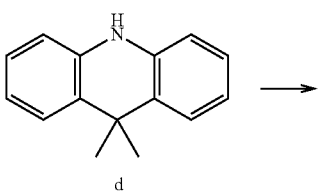

d

→

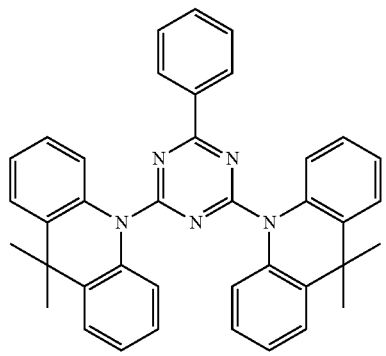

In the N₂ gas purging system, Pd(dba)₂ (5 mol %) as catalyst and P(t-Bu)₃ (4 mol %) was added into toluene solvent and stirred for about 15 minutes. Compound 2 (33.8 mmol), compound "d" (16.9 mmol), and NaOt-Bu (60.6 mmol) were additionally added, and the mixture was stirred for 5 hours under a temperature of 90° C. After completion of the reaction, the mixture was filtered by celite, and the solvent was removed. The filtered solid was refined by column-chromatography using hexane and dichloromethane and re-crystallized using hexane such that compound 21 was obtained. (yield: 59%)

22. Synthesis of Compound 22

[Reaction Formula 22]

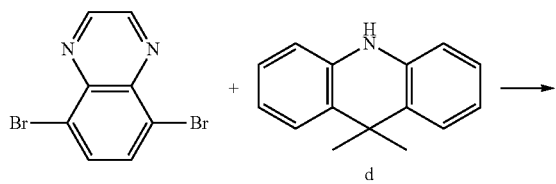

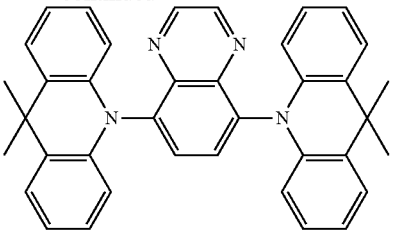

In the N₂ gas purging system, compound "d" (0.3 mol), 5,8-dibromo-quinoxaline (0.15 mol), Pd(OAc)₂ (6.11 mmol), P(t-Bu)₃ (50 wt %, 15.28 mmol), and sodium tert-butoxide (0.61 mol) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 22 was obtained. (yield: 79%)

23. Synthesis of Compound 23

(1) Compound "f"

[Reaction Formula 23-1]

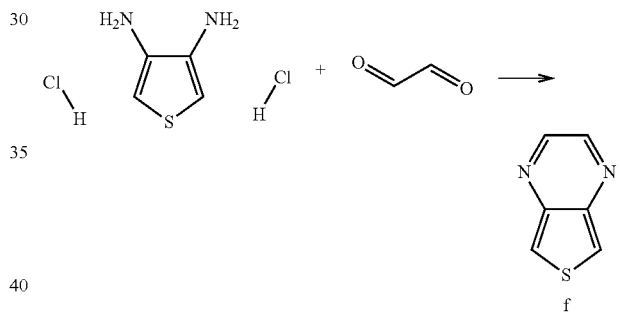

In the N₂ gas purging system, 3,4-diaminothiophene dihydrochloride (5.52 mmol) was slowly added into a mixed solution of Na₂CO₃ (5%, 60 ml) and glyoxal (6.1 mmol) for approximately 5 minutes. Diluted glyoxal solution (40%, 15 mol) was additionally added. The mixture was stirred for 3 hours under room temperature and quickly extracted by ethylacetate. Moisture was removed from the extracted organic layer by using magnesium sulfate, and the solvent was removed without heating. The resultant was wet-refined by column-chromatography using dichloromethane and hexane such that compound "f" was obtained. (yield: 70%)

(2) Compound "g"

[Reaction Formula 23-2]

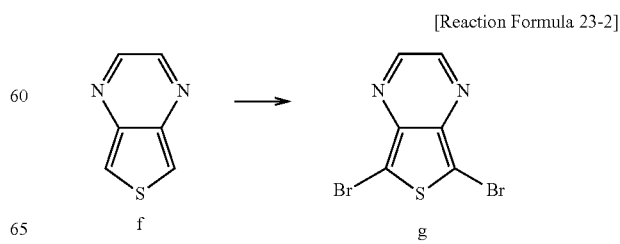

In the N₂ gas purging system, compound "f" (14.7 mmol) was added into solvent of chloroform/acetic acid (1:1) and stirred. The solution was cooled into 0° C., and N-Bromsuccinimid (NBS, 32.3 mmol) was additionally added. The mixture was stirred for 12 hours under room temperature. After completion of the reaction, distilled water of an amount as much as the reaction solvent was added into the mixture, and the solution was extracted by chloroform. Moisture was removed from the extracted organic layer by using magnesium sulfate, and the solvent was removed without heating. The solids were washed by diethyl ether. The resultant was wet-refined by column-chromatography using dichloromethane and hexane such that compound "g" was obtained. (yield: 75%)

(3) Compound 23

[Reaction Formula 23-3]

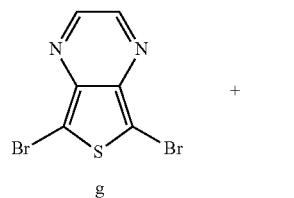

g

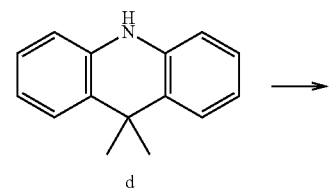

d

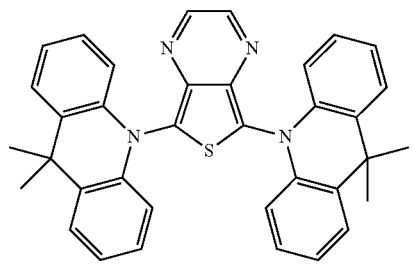

In the N₂ gas purging system, compound "d" (0.3 mol), compound "g" (0.15 mol), Pd(OAc)₂ (6.11 mmol), P(t-Bu)₃ (50 wt %, 15.28 mmol), and sodium tert-butoxide (0.61 mol) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 23 was obtained. (yield: 70%)

24. Synthesis of Compound 24

(1) Compound "h"

[Reaction Formula 24-1]

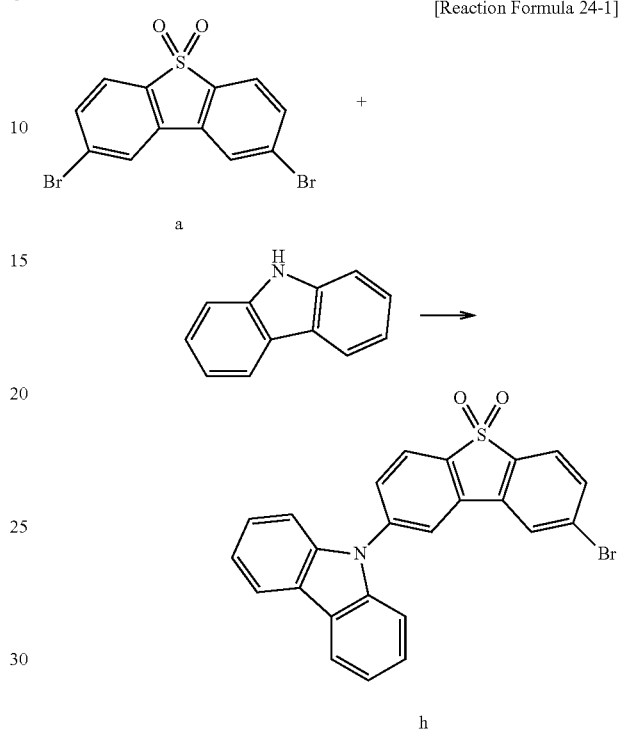

h

In the N₂ gas purging system, carbazole (1.0 equivalent) was dissolved in 1,4-dioxane solvent, and CuI (0.2 equivalent) and K₃PO₄ (1.0 equivalent) were added. Compound "a" (1.1 equivalent) and trans-1,2-diaminocyclohexane were additionally added. The solution was refluxed and stirred for 24 hours under a temperature of 110° C. After completion of the reaction, the solution was cooled in room temperature and extracted by ethylacetate and distilled water. Moisture was removed from the extracted organic layer by using magnesium sulfate, and remaining organic solvent was removed. The resultant was wet-refined by column-chromatography using ethylacetate and hexane such that compound "h" was obtained. (yield: 58%)

(2) Compound 24

[Reaction Formula 24-2]

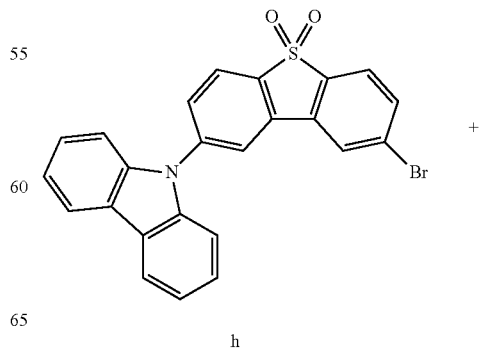

h

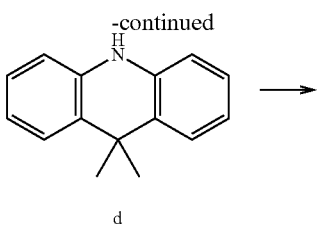

d

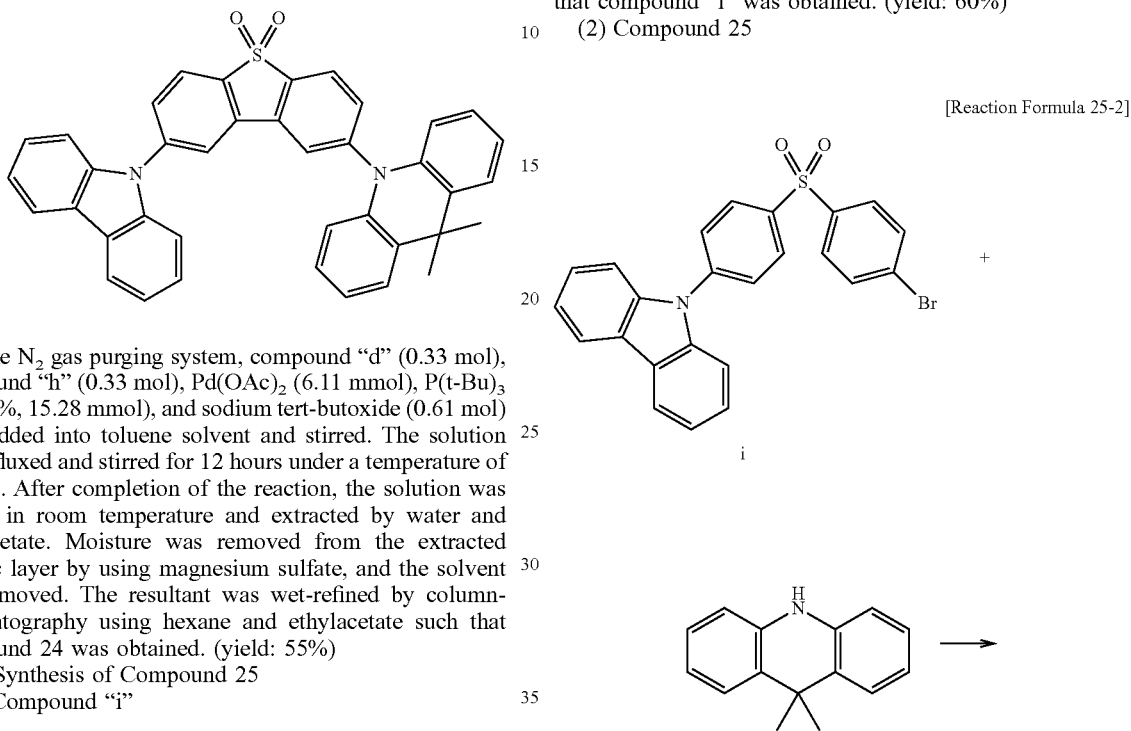

In the N₂ gas purging system, compound "d" (0.33 mol), compound "h" (0.33 mol), Pd(OAc)₂ (6.11 mmol), P(t-Bu)₃ (50 wt %, 15.28 mmol), and sodium tert-butoxide (0.61 mol) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 24 was obtained. (yield: 55%)

25. Synthesis of Compound 25
  (1) Compound "i"

[Reaction Formula 25-1]

i

In the N₂ gas purging system, carbazole (1.0 equivalent) was dissolved in 1,4-dioxane solvent, and CuI (0.2 equivalent) and K₃PO₄ (1.0 equivalent) were added. 4-bromophenylsulfone (1.1 equivalent) and trans-1,2-diaminocyclohexane were additionally added. The solution was refluxed and stirred for 24 hours under a temperature of 110° C. After completion of the reaction, the solution was cooled in room temperature and extracted by ethylacetate and distilled water. Moisture was removed from the extracted organic layer by using magnesium sulfate, and remaining organic solvent was removed. The resultant was wet-refined by column-chromatography using ethylacetate and hexane such that compound "i" was obtained. (yield: 60%)

(2) Compound 25

[Reaction Formula 25-2]

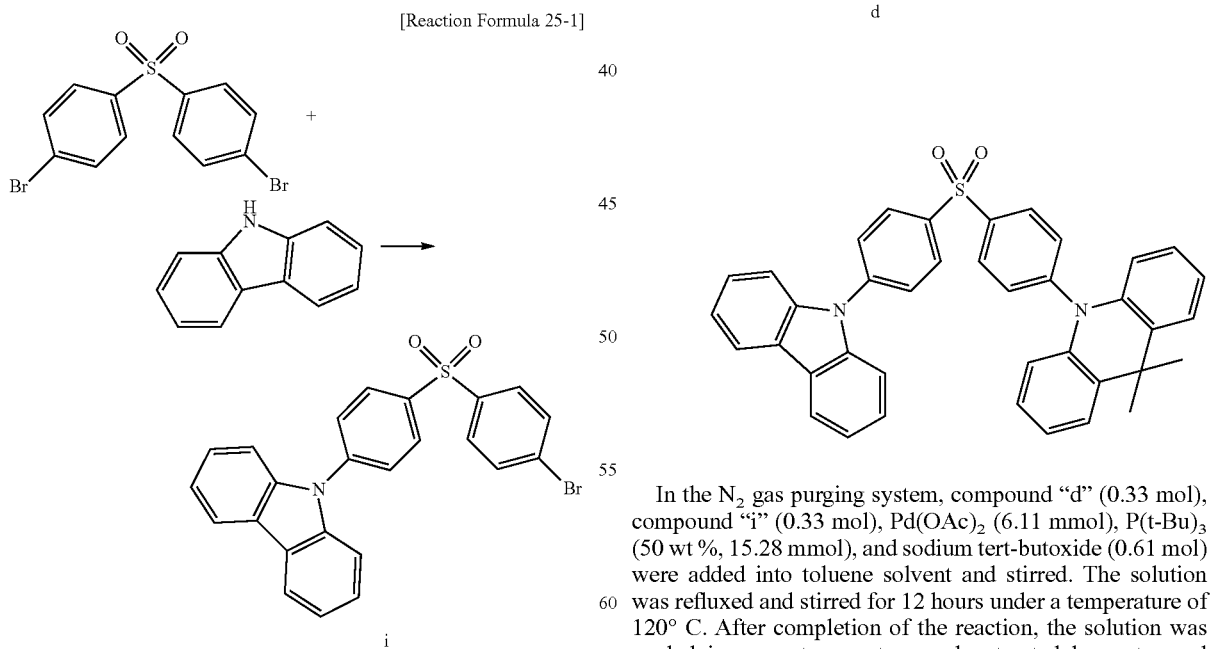

In the N₂ gas purging system, compound "d" (0.33 mol), compound "i" (0.33 mol), Pd(OAc)₂ (6.11 mmol), P(t-Bu)₃ (50 wt %, 15.28 mmol), and sodium tert-butoxide (0.61 mol) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 25 was obtained. (yield: 65%)

26. Synthesis of Compound 26
(1) Compound "j"

[Reaction Formula 26-1]

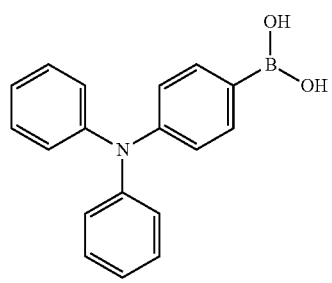

+

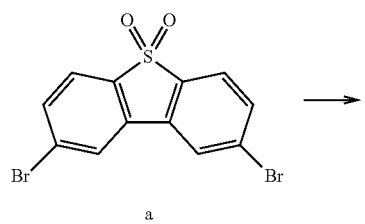

a

→

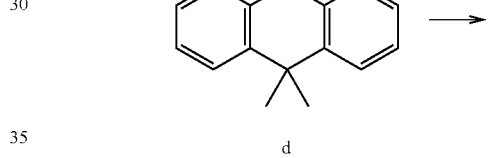

j

In the $N_2$ gas purging system, compound "a" (1.0 equivalent) was dissolved in toluene solvent, and 4-(diphenylamino)phenylboronic acid (1.1 equivalent) was added. $K_2CO_3$ (4.4 equivalent) was dissolved in distilled water and added into the mixed solution. Tetrahydrofuran solvent was added, and palladium (0.05 equivalent) was added. The mixture was refluxed and stirred under a temperature of 80° C. After completion of the reaction, the mixture was extracted by using ethylacetate solvent and distilled water. Moisture was removed from the extracted organic layer by using magnesium sulfate, and remained organic solvent was removed. The resultant was wet-refined by column-chromatography using dichloromethane and hexane such that compound "j" was obtained. (yield: 56%)

(2) Compound 26

[Reaction Formula 26-2]

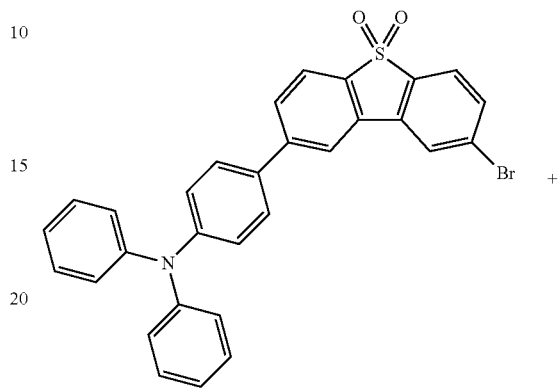

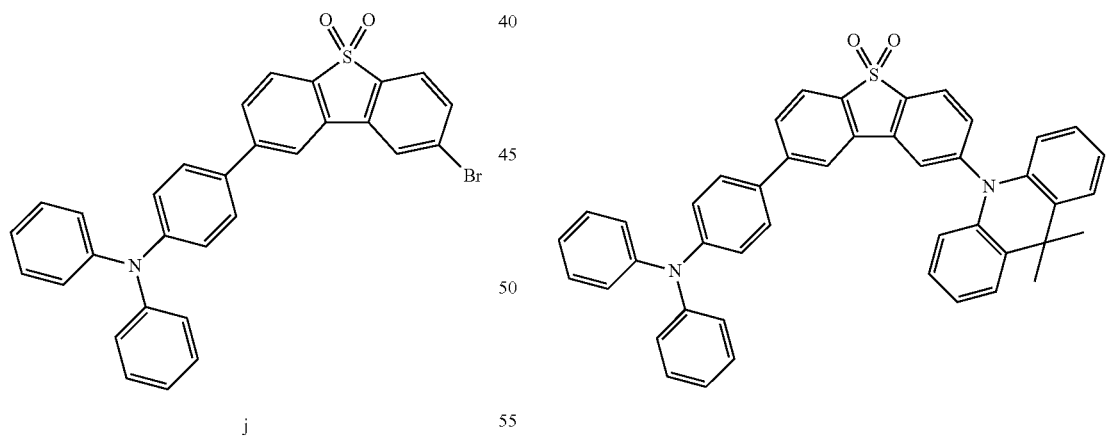

In the $N_2$ gas purging system, compound "d" (0.33 mol), compound 1" (0.33 mol), $Pd(OAc)_2$ (6.11 mmol), $P(t-Bu)_3$ (50 wt %, 15.28 mmol), and sodium tert-butoxide (0.61 mol) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 26 was obtained. (yield: 50%)

27. Synthesis of Compound 27
(1) Compound "k"

[Reaction Formula 27-1]

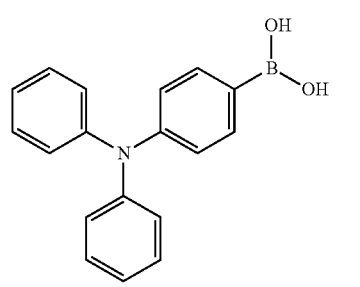

+

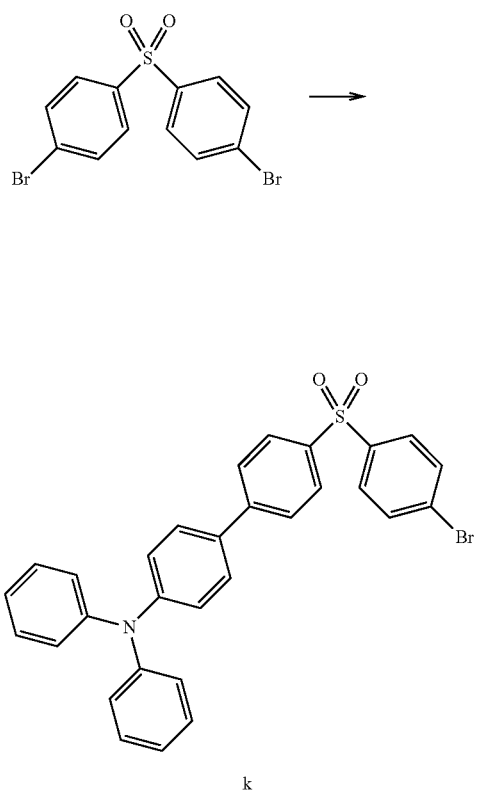

In the N₂ gas purging system, 4-bromophenylsulfone (1.0 equivalent) was dissolved in toluene solvent, and 4-(diphenylamino)phenylboronic acid (1.1 equivalent) was added. K2CO3 (4.4 equivalent) was dissolved in distilled water and added into the mixed solution. Tetrahydrofuran solvent was added, and palladium (0.05 equivalent) was added. The mixture was refluxed and stirred under a temperature of 80° C. After completion of the reaction, the mixture was extracted by ethylacetate. Moisture was removed from the extracted organic layer by using magnesium sulfate, and remaining organic solvent was removed. The resultant was wet-refined by column-chromatography using dichloromethane and hexane such that compound "k" was obtained. (yield: 55%)

(2) Compound 27

[Reaction Formula 27-2]

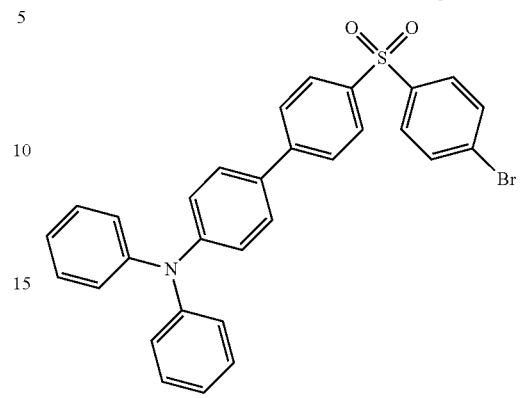

+

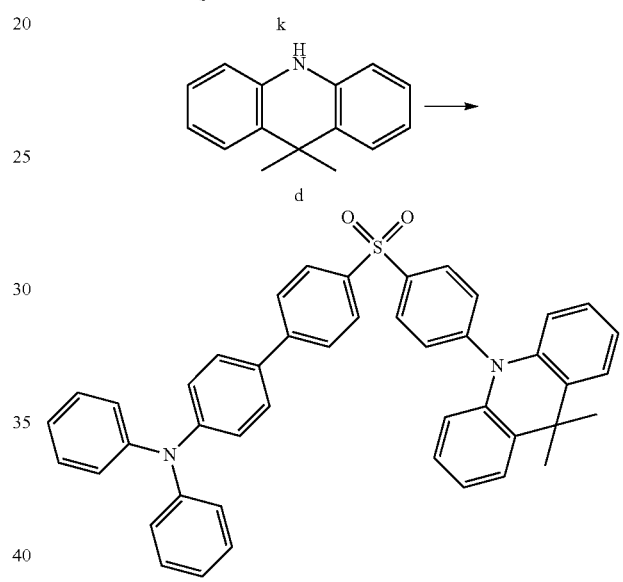

In the N₂ gas purging system, compound "d" (0.33 mol), compound "k" (0.33 mol), Pd(OAc)₂ (6.11 mmol), P(t-Bu)₃ (50 wt %, 15.28 mmol), and sodium tert-butoxide (0.61 mol) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 27 was obtained. (yield: 45%)

28. Synthesis of Compound 28
(1) Compound "1"

[Reaction Formula 28-1]

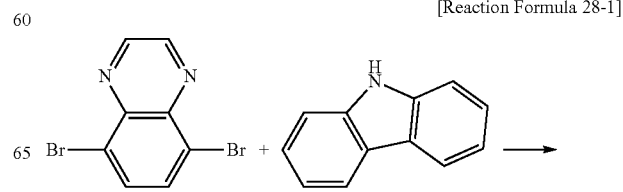

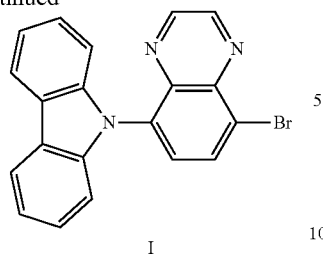

I

In the N₂ gas purging system, carbazole (1.0 equivalent) was dissolved in 1,4-dioxane solvent, and CuI (0.2 equivalent) and K₃PO₄ (1.0 equivalent) were added. 5,8-dibromo-quinoxalin (1.1 equivalent) and trans-1,2-diaminocyclohexane were additionally added. The solution was refluxed and stirred for 24 hours under a temperature of 110° C. After completion of the reaction, the solution was cooled into the room temperature and extracted by ethylacetate and distilled water. Moisture was removed from the extracted organic layer by using magnesium sulfate, and remained organic solvent was removed. The resultant was wet-refined by column-chromatography using ethylacetate and hexane such that compound "1" was obtained. (yield: 48%)

(2) Compound 28

[Reaction Formula 28-2]

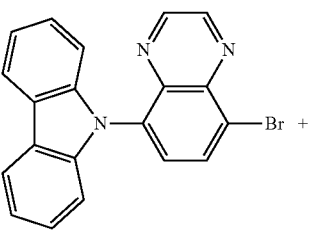

I

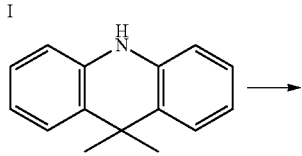

d

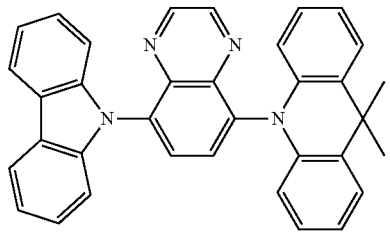

In the N₂ gas purging system, compound "d" (0.33 mol), compound "1" (0.33 mol), Pd(OAc)₂ (6.11 mmol), P(t-Bu)₃ (50 wt %, 15.28 mmol), and sodium tert-butoxide (0.61 mol) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 28 was obtained. (yield: 50%)

29. Synthesis of Compound 29
(1) Compound "m"

[Reaction Formula 29-1]

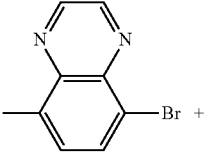

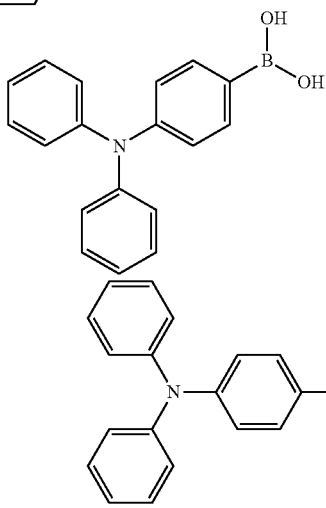

m

In the N₂ gas purging system, 5,8-dibromoquinoxaline (1.0 equivalent) was dissolved in toluene solvent, and 4-(diphenylamino)phenylboronic acid (1.1 equivalent) was added. K₂CO₃ (4.4 equivalent) was dissolved in distilled water and added into the mixed solution. Tetrahydrofuran solvent was added, and palladium (0.05 equivalent) was added. The mixture was refluxed and stirred under a temperature of 80° C. After completion of the reaction, the mixture was extracted by ethylacetate. Moisture was removed from the extracted organic layer by using magnesium sulfate, and remaining organic solvent was removed. The resultant was wet-refined by column-chromatography using dichloromethane and hexane such that compound "m" was obtained. (yield: 43%)

(2) Compound 29

[Reaction Formula 29-2]

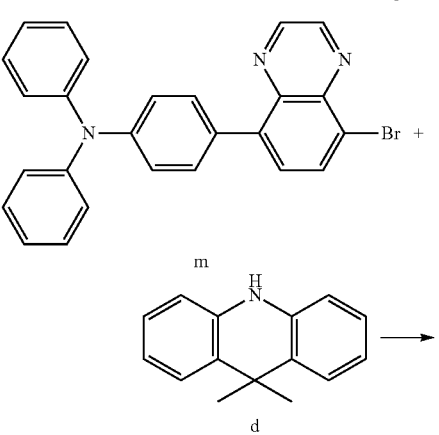

m d

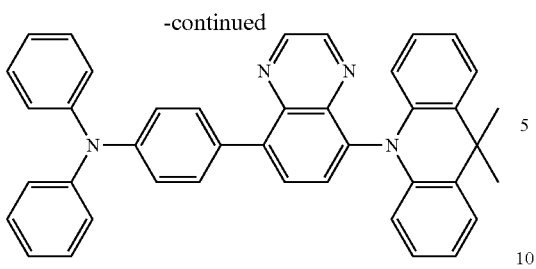

In the N$_2$ gas purging system, compound "d" (0.33 mol), compound "m" (0.33 mol), Pd(OAc)$_2$ (6.11 mmol), P(t-Bu)$_3$ (50 wt %, 15.28 mmol), and sodium tert-butoxide (0.61 mol) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 29 was obtained. (yield: 50%)

30. Synthesis of Compound 30

(1) Compound "n"

[Reaction Formula 30-1]

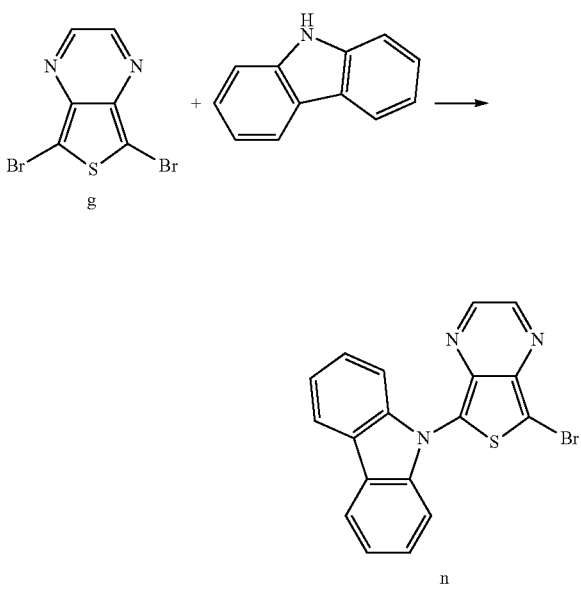

In the N$_2$ gas purging system, carbazole (1.0 equivalent) was dissolved in 1,4-dioxane solvent, and CuI (0.2 equivalent) and K$_3$PO$_4$ (1.0 equivalent) were added. Compound "g" (1.1 equivalent) and trans-1,2-diaminocyclohexane were additionally added. The solution was refluxed and stirred for 24 hours under a temperature of 110° C. After completion of the reaction, the solution was cooled in room temperature and extracted by ethylacetate and distilled water. Moisture was removed from the extracted organic layer by using magnesium sulfate, and remaining organic solvent was removed. The resultant was wet-refined by column-chromatography using ethylacetate and hexane such that compound "n" was obtained. (yield: 45%)

(2) Compound 30

[Reaction Formula 30-2]

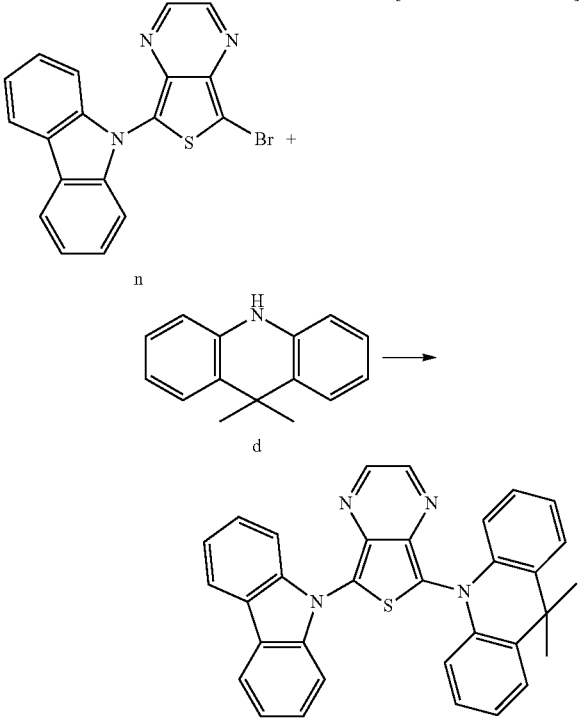

In the N$_2$ gas purging system, compound "d" (0.33 mol), compound "n" (0.33 mol), Pd(OAc)$_2$ (6.11 mmol), P(t-Bu)$_3$ (50 wt %, 15.28 mmol), and sodium tert-butoxide (0.61 mol) were added into toluene solvent and stirred. The solution was refluxed and stirred for 12 hours under a temperature of 120° C. After completion of the reaction, the solution was cooled in room temperature and extracted by water and ethylacetate. Moisture was removed from the extracted organic layer by using magnesium sulfate, and the solvent was removed. The resultant was wet-refined by column-chromatography using hexane and ethylacetate such that compound 30 was obtained. (yield: 49%)

The mass spectrum data of the above compounds 1 to 30 are listed in Table 1.

TABLE 1

|  |  | Calculation | Found (M(H+)) |
| --- | --- | --- | --- |
| Com1 | $C_{33}H_{25}N_1O_2S_1$ | 499.16 | 499.16 |
| Com2 | $C_{39}H_{29}N_1O_2S_1$ | 575.19 | 575.19 |
| Com3 | $C_{33}H_{27}N_1O_2S_1$ | 501.18 | 501.18 |
| Com4 | $C_{39}H_{31}N_1O_2S_1$ | 577.21 | 577.21 |
| Com5 | $C_{30}H_{24}N_4$ | 440.2 | 440.2 |
| Com6 | $C_{36}H_{28}N_4$ | 516.23 | 516.23 |
| Com7 | $C_{27}H_{22}N_4$ | 402.18 | 402.18 |
| Com8 | $C_{29}H_{26}N_4$ | 430.22 | 430.22 |
| Com9 | $C_{28}H_{23}N_3$ | 401.19 | 401.19 |
| Com10 | $C_{30}H_{27}N_3$ | 429.22 | 429.22 |
| Com11 | $C_{54}H_{42}N_2O_2S$ | 782.30 | 782.30 |
| Com12 | $C_{51}H_{36}N_2O_2S$ | 740.25 | 740.25 |
| Com13 | $C_{54}H_{42}N_2O_2S$ | 782.30 | 782.30 |
| Com14 | $C_{51}H_{38}N_2O_2S$ | 742.27 | 742.27 |
| Com15 | $C_{51}H_{41}N_5$ | 723.34 | 723.34 |
| Com16 | $C_{48}H_{35}N_5$ | 681.29 | 681.29 |
| Com17 | $C_{50}H_{40}N_4$ | 696.33 | 696.33 |
| Com18 | $C_{47}H_{34}N_4$ | 654.28 | 654.27 |
| Com19 | $C_{42}H_{34}N_2O_2S$ | 630.23 | 630.23 |

TABLE 1-continued

| | | Calculation | Found (M(H+)) |
|---|---|---|---|
| Com20 | $C_{42}H_{36}N_2O_2S$ | 632.25 | 632.25 |
| Com21 | $C_{39}H_{33}N_5$ | 571.27 | 571.27 |
| Com22 | $C_{38}H_{32}N_4$ | 544.26 | 544.26 |
| Com23 | $C_{36}H_{30}N_4S$ | 550.22 | 550.22 |
| Com24 | $C_{39}H_{28}N_2O_2S$ | 588.19 | 588.19 |
| Com25 | $C_{39}H_{30}N_2O_2S$ | 590.20 | 590.20 |
| Com26 | $C_{45}H_{34}N_2O_2S$ | 666.23 | 666.23 |
| Com27 | $C_{45}H_{36}N_2O_2S$ | 668.25 | 668.25 |

TABLE 1-continued

| | | Calculation | Found (M(H+)) |
|---|---|---|---|
| Com28 | $C_{35}H_{26}N_4$ | 502.22 | 502.22 |
| Com29 | $C_{41}H_{32}N_4$ | 580.26 | 580.26 |
| Com30 | $C_{33}H_{24}N_4S$ | 508.17 | 508.17 |

The emission properties of the above compounds 3, 6, 7, 9, 11, 15, 16, 23, 27, and 29 are measured and the results are listed in Table 2 and shown in FIGS. 4A to 4J. (Quantarus tau apparatus of Hamamatsu Co., Ltd. $O_2$ free condition.)

TABLE 2

| | Fluorescence (ns) | Delayed fluorescence (ns) |
|---|---|---|
| 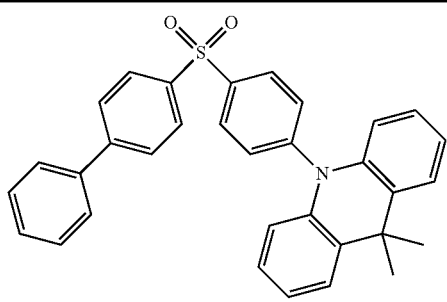<br>Com3 | 7.28 | 820 |
| 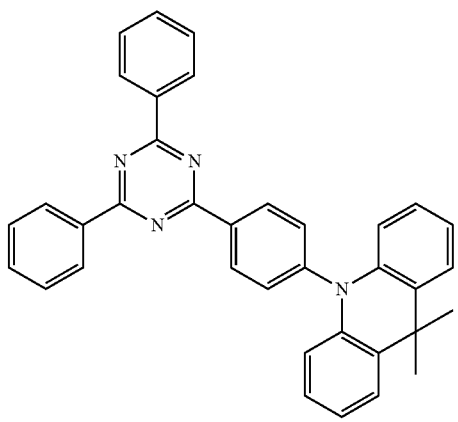<br>Com6 | 9.51 | 5220 |
| 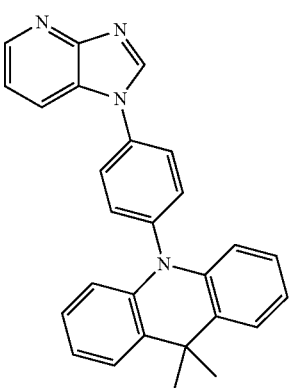<br>Com7 | 7.28 | 41100 |

TABLE 2-continued
| | Fluorescence (ns) | Delayed fluorescence (ns) |
|---|---|---|
| 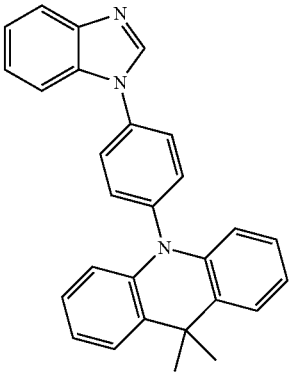<br>Com9 | 6.32 | 3120 |
| 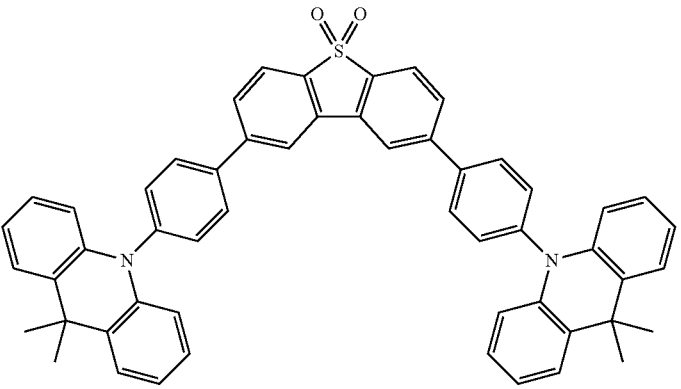<br>Com11 | 47.02 | 7875 |
| 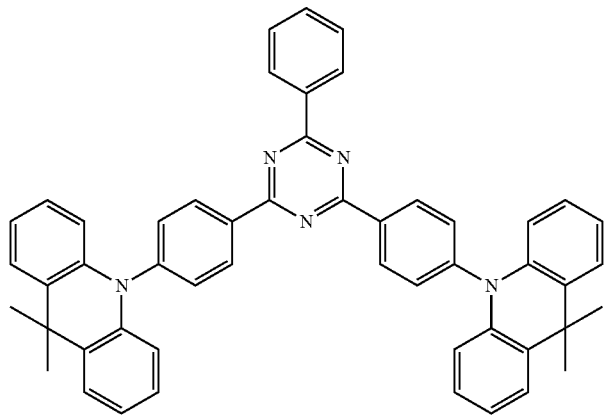<br>Com15 | 23.13 | 3870 |

TABLE 2-continued
| | Fluorescence (ns) | Delayed fluorescence (ns) |
|---|---|---|
| 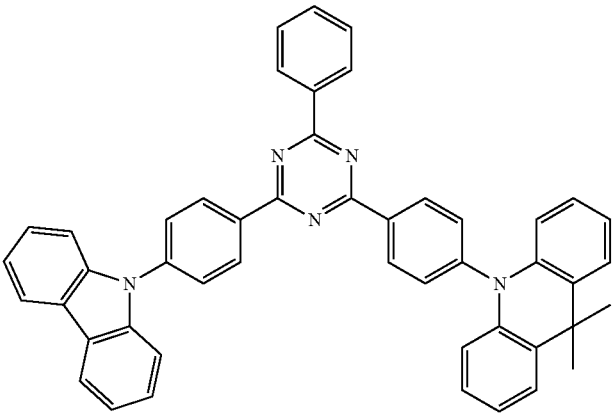 Com16 | 25.60 | 5755 |
| 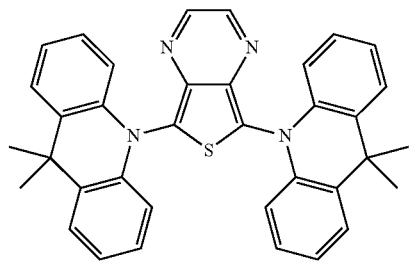 Com23 | 7.66 | 6956 |
| 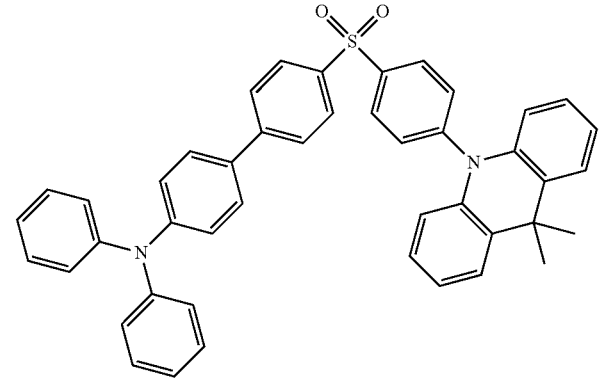 Com27 | 5.00 | 6753 |
| 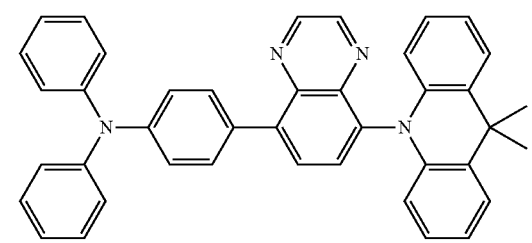 Com29 | 3.50 | 5645 |

As shown in Table 2 and FIGS. 4A to 4J, the delayed fluorescence compounds (Com3, Com6, Com7, Com9, Com11, Com15, Com16, Com23, Com27, and Com29) of the present disclosure show the delayed fluorescent emission of hundreds to tens of thousands of nano-seconds (ns).

As mentioned above, the delayed fluorescence compound of the present invention is activated by the field such that the excitons in the singlet state "$S_1$" and the triplet state "$T_1$" are transited into the intermediated state "$I_1$". As a result, both the exciton in the singlet state "$S_1$" and the exciton in the triplet state "$T_1$" are engaged in the emission.

The FADF compound is a single molecule compound having the electron donor moiety and the electron acceptor moiety in the single molecule with or without another electron donor moiety such that the charge transfer is easily generated. In the FADF compound with particular conditions, the charge can be separated from the electron donor moiety to the electron acceptor moiety.

The FADF compound is activated by outer factors. It can be verified by comparing the absorption peak and the emission peak of the solution of the compounds.

$$\Delta v = vabs - vfl = \frac{2\Delta\mu^2}{hca^3}\Delta f + \text{constant} \quad \text{(Lippert-Mataga equation)}$$

In the above equation, "$\Delta\upsilon$" is the Stock-shift value, and "$\upsilon abs$" and "$\upsilon fl$" are the wave-number of the maximum absorption peak and the maximum emission peak, respectively. "h" is Planck's constant, "c" is the velocity of light, "a" is the onsager cavity radius, and "$\Delta\mu$" is a difference between the dipole moment of the excited state and the dipole moment of the ground state. ($\Delta\mu=\mu_e-\mu_g$)

"$\Delta f$" is a value indicating the orientational polarizability of the solvent and may be a function of the dielectric constant of the solvent ($\varepsilon$) and the refractive index of the solvent (n).

$$\Delta f = \frac{\varepsilon - 1}{2\varepsilon + 1} - \frac{n^2 - 1}{2n^2 + 1}$$

Since the intensity of dipole moment in the excited state is determined by the peripheral polarity (e.g., the polarity of the solvent), the FADF can be verified by comparing the absorption peak and the emission peak of the solution of the compounds.

The orientational polarizability ($\Delta f$) of the mixed solvent can be calculated by using the orientational polarizability of each pure solvent and their mole fraction. When "$\Delta f$" and "$\Delta\upsilon$" are linearly plotted by using above "Lippert-Mataga equation", the compound may provide the FADF emission.

Namely, when the FADF complex is stabilized according to the orientational polarizability of the solvent, the emission peak is shifted in a long wavelength according to the degree of the stabilization. Accordingly, when the compound provides the FADF emission, "$\Delta f$" and "$\Delta\upsilon$" are plotted in a linear line. When "$\Delta f$" and "$\Delta\upsilon$" are plotted in a linear line, the compound provides the FADF emission.

In the delayed fluorescence compound of the present invention, the 25% excitons in the singlet state and the 75% excitons in the triplet state are transited into the intermediate state by an outer force, i.e., a field generated when the OLED is driven. (Intersystem crossing.) The excitons in the intermediate state are transited into the ground state such that the emitting efficiency is improved. Namely, in the fluorescent compound, since both the singlet exciton and the triplet exciton are engaged in the emission, the emitting efficiency is improved.

OLED

An ITO layer is deposited on a substrate and washed to form an anode (3 mm*3 mm). The substrate is loaded in a vacuum chamber, and a hole injecting layer (500 Å, NPB (N,N-di(naphthalen-1-yl)-N,N'-diphenyl-benzidine)), a hole transporting layer (100 Å, mCP(N,N'-Dicarbazolyl-3,5-benzene)), an emitting material layer (350 Å, host (bis{2-[di (phenyl)phosphino]phenyl}ether oxide) and dopant (6%)), an electron transporting layer (300 Å, 1,3,5-tri(phenyl-2-benzimidazole)-benzene), an electron injecting layer (LiF), and a cathode (Al) are sequentially formed on the anode under a base pressure of about $10^{-6}$ to $10^{-7}$ Torr.

(1) Comparative Example (Ref)

The reference compound in Formula 8 is used as the dopant to form the OLED.

(2) Example 1 (Ex1)

The compound 3 is used as the dopant to form the OLED.

(3) Example 2 (Ex2)

The compound 6 is used as the dopant to form the OLED.

(4) Example 3 (Ex3)

The compound 7 is used as the dopant to form the OLED.

(5) Example 4 (Ex4)

The compound 9 is used as the dopant to form the OLED.

(6) Example 5 (Ex5)

The compound 11 is used as the dopant to form the OLED.

(7) Example 6 (Ex6)

The compound 13 is used as the dopant to form the OLED.

(8) Example 7 (Ex7)

The compound 15 is used as the dopant to form the OLED.

(9) Example 8 (Ex8)

The compound 16 is used as the dopant to form the OLED.

(10) Example 9 (Ex9)

The compound 17 is used as the dopant to form the OLED.

(11) Example 10 (Ex10)

The compound 19 is used as the dopant to form the OLED.

(12) Example 11 (Ex11)

The compound 20 is used as the dopant to form the OLED.

(13) Example 12 (Ex12)

The compound 21 is used as the dopant to form the OLED.

(14) Example 13 (Ex13)

The compound 22 is used as the dopant to form the OLED.

(15) Example 14 (Ex14)

The compound 23 is used as the dopant to form the OLED.

(16) Example 15 (Ex15)

The compound 24 is used as the dopant to form the OLED.

(17) Example 16 (Ex16)

The compound 30 is used as the dopant to form the OLED.

TABLE 3

|  | Voltage (V) | Cd/A | lm/W | EQE (%) | CIE (X) | CIE (Y) |
| --- | --- | --- | --- | --- | --- | --- |
| Ref | 8.85 | 7.42 | 2.63 | 4.07 | 0.177 | 0.297 |
| Ex1 | 5.95 | 14.53 | 7.67 | 8.65 | 0.166 | 0.265 |
| Ex2 | 4.88 | 41.85 | 26.91 | 15.63 | 0.275 | 0.549 |
| Ex3 | 5.88 | 14.70 | 7.86 | 7.06 | 0.202 | 0.371 |
| Ex4 | 5.45 | 12.27 | 7.07 | 7.48 | 0.1647 | 0.254 |
| Ex5 | 5.24 | 10.38 | 7.74 | 6.87 | 0.171 | 0.203 |
| Ex6 | 5.16 | 10.07 | 8.01 | 6.48 | 0.159 | 0.190 |
| Ex7 | 4.91 | 42.49 | 26.23 | 15.32 | 0.275 | 0.546 |
| Ex8 | 5.81 | 12.12 | 6.77 | 6.80 | 0.170 | 0.263 |
| Ex9 | 4.86 | 46.75 | 28.32 | 16.84 | 0.281 | 0.561 |
| Ex10 | 5.26 | 13.41 | 8.84 | 7.18 | 0.176 | 0.202 |
| Ex11 | 5.03 | 11.78 | 8.62 | 7.34 | 0.172 | 0.189 |
| Ex12 | 5.96 | 15.42 | 8.94 | 8.05 | 0.182 | 0.284 |
| Ex13 | 5.46 | 20.68 | 10.09 | 8.81 | 0.194 | 0.328 |

TABLE 3-continued

|  | Voltage (V) | Cd/A | lm/W | EQE (%) | CIE (X) | CIE (Y) |
| --- | --- | --- | --- | --- | --- | --- |
| Ex14 | 5.08 | 32.84 | 25.61 | 11.84 | 0.264 | 0.437 |
| Ex15 | 5.84 | 11.13 | 7.64 | 6.84 | 0.168 | 0.198 |
| Ex16 | 5.11 | 38.88 | 20.04 | 13.59 | 0.302 | 0.482 |

As shown in Table 3, in the OLEDs using the compounds of the present disclosure (Ex1 to Ex16), the properties in the driving voltage, the emitting efficiency and so on are improved.

Figure 5:
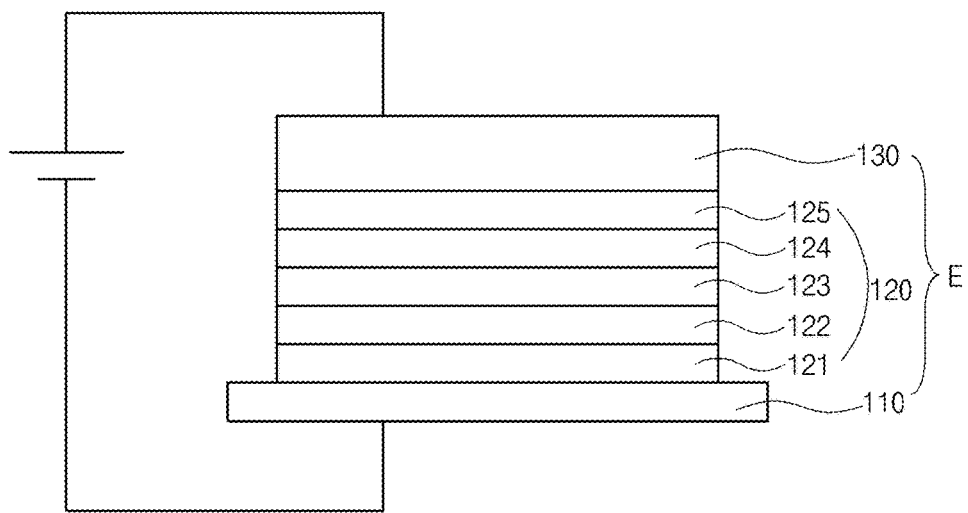
FIG. 5 is a schematic cross-sectional view of an OLED according to the present disclosure.

FIG. 5 is a schematic cross-sectional view of an OLED according to the invention.

As shown in FIG. 5, the OLED "E" is formed on a substrate (not shown). The OLED "E" includes a first electrode 110 as an anode, a second electrode 130 as a cathode, and an organic emitting layer 120 therebetween.

Although not shown, an encapsulation film, which includes at least one inorganic layer and at least one organic layer and covers the OLED "E", and a cover window on the encapsulation film, may be further formed to form a display device including the OLED "E". The substrate, the encapsulation film and the cover window may have a flexible property such that a flexible display device may be provided.

The first electrode 110 is formed of a material having a relatively high work function, and the second electrode 130 is formed of a material having a relatively low work function. For example, the first electrode 110 may be formed of indium-tin-oxide (ITO), and the second electrode 130 may be formed of aluminum (Al) or Al alloy (AlNd). The organic emitting layer 120 may include red, green, and blue emitting patterns.

The organic emitting layer 120 may have a single-layered structure.

Alternatively, to improve the emitting efficiency, the organic emitting layer 120 includes a hole injection layer (HIL) 121, a hole transporting layer (HTL) 122, an emitting material layer (EML) 123, an electron transporting layer (ETL) 124, and an electron injection layer (EIL) 125 sequentially stacked on the first electrode 110.

At least one selected from the HIL 121, the HTL 122, the EML 123, the ETL 124, and the EIL 125 includes the delayed fluorescence compound in the Formulas 1-1 or 1-2.

For example, the EML 123 may include the delayed fluorescence compound in the Formulas 1-1 or 1-2. The

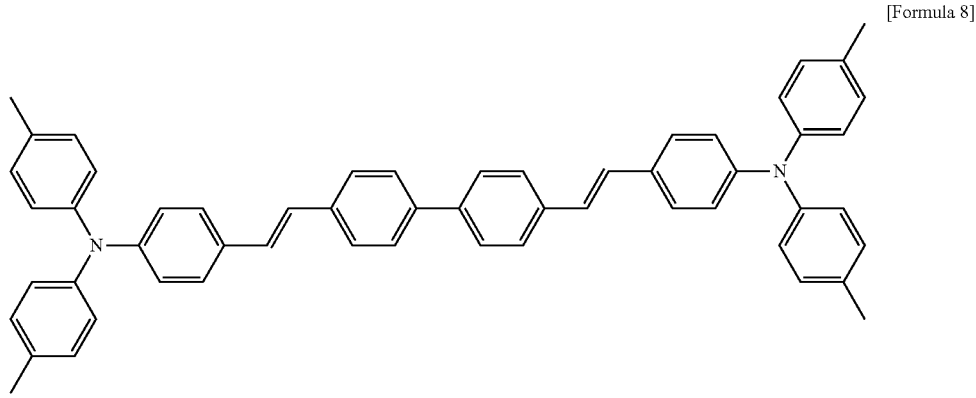 [SMILES: Cc1ccc(N(c2ccc(C)cc2)c2ccc(/C=C/c3ccc(-c4ccc(/C=C/c5ccc(N(c6ccc(C)cc6)c6ccc(C)cc6)cc5)cc4)cc3)cc2)cc1]

[Formula 8]

delayed fluorescence compound acts as the dopant, and the EML 123 may further include a host to emit the blue light. In this instance, the dopant has about 1 to 30 weight % with respect to the host.

A difference between the HOMO of the host "$HOMO_{Host}$" and the HOMO of the dopant "$HOMO_{Dopant}$" or a difference between the LUMO of the host "$LUMO_{Host}$" and the LUMO of the dopant "$LUMO_{Dopant}$" is less than 0.5 eV. ($|HOMO_{Host}-HOMO_{Dopant}| \leq 0.5$ eV or $|LUMO_{Host}-LUMO_{Dopant}| \leq 0.5$ eV.) In this instance, the charge transfer efficiency from the host to the dopant may be improved.

For example, the host, which meets the above condition, may be selected from materials in Formula 9. (Bis[2-(diphenylphosphino)phenyl]ether oxide (DPEPO), 2,8-bis(diphenylphosphoryl)dibenzothiophene (PPT), 2,8-di(9H-carbazol-9-yl)dibenzothiophene (DCzDBT), m-bis(carbazol-9-yl)biphenyl (m-CBP), Diphenyl-4-triphenylsilylphenyl-phosphine oxide (TPSO1), 9-(9-phenyl-9H-carbazol-6-yl)-9H-carbazole (CCP) in order.)

[Formula 9]

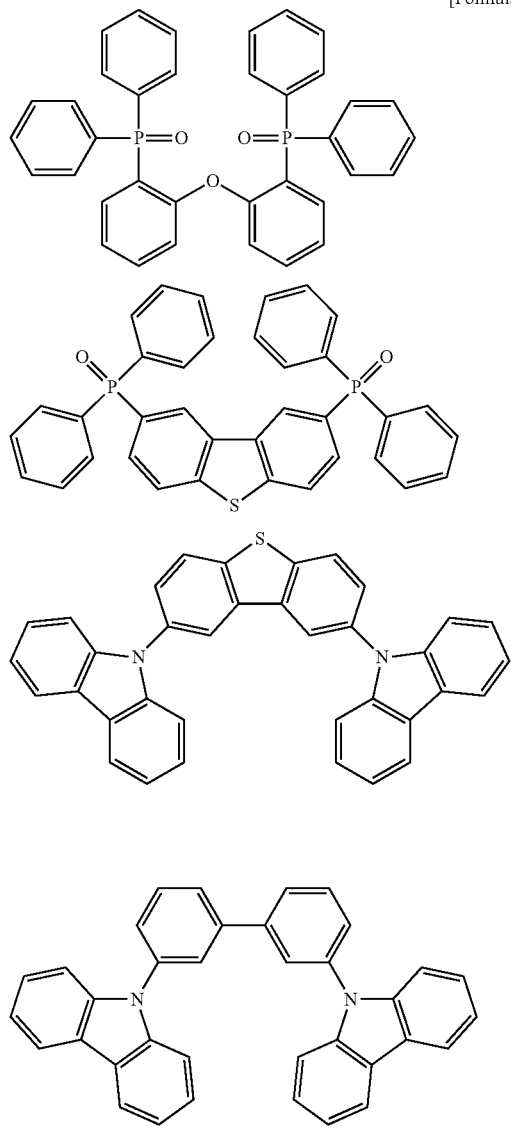

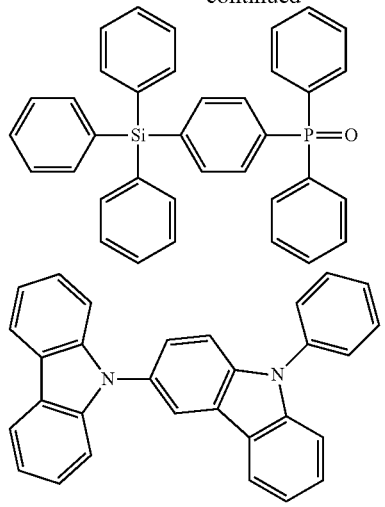

The triplet energy of the dopant is smaller than the triplet energy of the host, and a difference between the singlet energy of the dopant and the triplet energy of the dopant is less than 0.3 eV. ($\Delta E_{ST} \leq 0.3$ eV.) As the difference "$\Delta E_{ST}$" is smaller, the emitting efficiency is higher. In the delayed fluorescence compound of the present invention, even if the difference "$\Delta E_{ST}$" between the singlet energy of the dopant and the triplet energy of the dopant is about 0.3 eV, which is relatively large, the excitons in the singlet state "S1" and the excitons in the triplet state "T1" can be transited into the intermediate state "I1".

On the other hand, the delayed fluorescence compound of the present invention may act as a host in the EML 123, and the EML 123 may further include a dopant to emit the blue light. In this instance, the dopant has approximately 1 to 30 weight % with respect to the host. Since the development of the blue host having excellent properties is insufficient, the delayed fluorescence compound of the present invention may be used as the host to increase the degree of freedom for the host. In this instance, the triplet energy of the dopant may be smaller than the triplet energy of the host of the delayed fluorescence compound of the present disclosure.

The EML 123 may include a first dopant of the delayed fluorescence compound of the present disclosure, a host, and a second dopant. The weight % summation of the first and second dopants may be about 1 to 30 to emit the blue light. In this instance, the emitting efficiency and the color purity may be further improved.

In this instance, the triplet energy of the first dopant, i.e., the delayed fluorescence compound of the present disclosure, may be smaller than the triplet energy of the host, and larger than the triplet energy of the second dopant. In addition, a difference between the singlet energy of the first dopant and the triplet energy of the first dopant is less than 0.3 eV. ($\Delta E_{ST} \leq 0.3$ eV.) As the difference "$\Delta E_{ST}$" is smaller, the emitting efficiency is higher. In the delayed fluorescence compound of the present disclosure, even if the difference "$\Delta E_{ST}$" between the singlet energy of the dopant and the triplet energy of the dopant is about 0.3 eV, which is relatively large, the excitons in the singlet state "$S_1$" and the excitons in the triplet state "$T_1$" can be transited into the intermediate state "$I_1$".

As mentioned above, since the delayed fluorescence compound of the present disclosure includes the electron donor moiety and the electron acceptor moiety with or without another electron donor moiety, and the electron donor moiety of acridine forms a large steric hindrance with the electron acceptor moiety, the emitting efficiency is improved. In addition, the dipole from the first and second electron donor moieties to the electron acceptor moiety is generated such that the dipole moment in the molecule is increased. As a result, the emitting efficiency is further improved. Moreover, in the delayed fluorescent compound of the present invention, the excitons in the triplet state are engaged in the emission such that the emitting efficiency of the delayed fluorescent compound is increased.

Since a gap or a distance between the electron donor moiety and the electron acceptor moiety is increased due to the linker, an overlap between HOMO and LUMO is reduced such that a gap ($\Delta E_{ST}$) between the triple energy and the singlet energy is reduced. In addition, due to the steric hindrance of the linker, the red shift problem in the light emitted from the emitting layer including the delayed fluorescence compound is decreased or minimized.

Accordingly, the OLED and the display device using or including the delayed fluorescence compound of the present disclosure has an advantage in the emitting efficiency.

It will be apparent to those skilled in the art that various modifications and variations can be made in the embodiment of the invention without departing from the spirit or scope of the invention. Thus, it is intended that the embodiment of the invention cover the modifications and variations of this invention provided they come within the scope of the appended claims and their equivalents.

What is claimed is:

1. An organic light emitting diode, comprising:

an organic emitting layer including a delayed fluorescence compound of Formula 1:

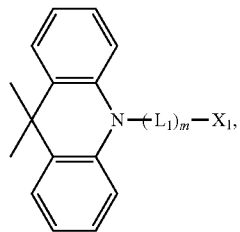

[Formula 1]

wherein a difference between a singlet energy of the delayed fluorescence compound and a triplet energy of the delayed fluorescence compound is less than 0.3 eV.

2. The organic light emitting diode according to claim 1, wherein m is 1, and $X_1$ is selected from Formula 2, wherein each of $L_1$ is from Formula 3:

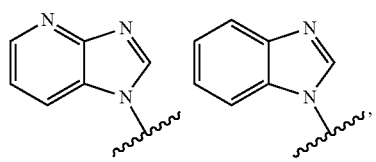

[Formula 2]

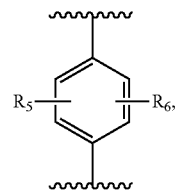

[Formula 3]

wherein each of $R_5$ and $R_6$ in the Formula 3 is independently selected from hydrogen or C1 alkyl through C10 alkyl.

3. The organic light emitting diode according to claim 1, further comprising:

a first electrode; and a second electrode, wherein the organic emitting layer is between the first electrode and the second electrode.

4. The organic light emitting diode according to claim 1, wherein the organic emitting layer further includes a host, and the delayed fluorescence compound is used as a dopant.

5. The organic light emitting diode according to claim 4, wherein a difference between a HOMO of the host and a highest occupied molecular orbital (HOMO) of the dopant or a difference between a lowest unoccupied molecular orbital (LUMO) of the host and a LUMO of the dopant is less than 0.5 eV.

6. The organic light emitting diode according to claim 4, wherein the host is selected from:

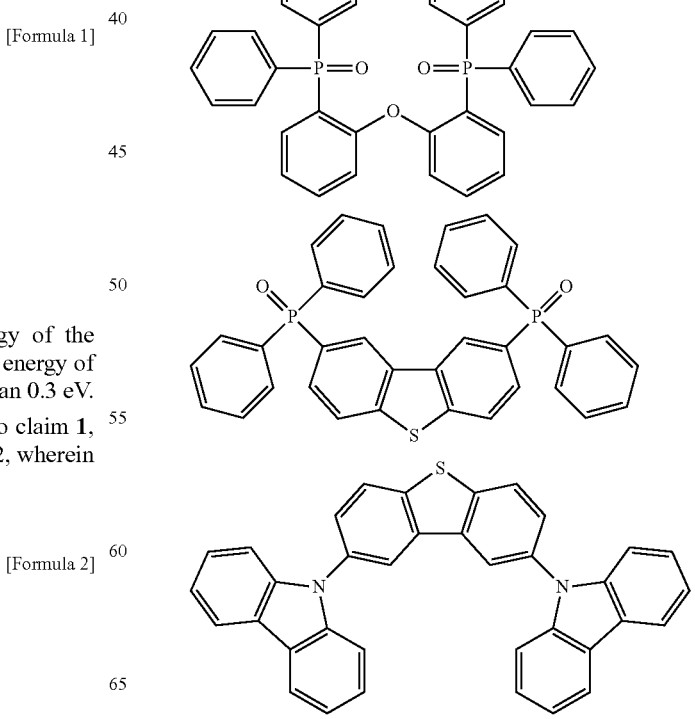

-continued

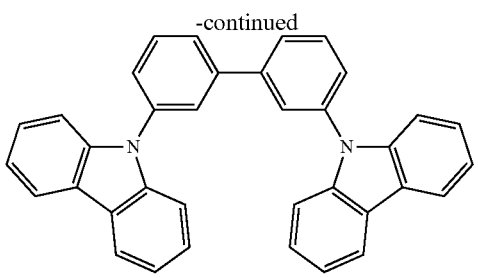

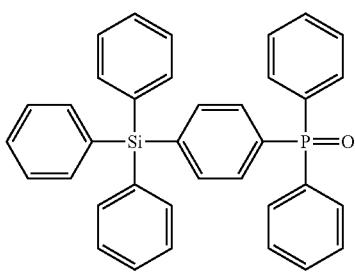

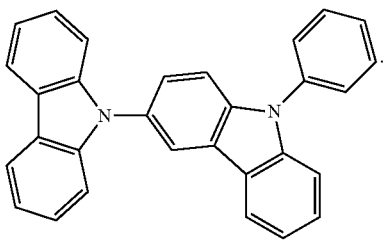

7. The organic light emitting diode according to claim 1, wherein the organic emitting layer includes a hole injection layer (HIL), a hole transporting layer (HTL), an emitting material layer (EML), an electron transporting layer (ETL), and an electron injection layer (EIL), and wherein at least one of the HIL, the HTL, the EML, the ETL, and the EIL includes the delayed fluorescence compound.

8. An organic light emitting diode, comprising:

an organic emitting layer including a host, a first dopant and a second dopant, wherein the first dopant is represented by Formula 1:

[Formula 1]

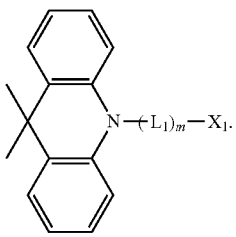

9. The organic light emitting diode according to claim 8, wherein m is 1, and $X_1$ is selected from Formula 2, wherein each of $L_1$ is from Formula 3:

[Formula 2]

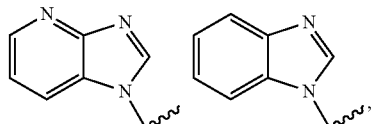

[Formula 3]

wherein each of $R_5$ and $R_6$ in the Formula 3 is independently selected from hydrogen or C1 alkyl through C10 alkyl.

10. The organic light emitting diode according to claim 8, further comprising:

an anode; and a cathode, wherein the organic emitting layer is between the anode and the cathode.

11. The organic light emitting diode according to claim 10, wherein the organic emitting layer includes a first layer and a second layer, and wherein the first layer includes the host and the first dopant, and the second layer includes the host and the second dopant.

12. The organic light emitting diode according to claim 11, wherein the first layer is between the anode and the second layer.

13. The organic light emitting diode according to claim 11, wherein the first layer is between the cathode and the second layer.

14. The organic light emitting diode according to claim 11, wherein the organic emitting layer further includes a third layer, and wherein the third layer includes the host and the first dopant, and the second layer is between the first layer and the third layer.

15. The organic light emitting diode according to claim 11, wherein the organic emitting layer further includes a third layer, and wherein the third layer includes the host and the second dopant, and the first layer is between the second layer and the third layer.

16. The organic light emitting diode according to claim 8, wherein a triplet energy of the first dopant is smaller than a triplet energy of the host and larger than a triplet energy of the second dopant.

17. The organic light emitting diode according to claim 8, wherein the host is selected from:

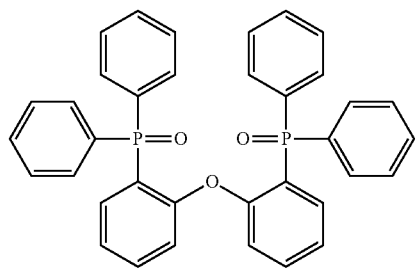

87
-continued
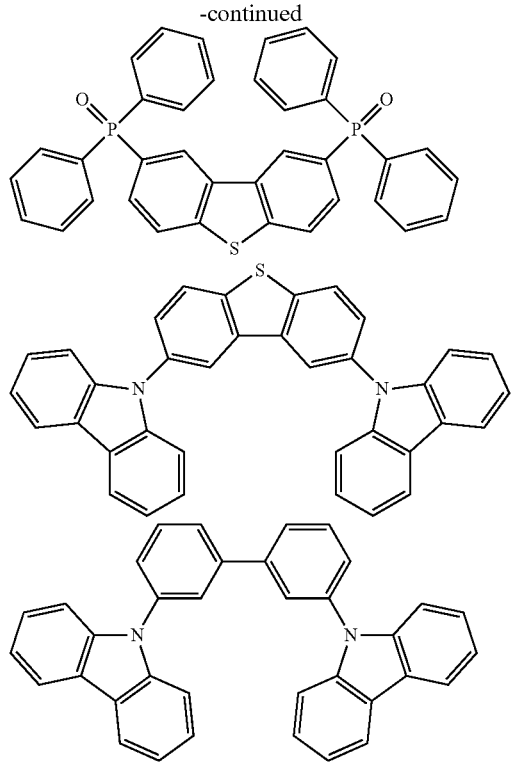
88
-continued
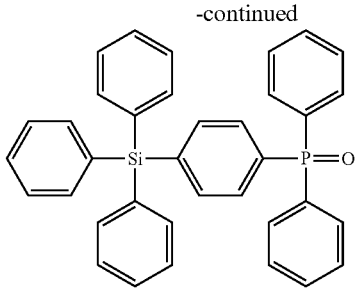
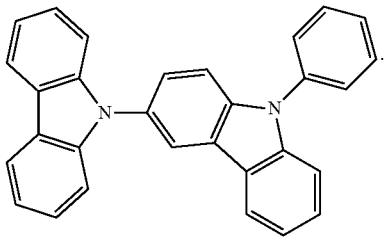
* * * * *